United States Patent [19]
Borden et al.

[11] Patent Number: 6,049,220
[45] Date of Patent: Apr. 11, 2000

[54] APPARATUS AND METHOD FOR EVALUATING A WAFER OF SEMICONDUCTOR MATERIAL

[75] Inventors: Peter G. Borden, San Mateo; Regina G. Nijmeijer; Jiping Li, both of Mountain View, all of Calif.

[73] Assignee: Boxer Cross Incorporated, Menlo Park, Calif.

[21] Appl. No.: 09/095,804

[22] Filed: Jun. 10, 1998

[51] Int. Cl.[7] .......................... G01R 31/26; G01N 21/41
[52] U.S. Cl. .......................... 324/765; 356/432; 356/445
[58] Field of Search .................................. 324/501, 752, 324/765, 766, 767; 356/432, 433, 445

[56] References Cited

U.S. PATENT DOCUMENTS

| | | | |
|---|---|---|---|
| 4,211,488 | 7/1980 | Kleinknecht | 356/433 |
| 4,255,971 | 3/1981 | Rosencwaig | 73/606 |
| 4,273,421 | 6/1981 | Gurtler | 356/433 |
| 4,579,463 | 4/1986 | Rosencwaig et al. | 374/57 |
| 4,632,561 | 12/1986 | Rosencwaig et al. | 356/432 |
| 4,636,088 | 1/1987 | Rosencwaig et al. | 374/5 |
| 4,750,822 | 6/1988 | Rosencwaig et al. | 356/445 |
| 4,854,710 | 8/1989 | Opsal et al. | 356/432 |
| 4,952,063 | 8/1990 | Opsal et al. | 356/432 |
| 5,042,951 | 8/1991 | Gold et al. | 356/369 |
| 5,042,952 | 8/1991 | Opsal et al. | 356/432 |
| 5,159,412 | 10/1992 | Willenborg et al. | 356/445 |
| 5,181,080 | 1/1993 | Fanton et al. | 356/381 |
| 5,228,776 | 7/1993 | Smith et al. | 374/5 |
| 5,379,109 | 1/1995 | Gaskill et al. | 356/445 |

OTHER PUBLICATIONS

Eikelboom et al., "Microwave Detection of Minority Carriers in Solar Cell Silicon Wafers", *Solar Energy Materials and Solar Cells,* Elsevier Science B.V., Oct. 1995, pp. 169–185.

Grove, "Physics and Technology of Semiconductor Devices", John Wiley & Sons, Inc., (month unavailable) 1967, p. 326.

Jackson, "Classical Electrodynamics", John Wiley & Sons, Inc., (month unavailable) 1967, pp. 222–226.

Orton and Blood, "The Electrical Characterization of Semiconductors: Measurement of Minority Carrier Properties", Academic Press, (month unavailable) 1990, pp. 94–100.

Schroder, "Semiconductor Material and Device Characterization", John Wiley & Sons, Inc., (month unavailable) 1990, pp. 2–20, 84–85, 232–235, 304–306, 364, 367–374, 378–383.

Sze, "Physics of Semiconductor Devices", John Wiley & Sons, Inc., (month unavailable) 1981, pp. 50–51.

Paquin, "Properties of Metals", *Handbook of Optics,* vol. II, McGraw–Hill, Inc., (month unavailable) 1995, pp. 35.3–35.7.

Amirtharaj and Seiler, "Optical Properties of Semiconductors", *Handbook of Optics,* vol. II, McGraw–Hill, Inc., (month unavailable) 1995, pp. 36.67–36.68, 36.95, and Table 11.

Rosencwaig et al., "Detection of Thermal Waves Through Optical Reflectance", *Appl. Phys. Lett. 46,* Jun. 1985, pp. 1013–1015.

(List continued on next page.)

*Primary Examiner*—Ernest Karlsen
*Attorney, Agent, or Firm*—Skjerven, Morrill, MacPherson, Franklin & Friel LLP; Omkar K. Suryadevara

[57] ABSTRACT

An apparatus and method uses diffusive modulation (without generating a wave of carriers) for measuring a material property (such as any one or more of: mobility, doping, and lifetime) that is used in evaluating a semiconductor wafer. The measurements are carried out in a small area, for use on wafers having patterns for integrated circuit dice. The measurements are based on measurement of reflectance, for example as a function of carrier concentration. In one implementation, the semiconductor wafer is illuminated with two beams, one with photon energy above the bandgap energy of the semiconductor, and another with photon energy near or below the bandgap. The diameters of the two beams relative to one another are varied to extract additional information about the semiconductor material, for use in measuring, e.g. lifetime.

63 Claims, 21 Drawing Sheets

OTHER PUBLICATIONS

Rosencwaig, "Thermal–Wave Imaging", *Science,* vol. 218, No. 4569, Oct. 1982, pp. 223–228.

Opsal et al., "Thermal–Wave Detection and Thin–Film Thickness Measurements with Laser Beam Deflection", *Applied Optics,* vol. 22, No. 20, Oct. 1983, pp. 3169–3176.

Rosencwaig, "Thermal Wave Characterization and Inspection of Semiconductor Materials and Devices", Chapter 5 (pp. 97–135) of *Photoacoustic and Thermal Wave Phenomena in Semiconductors,* North–Holland, (month unavailable) 1987.

"Process Monitoring System", Quantox Product Brochure, 3 pages, prior to Jun. 10, 1998.

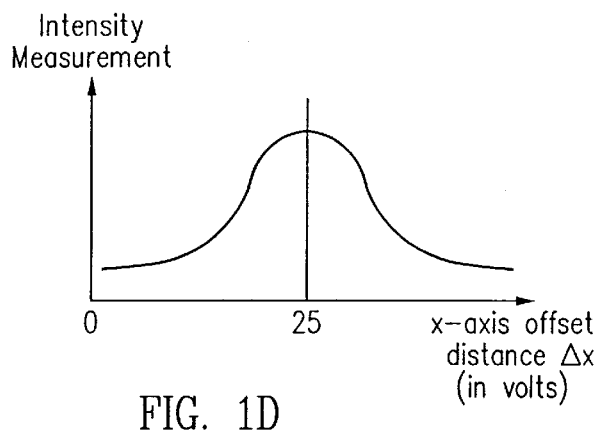
FIG. 1D
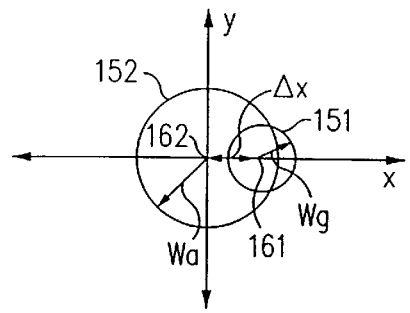
FIG. 1G
FIG. 1E
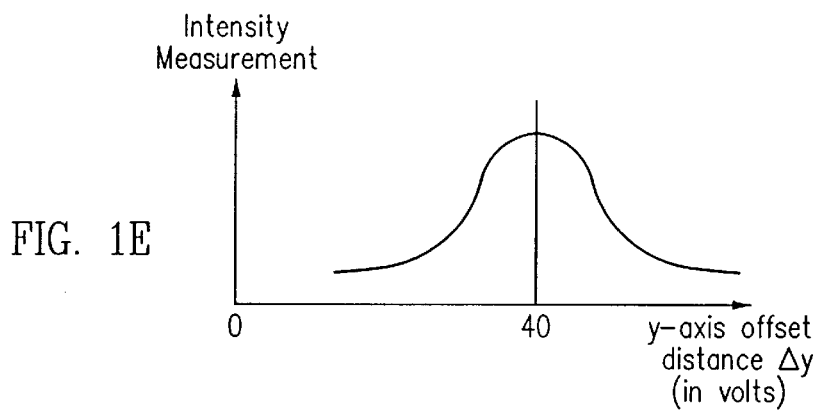
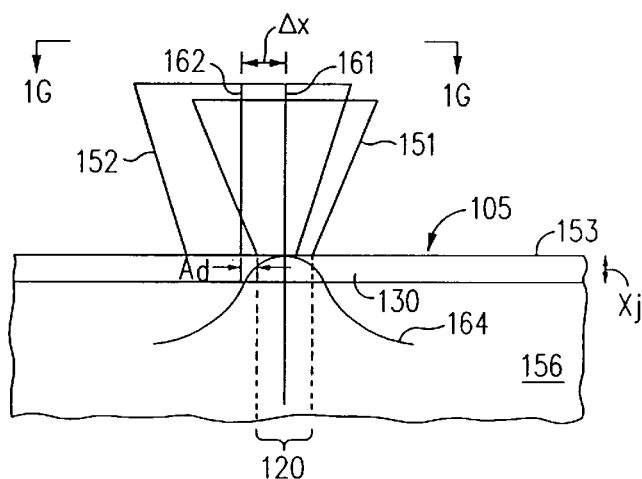
FIG. 1F

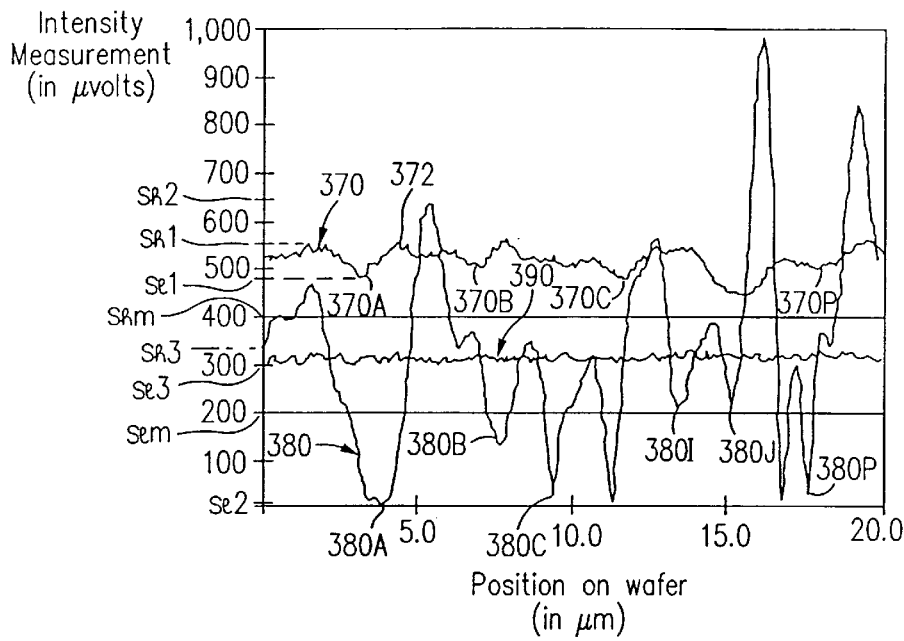
FIG. 3A
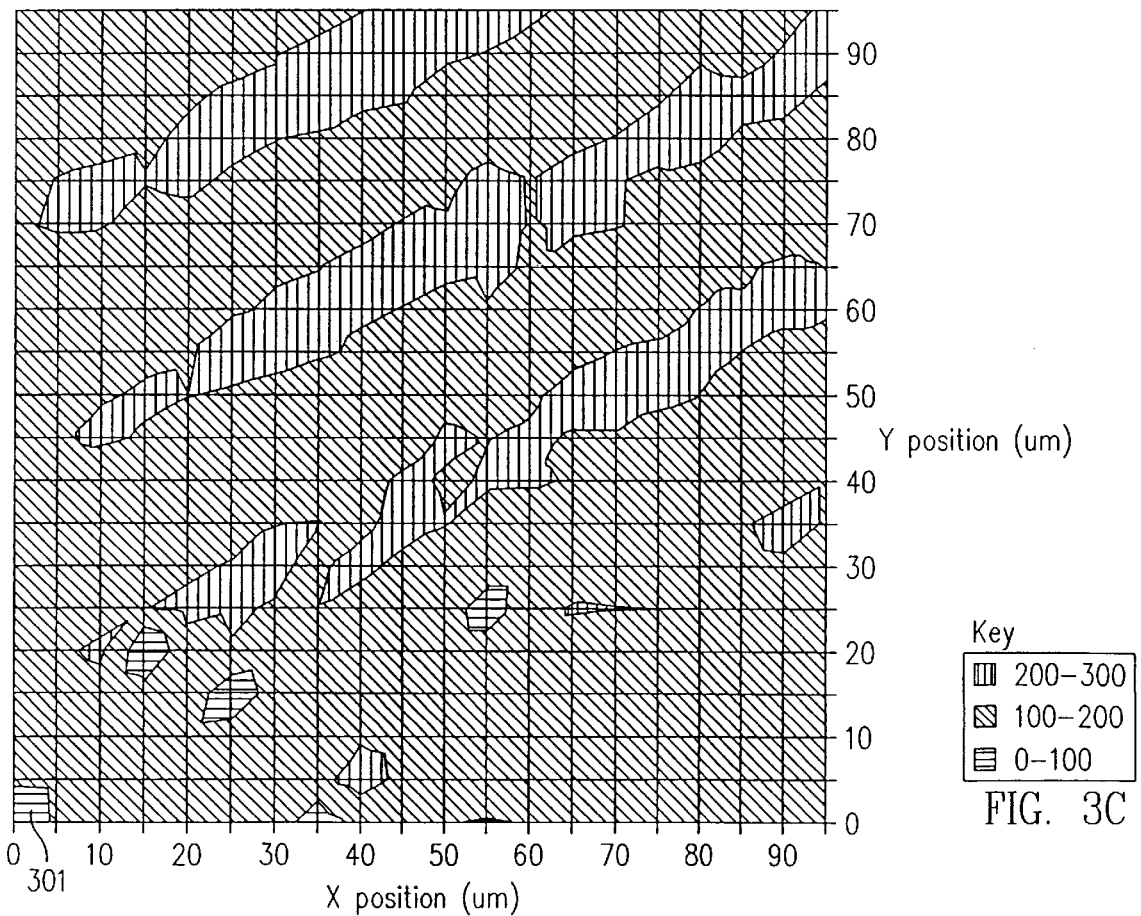
FIG. 3C
FIG. 3B

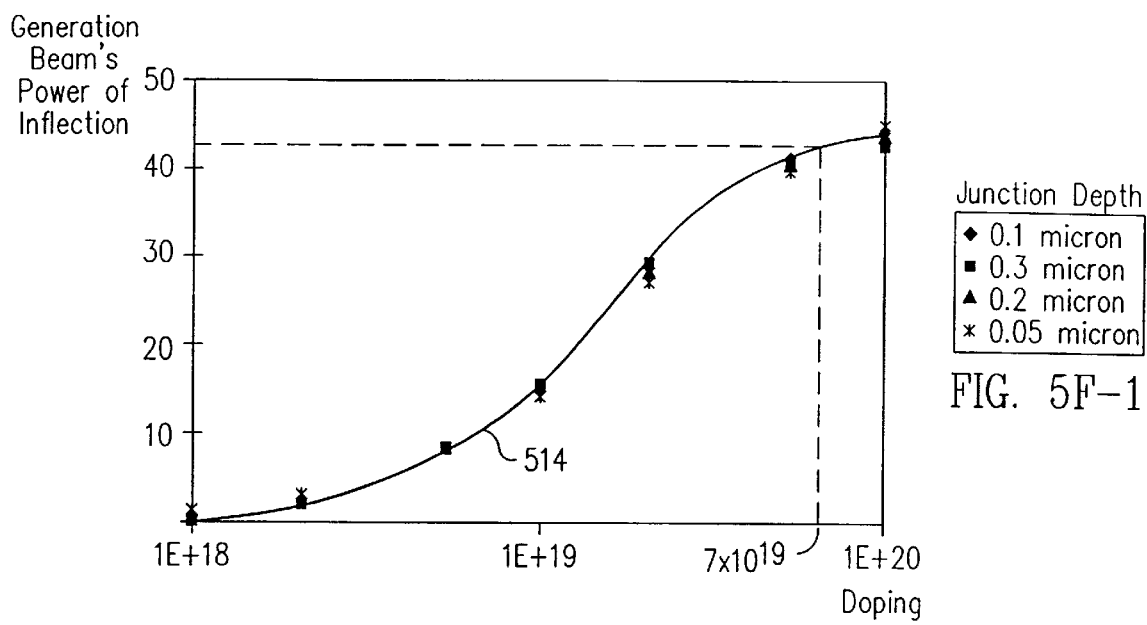
FIG. 5F
FIG. 5F-1
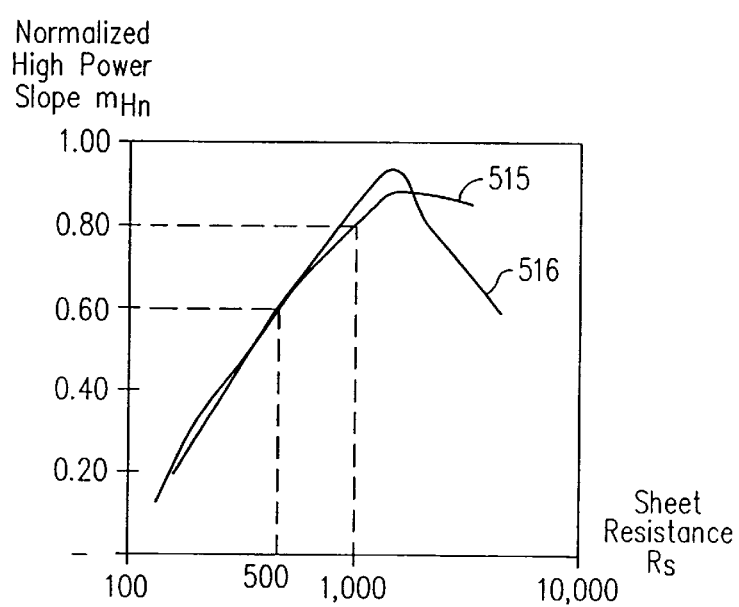
FIG. 5G

APPARATUS AND METHOD FOR EVALUATING A WAFER OF SEMICONDUCTOR MATERIAL

CROSS-REFERENCES TO RELATED APPLICATIONS

This application is related to and incorporates by reference herein in their entirety, the following three commonly owned, copending U.S. Patent Applications:

Ser. No. 08/638,944, entitled "SYSTEM AND METHOD FOR MEASURING THE DOPING CONCENTRATION AND DOPING PROFILE OF A REGION IN A SEMICONDUCTOR SUBSTRATE", filed Apr. 24, 1996, now U.S. Pat. No. 5,883,518, by Peter G. Borden;

Ser. No. 08/637,244, entitled "SYSTEM AND METHOD FOR MEASURING PROPERTIES OF A SEMICONDUCTOR SUBSTRATE IN A FABRICATION LINE," filed Apr. 24, 1996, now U.S. Pat. No. 5,883,518, by Peter G. Borden; and Ser. No. 09/095805, entitled "AN APPARATUS AND METHOD FOR MEASURING A PROPERTY OF A LAYER IN A MULTILAYERED STRUCTURE," filed Jun. 10, 1998, by Peter G. Borden et al.

BACKGROUND OF THE INVENTION

1. Field of the Invention

This invention relates generally to the evaluation of a wafer of semiconductor material, and in particular to the measurement of a property of the semiconductor material.

2. Description of Related Art

In the processing of a semiconductor wafer to form integrated circuits, charged atoms or molecules are directly introduced into the wafer in a process called ion implantation. Ion implantation normally causes damage to the lattice structure of the wafer, and to remove the damage, the wafer is normally annealed at an elevated temperature, typically 600° C. to 1100° C. Prior to annealing, material properties at the surface of the wafer may be measured, specifically by using the damage caused by ion implantation.

For example, U.S. Pat. No. 4,579,463 granted to Rosencwaig et al. (that is incorporated herein by reference in its entirety) describes a method for measuring a change in reflectance caused by a periodic change in temperature of a wafer's surface (see column 1, lines 7–16). Specifically, the method uses "thermal waves [that] are created by generating a periodic localized heating at a spot on the surface of a sample" (column 3, lines 54–56) with "a radiation probe beam . . . directed on a portion of the periodically heated area on the sample surface," and the method "measur[es] the intensity variations of the reflected radiation probe beam resulting from the periodic heating" (column 3, lines 52–66).

As another example, U.S. Pat. No. 4,854,710 to Opsal et al. (also incorporated herein by reference in its entirety) describes a method wherein "the density variations of a diffusing electron-hole plasma are monitored to yield information about features in a semiconductor" (column 1, lines 61–63). Specifically, Opsal et al. state that "changes in the index of refraction, due to the variations in plasma density, can be detected by reflecting a probe beam off the surface of the sample within the area which has been excited" (column 2, lines 23–31) as described in "Picosecond Ellipsometry of Transient Electron-Hole Plasmas in Germanium," by D. H. Auston et al., Physical Review Letters, Vol. 32, No. 20, May 20, 1974.

Opsal et al. further state (in column 5, lines 25–31 of U.S. Pat. No. 4,854,710): "The radiation probe will undergo changes in both intensity and phase. In the preferred embodiment, the changes in intensity, caused by changes in reflectivity of the sample, are monitored using a photodetector. It is possible to detect changes in phase through interferometric techniques or by monitoring the periodic angular deflections of the probe beam."

A brochure entitled "TP-500: The next generation ion implant monitor" dated April, 1996 published by Therma-Wave, Inc., 1250 Reliance Way, Fremont, Calif. 94539, describes a measurement device TP-500 that requires "no post-implant processing" (column 1, lines 6–7, page 2) and that "measures lattice damage" (column 2, line 32, page 2). The TP-500 includes "[t]wo low-power lasers [that] provide a modulated reflectance signal that measures the subsurface damage to the silicon lattice created by implantation. As the dose increases, so does the damage and the strength of the TW signal. This non-contact technique has no harmful effect on production wafers" (columns 1 and 2 on page 2). According to the brochure, TP-500 can also be used after annealing, specifically to "optimize . . . system for annealing uniformity and assure good repeatability" (see bottom of column 2, on page 4).

SUMMARY

A method in accordance with this invention: (1) creates charge carriers in a concentration that changes in a cyclical manner (also called "modulation") only with respect to time, in a region (also called "illuminated region") of a semiconductor material, and preferably also (2) maintains the charge carriers at an average concentration that remains the same (or at least approximately the same e.g. varies less than 10%) before and during a measurement indicative of the number of charge carriers created in the illuminated region by act (1).

In one embodiment (also called "scanning embodiment"), one or more such measurements are compared each with the other, thereby to identify a sudden change in the measurements. In another embodiment (also called "measurement embodiment"), one or more measurements are compared with similar measurements on wafers (also called "reference wafers") processed under known conditions and having known properties, thereby to determine one or more process conditions or properties of a wafer under fabrication.

In one implementation, an attribute derived from measurements on a wafer is interpolated with respect to corresponding attributes of wafers having a known material property (or process condition), thereby to determine a corresponding property (or condition) of the wafer under measurement. An example of a process condition is the temperature (also called "annealing temperature") at which the wafer is annealed. Examples of material properties include surface concentration, mobility, junction depth, lifetime and defects that cause leakage current at the junction (when the junction is reversed biased).

The charge carriers (also called "excess carriers") being created and measured as described above are in excess of a number of charge carriers (also called "background charge carriers") that are normally present in the semiconductor material (e.g. due to dopant atoms) even in the absence of illumination. Therefore, in the first act described above, a number of excess carriers are created in the above-discussed region (also called "illuminated region"), e.g. by focusing thereon a laser beam or an electron beam. The concentration of excess carriers is modulated, both at the surface and in the bulk only as a function of time (e.g. by modulating the intensity of the just-described laser or electron beam that is also called "generation beam").

The frequency of modulation of the concentration of excess carriers is deliberately selected to be sufficiently low to avoid modulation in space (i.e. avoid the creation of a wave of charge carriers). A carrier concentration that is devoid of a wave in space is created when at least a majority of the charge carriers (i.e. greater than 50%) move out of the illuminated region by diffusion. Such a temporal modulation under diffusive conditions (also called "diffusive modulation") is used to measure the reflectance caused by excess carriers, e.g. by detection of the intensity of a beam (also called a "probe beam") reflected by the illuminated region at the modulation frequency.

In the second act, an average concentration (e.g. root mean square average) of the excess carriers is determined from a measurement of the above-described reflectance over the time period of a modulation cycle. The average concentration is maintained the same (or approximately the same) prior to and during the measurement of reflectance. Specifically, the creation of new charge carriers (also called "measurement-related" carriers) in addition to the background charge carriers and the excess carriers is minimized or avoided during the reflectance measurement, thereby to maintain the total carrier concentration at or about the just-described average prior to the measurements.

An apparatus (also called "profiler") that implements the above-described method includes, in one embodiment, a source that produces a probe beam formed of photons of energy lower than the bandgap energy (the energy necessary to generate conduction electrons) of the semiconductor material. Use of such a probe beam source eliminates the measurement-related carriers and the resulting errors that are otherwise created by a prior art apparatus, e.g. in measuring the reflectance with a probe beam that has photons of energy greater than the bandgap energy of silicon (such as the He—Ne laser probe beam described at column 15, line 56 of U.S. Pat. No. 4,854,710).

In addition to the above-described probe beam source, the profiler also includes a photosensitive element (such as a "photodiode") that is located in the path of a portion of the probe beam reflected by the illuminated region. The photosensitive element generates an electrical signal (e.g. a voltage level) that indicates the intensity of the probe beam portion reflected by the illuminated region. The intensity in turn indicates reflectance caused by the excess charge carriers (e.g. created by incidence of a generation beam).

So, in one embodiment, the intensity measurement is used by the profiler as a measure of the concentration of excess charge carriers in the illuminated region. In this embodiment, the profiler also includes a computer that is coupled to the photosensitive element to receive the electrical signal, and that is programmed to determine the value of a material property in the illuminated region from one or more such measurements.

In another embodiment, the profiler creates measurement-related carriers by use of a probe beam having photons at or slightly above the bandgap energy of the semiconductor material. Even in the presence of such measurement-related carriers, the profiler maintains the overall accuracy of a measurement of a material property (as described herein) within a predetermined limit (e.g. 10% error) by limiting the number of such measurement-related carriers to a small percentage (e.g. up to 10%) of the excess carriers.

In the just-described embodiment, a diffusive modulation of charge carriers is created by use of a generation beam that has a wavelength and power chosen so that the rate of carriers generated by this beam is sufficiently larger, e.g. one order (preferably two orders) of magnitude larger than the rate of carriers generated by the probe beam so as to make the latter negligible.

In one implementation, in addition to the above-described probe beam source, the profiler includes a source that produces a generation beam (formed of photons) having an intensity that is modulated at a sufficiently low frequency to avoid creation of a wave of charge carriers. The powers of the two beams are maintained by the profiler to be at least approximately the same. Other implementations have two beams that each have a power different from the other, and yet maintain the measurement-related carriers (created by the probe beam) at a negligible percentage (e.g. the probe beam has photons of energy higher than the bandgap energy but has a power that is half or one-fourth the power of the generation beam, assuming that the power of the reflected portion of the probe beam is detected with sufficient accuracy as described above).

Measurement of intensity of a reflected portion of the probe beam while (1) using diffusive modulation and (2) generating negligible (preferably none) percentage of measurement-related carriers is a critical aspect of one embodiment of the invention. One or more such measurements provide a measure of a process condition or a property of the semiconductor material in the illuminated region. Such measurements are performed in one embodiment after annealing to activate the dopants, thereby to obtain a measure that is more indicative of the electrical behavior of the devices being fabricated than a property that is measured prior to annealing (as described in U.S. Pat. No. 4,854,710).

The above-described intensity measurements (from which reflectance measurements are derived), and one or more properties (also called "material properties") are preferably (but not necessarily) monitored during fabrication, to control a process step (e.g. to control annealing temperature of a wafer that has been ion implanted) used in fabricating a wafer. As the material properties are measured directly on the wafer undergoing fabrication (also called "patterned wafer" or "annealed wafer" depending on the stage of fabrication), a measurement as described herein increases yield, as compared to an off-line measurement of a test wafer's properties.

During operation, the profiler (described above) performs a number of reflectance measurements, each measurement being for a different value of a parameter used either (1) in the generation of the excess carriers or (2) in the measurement of the concentration of excess carriers. In one embodiment, the profiler fits two or more such measurements to one or more straight lines or to a curved line, and compares an attribute of the fitted line (e.g. compares a first order coefficient, also called "slope," of the fitted line), with corresponding attributes of corresponding lines generated from such measurements on wafers having known properties, thereby to determine a material property corresponding to the fitted line.

Moreover, a process condition (e.g. the temperature at which a patterned wafer has been annealed) can also be determined from such comparison of reflectance measurements, if the process condition affects the semiconductor material. Depending on the implementation, the comparison can be performed either manually or by a computer.

In a first implementation, the parameter varied between the measurements is the average concentration of charge carriers that is controlled by, e.g., changing the power or the diameter of the generation beam used to generate the charge carriers. Thereafter, a material property, such as mobility (or junction depth) is determined from intensity measurements by comparison of the above-described attribute with the corresponding attributes of wafers having known mobilities (or junction depths).

In one example, the wafer is undoped and mobility is determined by computing the slope of a plot of the intensity measurement against the power of the generation beam. In another example, the wafer has doped regions, and mobility is determined by comparing a slope obtained from the measurements (in the same manner as the just-described slope for the undoped wafer) with slopes of wafers having known mobilities.

In a second implementation, the varied parameter is the distance between the two beams that are used in performing an intensity measurement. In two variants of this implementation, the location of either (1) the generation beam, or (2) the probe beam, is changed relative to the wafer. The material property determined from such intensity measurements is lifetime.

In a third implementation, the parameter that is varied is the relative size of the two beams used in the intensity measurement e.g. the diameter of the probe beam is changed (while keeping the power of the probe beam the same). In this implementation as well, the material property determined from the intensity measurements is lifetime.

In another embodiment (also called "polarized embodiment"), a laser beam that is linearly polarized is used as a probe beam (also called "polarized probe beam"). The polarized probe beam need not have photons of energy below the bandgap energy of the semiconductor material, i.e. a beam of photons at or slightly above the bandgap energy (as described above) can be used if polarized.

On reflection from the illuminated region, a plane of polarization of the probe beam rotates through two different angles, depending on the following two reflection coefficients: one coefficient in a plane (also called "surface plane") of the surface of the illuminated region, and another coefficient in a plane (also called "normal plane") perpendicular to the surface plane.

After reflection, a portion of the probe beam that has been reflected is interfered with another portion that was not reflected. Next, two measurements are made, specifically of the sum and difference signals generated by the interference. Thereafter, a difference (hereinafter "in-phase difference") between the two measurements that is in phase with the modulation of charge carriers is determined using a phase detector. The in-phase difference signal provides a measure of the concentration of excess carriers in the illuminated region.

Thereafter, one or more of the material properties discussed above are determined by use of in-phase difference signal (instead of using the intensity measurement described above). Use of a polarized probe beam (as described herein) provides an increase in sensitivity of the measurement of material properties by about two orders of magnitude over the use of a non-polarized beam, because of the increased sensitivity of a phase detector used in the polarized embodiment (as compared to an amplitude detector that is otherwise used) to measure the power of the reflected portion of the probe beam.

BRIEF DESCRIPTION OF THE DRAWINGS

FIGS. 1D and 1E illustrate, in graphs, variation of a measurement of intensity of a portion of the probe beam reflected by the wafer of FIG. 1C, as a function of a piezoelectric voltage that controls the distance between the two beams of FIG. 1C along axis x (FIG. 1D) and axis y (FIG. 1E), the two axes being illustrated in FIG. 8A.

FIGS. 1F and 1G illustrate, in a cross-sectional view and a plan view respectively, beams 151 and 152 of FIG. 1C offset from each other, (and also superimposed in the view of FIG. 1F is a graph of the concentration 164 of excess charge carriers as a function of the distance from axis 161 of generation beam 151).

FIG. 3A illustrates, in a graph, intensity measurements (made by the profiler of FIG. 1A in a scanning embodiment) plotted along y axis as a function of position along the x axis for three wafers.

FIG. 3B illustrates in a two-dimensional map, intensity measurements obtained from scanning an area 95×95 $\mu m^2$ of an annealed, ion implanted wafer.

FIG. 3C illustrates, in a key, values of intensity measurements (in units of microvolts) shown in the map of FIG. 3B.

FIG. 5F illustrates, in a graph, another attribute (specifically the inflection point) of a line in FIG. 5A plotted along the y axis as a function of the doping concentration on the x axis for wafers having four different junctions depths.

FIG. 5F–I illustrates, in a key, values of junction depth down in FIG. 5F.

FIG. 5G illustrates, in a graph, a normalized attribute (specifically the normalized high power slope) plotted along the y axis as a function of the sheet resistance (in ohms per square) plotted along the x axis.

FIG. 5H illustrates, in a graph, the variation of high power slope $m_H$ plotted along the y axis as a function of mobility plotted along the x axis.

DETAILED DESCRIPTION

Figure 1A:
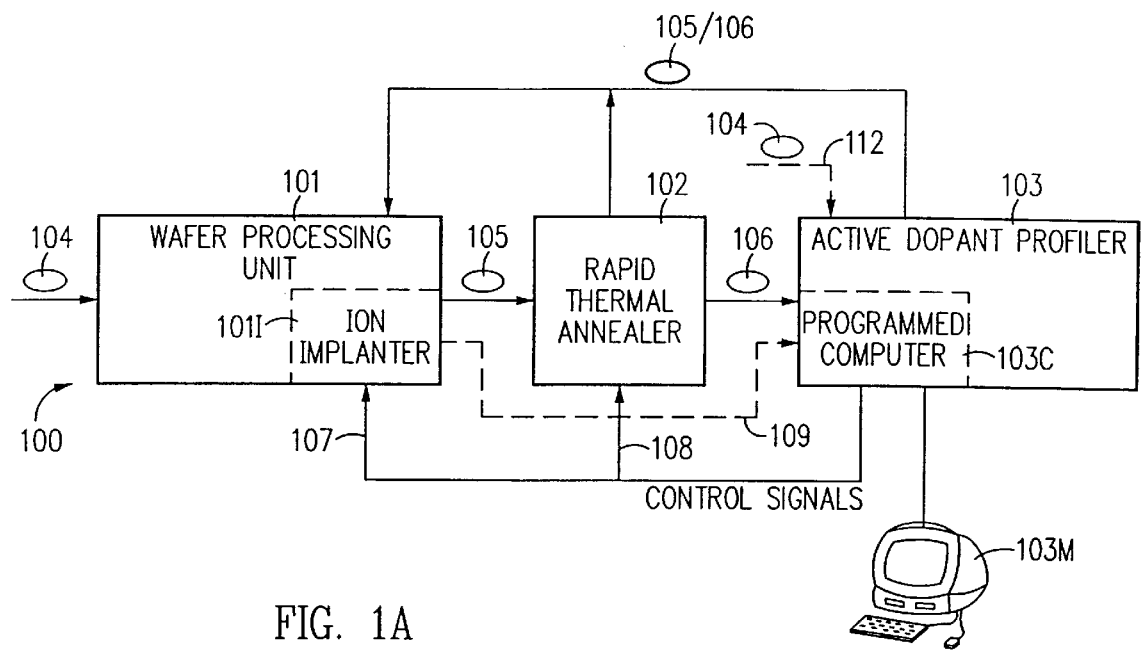
FIG. 1A illustrates, in a high level block diagram, a system including an apparatus (called "active dopant profiler") in accordance with the invention.

A wafer fabrication system 100 (FIG. 1A) in accordance with the invention is used to create integrated circuit (abbreviated as "IC") dice by processing a wafer to form a "patterned wafer", measuring a material property of the patterned wafer, and adjusting the processing in real time if necessary. The just-described processing can include annealing, and the measurement of a material property can be performed on a patterned wafer after annealing, thereby to determine process conditions not obtainable by prior art methods, e.g. to determine anneal temperature from measurements on the annealed wafer. Measurements on patterned wafers during fabrication as described herein eliminates test wafers that may be otherwise required in the prior art solely to monitor the fabrication process, thus reducing costs. Moreover, measurements on annealed wafers as described herein provide a measure of one or more properties that are related to the electrical characteristics (such as processing speed) of the devices being fabricated, because annealing results in activation of the dopants used in the devices.

System 100 includes a wafer processing unit 101 that performs an act 211 (FIG. 2A) e.g. by operating an ion implanter 101I to create, in a wafer 104 (FIG. 1A), one or more regions (e.g. doped region 130 in FIG. 1C) that have dopant atoms (e.g. boron atoms in silicon). Instead of ion implantation, any other process for creating doped regions, e.g. chemical vapor deposition, epitaxial deposition, evaporation, diffusion, or plasma deposition can be used in unit 101 (FIG. 1A) to perform act 211.

Figure 2A:
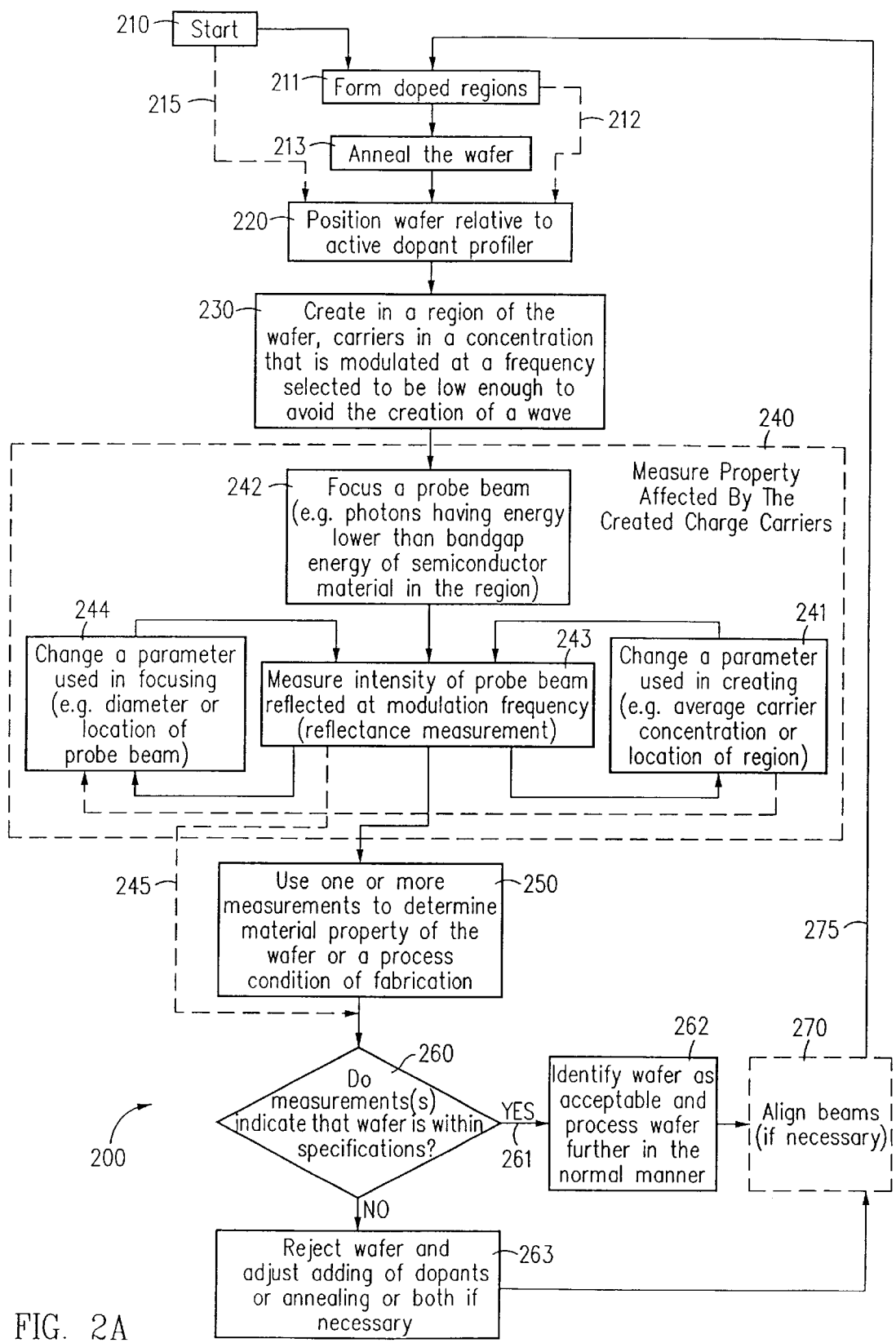
FIG. 2A illustrates, in a flowchart, the acts performed by the system of FIG. 1A in one implementation.

Thereafter, a patterned wafer 105 having one or more patterns of doped regions is transferred to a rapid thermal annealer 102 (FIG. 1A) that may be included in system 100. Rapid thermal annealer (also called "annealer") 102 performs an annealing act 213 (FIG. 2A), e.g. by heating wafer 105 (FIG. 1A) to a predetermined temperature (also called "annealing temperature"), e.g. to remove damage that is normally caused by ion implanter 101 to the lattice structure of the semiconductor material in the doped regions of wafer 105. Instead of a rapid thermal annealer, a furnace may be included in system 100 and used to anneal wafer 105 in act 213 (FIG. 2A).

Annealing in act 213 causes the dopant atoms (also called "dopants") to move into the lattice of the semiconductor material in a doped region 130, where the dopants act as donors (forming n-type material) or acceptors (forming p-type material). The extent to which the dopants incorporate into the lattice structure during act 213 is a function of the temperature at which and the time for which act 213 is performed. The incorporation is more complete at a higher temperature or after a longer time.

However, the dopants also diffuse (i.e. move) during act 213, thereby increasing the junction depth. The diffusion proceeds more rapidly at a higher temperature, and it is necessary to carefully control the annealing temperature. Therefore, a profile of the concentration of dopants as a function of depth is measured after act 213, and the profile is compared with predetermined information (e.g. a specification or profiles of wafers known to be good) to determine a change (if any) to be made to the annealing process. Dynamic feedback of such to-be-made changes to the annealing process in real time as described herein improves the yield of good wafers obtained from annealing in a manner not otherwise possible in the prior art.

Therefore, an annealed wafer 106 (FIG. 1A) is transferred from rapid thermal annealer 102 to a measurement device (hereinafter "active dopant profiler" or "profiler") 103, and positioned therein (see act 220 in FIG. 2A). In an alternative embodiment, an active dopant profiler is integrated into a rapid thermal annealer and does not require positioning after completion of anneal. In one embodiment, profiler 103 is moved relative to wafer 106 instead of moving wafer 104.

Also, a non-annealed wafer 105 can be used (moved via path 109 in FIG. 1A) as illustrated by branch 212 in FIG. 2A e.g. if dopant regions do not require annealing due to use of a method other than ion implantation, such as diffusion (wherein dopants are diffused into wafer 105 thermally, and are active, and there is no need to anneal out implant damage). Profiler 103 evaluates the efficacy of the dopants in a nonannealed wafer 105 in a manner similar to that described above for annealed wafer 106. A starting wafer 104 can also be used as illustrated by path 112 in FIG. 1A and by branch 215 in FIG. 2A. Therefore, in the following description, the notation "104/105/106" is used to indicate that the description is equally applicable to each of wafers 104, 105 and 106. Similarly the notation "105/106" indicates each of wafers 105 and 106.

Next, after a wafer 104/105/106 is properly positioned, profiler 103 creates (see act 230 in FIG. 2A) in a region of the wafer, a number of charge carriers that are modulated at a predetermined frequency. The predetermined frequency is selected to ensure that a wave of the charge carriers is not created during the act of measurement (see act 240 in FIG. 2A). As profiler 103 does not use a "plasma wave" as described in U.S. Pat. No. 4,854,710, profiler 103 is as effective in measuring a property of an annealed wafer 106 as in measuring a property of a non-annealed wafer 104/105.

Figure 6A:
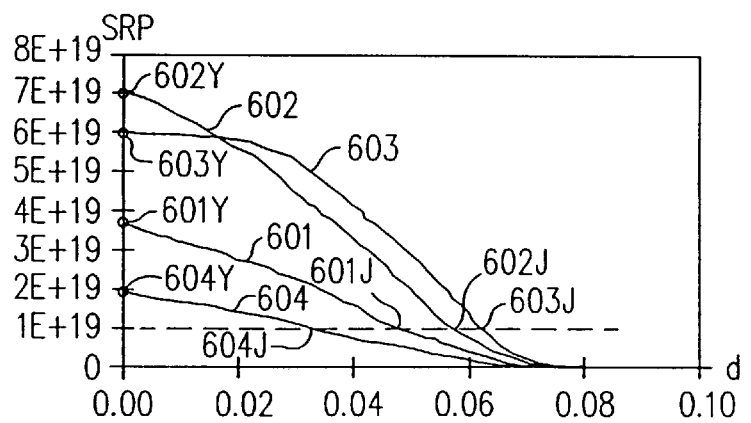
FIG. 6A illustrates, in a graph, the spreading resistance profile SRP (plotted along the y axis) as a function of the depth d (plotted along the x axis) from wafer surface 153 (FIG. 1C).

Profiler 103 (FIG. 1A) measures a property (in act 240 in FIG. 2A) that is affected by charge carriers present in a doped region 130 (FIG. 1C) in a wafer 105/106, In one implementation, profiler 103 measures the reflectance that is thereafter used to determine various properties such as mobility, junction depth, surface carrier concentration, doping concentration, lifetime, and the number of active dopants as a function of depth "d" from surface 153 of wafer 105/106. A function (called "active dopant profile") can be plotted in a graph as illustrated in FIG. 6A described below. In act 240, instead of the reflectance, profiler 103 can measure other properties affected by the created charge carriers, such as the refractive index.

One or more of these measurements are used (see act 260 in FIG. 2A) to determine if annealed wafer 106 conforms to the specification for such wafers. If wafer 106 conforms to the specifications, wafer 106 is identified as acceptable (e.g. by movement in the direction for further processing) and the conditions in wafer processing unit 101 (FIG. 1A) and in rapid thermal annealer 102 are left undisturbed. Thereafter, the above-described acts are repeated (as illustrated by branch 275) on another wafer or after further processing on the same wafer.

If a wafer 106 does not conform to the specifications, wafer 106 is identified as unacceptable (e.g. discarded) and optionally profiler 103 is used (in act 263 in FIG. 2A) to adjust (either automatically or under manual control) (1) the conditions (e.g. dosage of dopants) in unit 101 by driving a signal on a line 107 (FIG. 1A), or (2) the conditions (e.g. annealing temperature) in annealer 102 by driving a signal on line 108, or both. Then the above-described acts and acts are again repeated (as illustrated by branch 275).

Profiler 103 can perform an alignment at any time (e.g. after identifying a wafer as accepted/rejected as shown by act 270 in FIG. 2A). In one embodiment, profiler 103 includes two piezoelectric actuators that control the positions of beams 151 and 152. Specifically, the actuators (not shown) move a collimating lens of a laser that generates probe beam 152 along each of two orthogonal axes x, y that are both perpendicular to axis 155 of generation beam 151, thereby shifting the position of probe beam 152 relative to generation beam 151.

In this particular embodiment, profiler 103 aligns (see act 270 in FIG. 2A) beams 151 and 152 to be coincident in the following manner. Specifically, profiler 103 repeatedly moves probe beam 152 relative to probe beam 151 along an axis (e.g. along x axis), as illustrated in FIGS. 1F and 1G and obtains an intensity measurements after each movement. Thereafter, profiler 103 optionally plots the intensity measurements as a function of the relative position as illustrated in FIG. 1D, and determines the position (in this embodiment the voltage applied to the piezoelectric actuator) at which the intensity measurement is at a maximum, e.g. 25 volts in FIG. 1D.

Figure 2B:
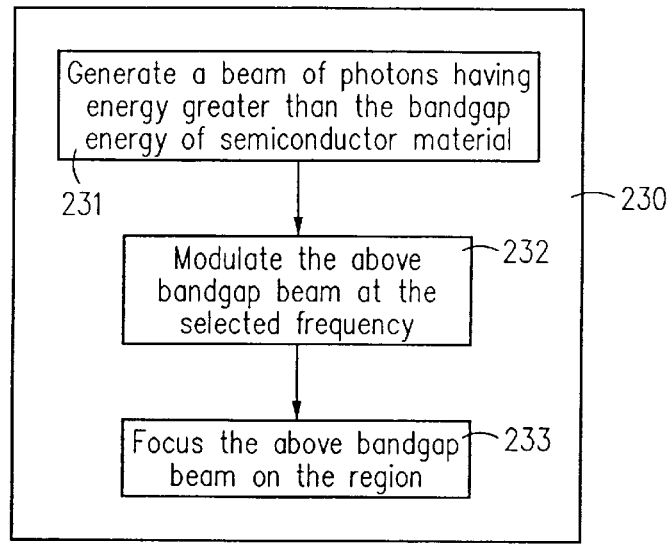
FIG. 2B illustrates, in a flowchart, creation of charge carriers by the generation beam of FIG. 1C.
Figure 2C:
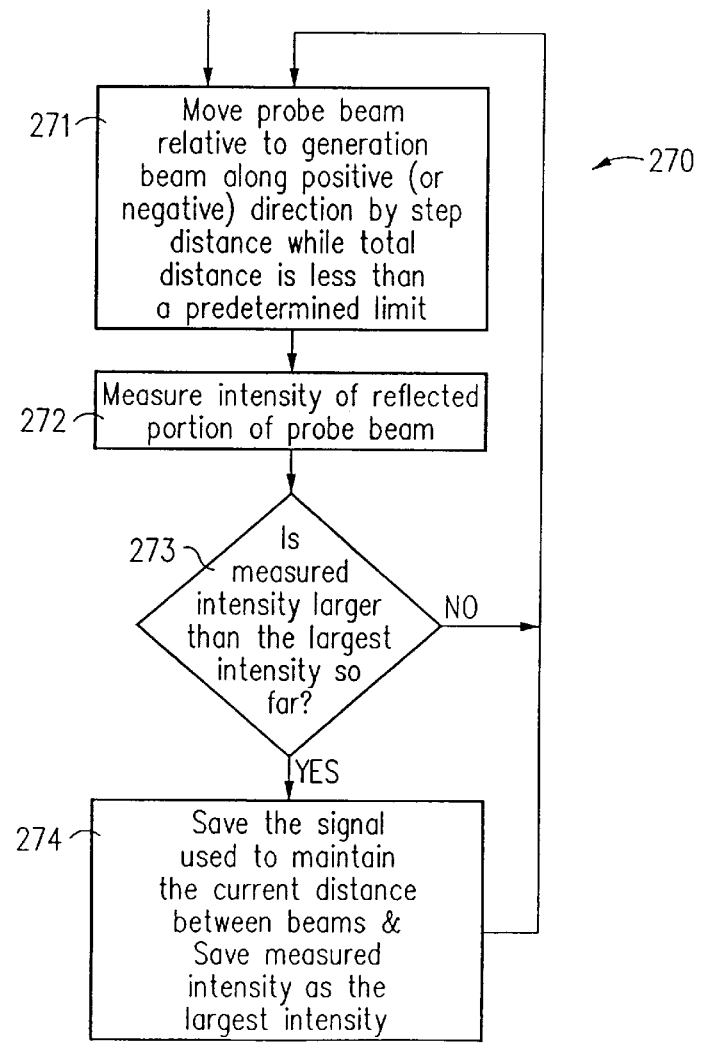
FIG. 2C illustrates, in a flow chart, the acts performed by profiler 103 of FIG. 1A to align two beams for use in reflectance measurement with coincident beams.

In one embodiment, profiler 103 moves (see act 271 in FIG. 2C) probe beam 152 relative to generation beam 151 in a first direction (e.g. along the positive x axis) by an incremental distance $\Delta x$ (e.g. 0.1 $\mu$m), measures (see act 272) if the measured intensity is larger than the largest intensity so far, and if so, saves (see act 274 the voltage signal that was used to maintain the current total distance between beams 151 and 152 and also saves the measured intensity as the largest intensity. Thereafter, profiler 103 repeats acts 271–274 until the total distance between beams 151 and 152 will exceed a predetermined distance, e.g. ½ of the diameter of the larger of beams 151 and 152, wherein the incremental distance $\Delta x$ is 1/10 of the larger diameter.

Next, profiler 103 moves probe beam 152 relative to generation beam 151 in a second direction (e.g. along the negative x axis) that is opposite to the first direction, and performs acts 271–274. Profiler 103 uses the value of the largest intensity from the previous performance of acts 271–274 during act 273 in the second direction performed for the first time—e.g. treats the negative and positive x axis travel to be a continuum and so obtains the voltage signal of 25 volts (FIG. 1D) corresponding to the maximum intensity measurement along x axis.

Similarly, profiler 103 moves probe beam 152 relative to generation beam 151 along another axis (e.g. y axis) that is orthogonal to the just-described movement, and once again determines the voltage applied to the piezoelectric actuator at which the intensity measurement is maximum, e.g. 40 volts in FIG. 1E. Therefore, profiler 103 automatically connects drift in optical alignment by performing act 270.

Thereafter, profiler 103 uses the just-described voltage levels to align the two beams, thereby to ensure that beams 151 and 152 remain coincident in the next set of measurements. Profiler 103 performs such alignment of beams 151 and 152 as often as required to obtain intensity measurements within the accuracy required by the system, e.g. once every N measurements (e.g. if profiler 103 is known to maintain alignment within the required accuracy for N measurements). In one particular example, the number of movements N between two acts of alignment is 1000.

As described below, the measurement performed by profiler 103 is non-destructive, is performed in a few square microns, and can be performed in a relatively short time (e.g. five seconds in one region or 50 seconds at 10 regions over a wafer). Measuring a property of annealed wafer 106 during (or immediately after) fabrication as described herein increases yield, as compared to an off-line measurement of a test wafer's properties.

Prior to measuring a material property by performing act 240, profiler 103 creates (see act 230 in FIG. 2A), in a region 120 (also called "illuminated region") of wafer 106, a concentration ne of excess carriers, and modulates concentration ne (i.e. increases and decreases) as a function of time t but not as a function of distance x from a central axis 155 (FIG. 1C) of region 120. Specifically, over a time period that is the inverse of the modulation frequency, profiler 103 changes concentration ne between the values $n_{ea}-n_{en}$, wherein $n_{en} \leq n_{ej} \leq n_{ei} \leq n_{ea}$ (FIG. 1B). Therefore, at any given time ti, the value $n_{ei}$ of the carrier concentration in semiconductor material 156 decays as a function of the distance x, without the creation of a wave in space. Profiler 103 ensures that there is no periodicity in space of the value of concentration ne. Instead, concentration $n_e$ simply decays radially (e.g. roughly exponentially as a function of radial distance) outside region 120, as illustrated in FIG. 1B.

To ensure the absence of a wave in space, the frequency of modulation of carrier concentration C is selected to be several times (e.g. one or more orders of magnitude) smaller than the modulation frequencies used in the prior art to generate waves as described in, for example, U.S. Pat. No. 4,854,710. Specifically, in one implementation of this invention, the modulation frequency is approximately 1 KHz that is one thousand times (three orders of magnitude) smaller than a 1 MHz frequency described in column 15, line 18 of U.S. Pat. No. 4,854,710 by Opsal. Use of such a low modulation frequency is a critical aspect in one embodiment, and leads to unexpected results due to the elimination of a wave in space, such as the "wave" described by Opsal. In another embodiment, the modulation frequency is any frequency lower than 1000 Khz (e.g. 900 Khz) and profiler 103 still provides a measure of a material property as described herein.

In one embodiment, profiler 103 implements the above-described act 230 (FIG. 2A) by: generating (act 231 in FIG. 2B) a beam 151 (FIG. 1C) of photons that have energy greater than the bandgap energy of the semiconductor material in doped region 130, modulating (act 232 in FIG. 2B) beam 151 at a frequency selected to avoid the creation of a wave (as described above), and focusing (act 233 in FIG. 2B) beam 151 on doped region 130.

Depending on the implementation, profiler 103 modulates the intensity of generation beam 151 at any frequency in the range of 1 Hz to 20,000 Hz, as described below in reference to FIG. 4B. The modulation frequency can be, for example, 1000 Hz, and may require at least 10 cycles for a lock-in amplifier to generate a reflectance measurement (based on a probe beam as described below in reference to act 242), or 10 milliseconds to perform each reflectance measurement. In one example, the throughput is 30 wafers per hour, or 120 seconds per wafer, with each wafer having a measurement taken in at least ten regions.

If a material property measurement requires several reflectance measurements (e.g. a single region 120 requires a number of reflectance measurements for each of a corresponding number of average carrier concentrations), profiler 103 takes several seconds (e.g. 10 seconds) for each wafer 104/105/106. Hence, the 10 millisecond speed of reflectance measurement per region allows for real time control in the fabrication of wafers by apparatus 100 (FIG. 1A) using method 200 (FIG. 2A).

In another implementation of act 230, instead of using beam 151 of photons, profiler 103 uses a beam of charged particles, such as electrons or ions. The beam of charged particles is modulated and focused in the same manner as that described above in reference to beam 151 to generate the charge carriers in doped region 130. Instead of a beam of photons or a beam of electrons, any other mechanism (such as a combination of photons and electrons) can be used to create charge carriers in act 230 (FIG. 2A).

In act 240, one implementation of profiler 103 focuses (see act 242 in FIG. 2A) on a region (also called "illuminated region") 120 illuminated by beam 151, another beam 152 (FIG. 1C) that is used to detect the number of charge carriers in wafer 104/105/106 when illuminated by beam 151. In one embodiment, beam 152 (also called "probe beam") contains photons having energy lower than the bandgap energy of the semiconductor material in illuminated region 120. Such a probe beam 152 avoids the creation of measurement-related carriers when beam 152 is incident on illuminated region 120, thereby to maintain the charge carrier concentration the same prior to and during measurement (see act 243 in FIG. 2A) of a property as described below.

Next, profiler 103 measures (see act 243 in FIG. 2A) the intensity of a reflected portion of beam 152 (FIG. 1C) that is modulated at the frequency of modulation of the charge carriers in illuminated region 120. The intensity measurement provides an indication of an average concentration $n_{av}$ of charge carriers in doped region 130 near surface 153, wherein the average concentration $n_{av}$ is a root mean square average that is measured over the period of one (or more) modulation cycle(s) at the modulation frequency of generation beam 151. Concentration $n_{av}$ in turn indicates, under certain conditions as discussed below, a material property, e.g. the mobility of charge carriers in doped region 130. Each intensity measurement is a measure of reflectance if the power of generation beam 151 is unity (e.g. 1 watt).

Figure 1B:
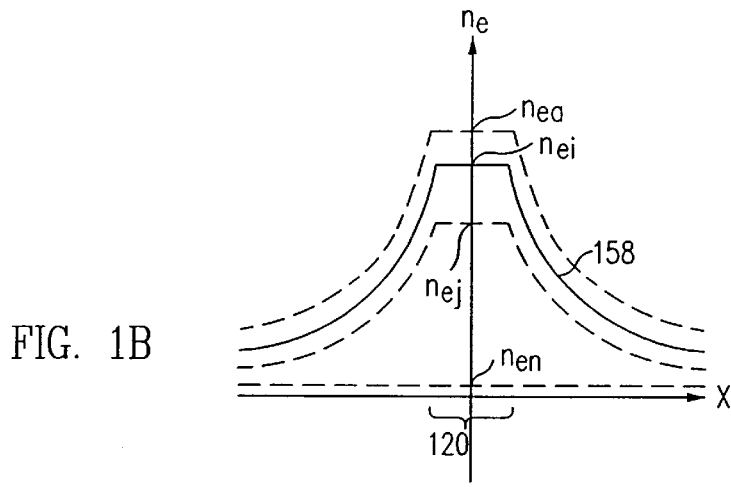
FIG. 1B illustrates, in a graph, the temporal modulation of charge carriers by the active dopant profiler of FIG. 1A, without creation of a wave, in a critical aspect of one embodiment.
Figure 1C:
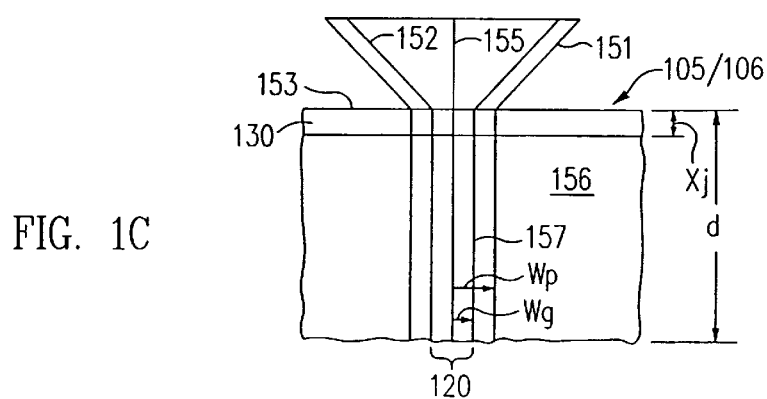
FIG. 1C illustrates, in a cross-sectional view, use of a probe beam and a generation beam, each beam focused coincident with the other by the active dopant profiler of FIG. 1A.

Although in FIG. 1C, beams 151 and 152 are illustrated as being coincident, with a common axis 155, in another embodiment, one of the beams, e.g. probe beam 152, is displaced with respect to the other beam to obtain an intensity measurement, e.g. location of generation beam 151 is changed on performance of one variant of act 244 (FIG. 2A). So beams 151 and 152 are separated each from the other as illustrated by a non-zero distance Δx between the respective axes 162 and 161 in FIG. 1F.

An intensity measurement obtained in such an offset position (FIG. 1F) of probe beam 152 with respect to generation beam 151 is used to measure various properties of the semiconductor material in doped region 130 a manner similar to the measurements obtained from coincident beams (FIG. 1C). The measurement obtained in the offset position (FIG. 1F) provides a measure of carrier concentration, because the concentration decays with distance d from illuminated region 120. Determination of lifetime from an intensity measurement in the offset position and another intensity measurement in the coincident position (FIG. 1C) is described below in reference to FIG. 7B.

In another embodiment, probe beam 152 is larger in diameter than generation beam 151 (as illustrated in FIG.

1H) due either to the difference in wavelengths of beams 151 and 152 or to properties of the beams such as the diameter and angle of divergence from a central axis. Specifically, probe beam 152 has a longer wavelength than generation beam 151, to ensure that the rate (also called "generation rate") of generation of carriers due to probe beam 152 is significantly less than the generation rate due to generation beam 151.

As the diameter of a beam generated by a lens scales linearly with wavelength, when both beams 151 and 152 use lenses of the same diameter, the diameter of probe beam 152 at surface 153 is larger than the diameter of generation beam 151 as illustrated in FIG. 1C. The just-described larger diameter of probe beam 152 simplifies the alignment required to fully overlay generation beam 151 with probe beam 152, as compared to the alignment of beams having the same diameter.

In one embodiment, the diameter of probe beam 152 is made larger (see act 244 in FIG. 2A) than that required to obtain the above-described difference in the rate of carrier generation, e.g. 2 to 50 times the diameter of generation beam 151. As the diameter of probe beam 152 is increased, the reflected portion of probe beam 152 becomes more sensitive to the radial decay of carrier concentration 158 outside illuminated region 120, as shown in FIG. 1B. According to one aspect of the invention, the change in the rate of decay provides a measure of the degradation of carrier lifetime, as described below in reference to FIGS. 7A and 7B. Examples of intensity measurements generated with such a configuration of beams 151 and 152 are illustrated by points 502A–502N in FIG. 5A.

In one implementation, probe beam 152 has an initial diameter Dp that is approximately the same diameter Dl of lens 815 (described below in reference to FIG. 8A), and generation beam 151 has an initial diameter Dg that is sufficiently large to ensure that radius Wg (FIG. 1C) of generation beam 151 at surface 153 is larger than (or approximately equal to) the radius Wp of probe beam 152 (at surface 153).

In another embodiment, probe beam 152 has a diameter that is smaller than or equal to the diameter of generation beam 151 and is used to eliminate the effect of lifetime variations on the measurements of mobility and doping concentration (as described herein). The smaller size of probe beam 152 is achieved (as illustrated in FIG. 1C) by enlarging the diameter and/or the divergence angle of generation beam 151, e.g. by moving a lens used to generate beam 151.

Instead of changing a parameter used in the intensity measurements (as described above in reference to act 244), profiler 103 can change a parameter used in the creation of charge carriers in illuminated region 120 (see act 147 in FIG. 2A) to obtain a number of intensity measurements (see act 243). For example, profiler 103 can change the rate of carrier generation in region 120 by changing either the power of generation beam 151 (while holding all other parameters constant), or the diameter of generation beam 151 (while holding other parameters, e.g. power) constant, as described below in reference to FIG. 7A. Alternatively, profiler 103 can change the location of illuminated region 120 and perform a number of intensity measurements.

Profiler 103 can also change both parameters, namely the parameter used in creating the charge carriers as well as the parameter used in measuring the concentration of charge carriers (e.g. by performing each of acts 241 and 244), as would be evident to a person skilled in semiconductor physics in view of the disclosure. In one implementation discussed below in reference to FIG. 2C, the locations of each of probe beam 152 and generation beam 151 are changed to obtain a linear scan across a wafer 104/105/106, while holding the beams 151 and 152 coincident each with the other.

Although in the above-described embodiments, a probe beam 152 having photons of energy below the bandgap energy of wafer 156 is used (to avoid the creation of measurement-related carriers during the measurement), in another embodiment a small percentage of charge carriers in addition to the charge carriers created by generation beam 151 are created by use of a probe beam 152 (same reference numeral is used for convenience) having photons of energy at or slightly above the bandgap energy. The measurement-related carriers created by such a probe beam 152 are in a sufficiently small percentage (e.g. an order of magnitude smaller than the number created by the generating beam) to provide a reasonably accurate measurement of reflectance (e.g. to within 5%). Note that the overall accuracy of a measurement as described herein is also governed by other inaccuracies involved in the act of measuring, e.g. inaccuracies in a measurement device, such as an amplitude detector 818.

Therefore, in one embodiment the inaccuracy caused by the measurement-related carriers is kept only as small as necessary to maintain the overall accuracy below a predetermined limit. Specifically, the percentage of measurement-related carriers is kept sufficiently small when the rate per unit volume of the carriers generated by generation beam 151 (obtained by dividing the photon flux per unit area by the absorption length), is at least one order of magnitude (or more) larger than for probe beam 152.

The photon flux per unit area described above is the number of photons per unit energy obtained by dividing the power P of generation beam 151 by the area ($\pi W_0^2$) of illumination by Plank's constant h and the ratio of the speed c of light to the wavelength $\lambda$ as shown in the following formula: photon flux=$(P/\pi W_0^2)$ $(1/h(c/\lambda))$. The absorption length is the depth from surface 153 at which the intensity of generation beam 151 drops to (1/e) of the intensity at surface 153 (see equation 23).

In one implementation, the intensities of beams 151 and 152 are kept approximately equal (e.g. 100 milliwatts per cm$^2$), and the number of charge carriers (also called "measurement-related carriers") created by beam 152 is less than 10% of the number of charge carriers (also called "excess carriers") that are created by generation beam 151 due to the difference in absorption lengths. Instead of intensities, the powers of beams 151 and 152 can be kept identical in case of an undoped layer of a wafer 104 because the dependence of carrier concentration on the diameter of beams 151 and 152 drops out as described below in reference to equation (5).

Note that in other implementations, beams 151 and 152 can have powers different from each other (e.g. 100 milliwatts and 25 milliwatts respectively), and yet maintain the number of measurement-related carriers at a negligible percentage. For example, probe beam 152 can have photons of energy greater than the bandgap energy, if the power of probe beam 152 is sufficiently less than the power of generation beam 151 (to keep the measurement-related carriers at a negligible percentage).

In one implementation, probe beam 152 has a generation rate one or more orders of magnitude smaller than the generation rate of generation beam 151. As noted above, the difference in generation rates is obtained by using beams 151 and 152 that have different absorption lengths in the semiconductor material of wafer 156, or by generating beams 151 and 152 at different powers or different diameters, or all of the above. In various implementations, the pair of beams 151 and 152 are generated by one of the following pairs of lasers: (AlGas, InGaAs), (Ar, InGaAs), (NdiYAG, InGaAs), and (NdiYAG, AlGaAs).

In one or more of the implementations, e.g. for use of lasers (NdiYAG, AlGaAs), the power of probe beam's laser (e.g. AlGaAs) is maintained less than the power of generation beam's laser (e.g. NdiYAG) because the absorption length of the probe beam is a fraction (e.g. one-tenth) of the absorption length of the generation beam. In another example, a probe beam 152 formed by a HeNe laser is maintained at a power less than or equal to $\frac{1}{4}_{th}$ power of generation beam 151 formed by an Ar laser (having an absorption length 1.2 $\mu$m that is $\frac{1}{4}^{th}$ the 3.0 $\mu$m length of the HeNe laser beam). In the just-described implementation, the power of the reflected portion of probe beam 152 is maintained large enough (by having a sufficiently large power of probe beam 152) to be detected with sufficient accuracy (e.g. with error of 5% or less) required for reflectance measurements as described herein.

In one variant of this implementation, the difference between the generation rates of beams 151 and 152 is one order of magnitude only at surface 153 (FIG. 1C). In a second variant, the order of magnitude difference is maintained throughout junction depth "Xj" of doped region 130 in wafer 105/106, e.g. throughout depth of 0.3 microns. In a third variant, the order of magnitude difference is maintained throughout a predetermined fraction (e.g. ½) of the junction depth xj.

In one embodiment, the above-described intensity measurement obtained in act 243 is used directly to detect electrically active defects that could lie at various depths d near (e.g. within 1–2 $\mu$m) surface 153 (FIG. 1C) in wafer 105. Specifically variations in intensity measurements across a wafer 105/106 are detected by changing (as illustrated by act 247 in FIG. 2A) the region 130 illuminated by beams 151 and 152, and repeating the measurement in the new region. Note that beams 151 and 152 remain coincident (as illustrated in FIG. 1C and unlike FIG. 1D) when focused on the new region.

In a first embodiment, (also called "scanning embodiment"), the measured intensity is plotted (in a graph) along the y axis, as a function of position along the x axis (see FIG. 3A), in response to movement of coincident beams 151 and 152 across wafer 105/106, to determine if wafer 105/106 is within the specifications (as illustrated by act 260 in FIG. 2A). In one implementation, computer 103C displays on a monitor 103M (FIG. 1A) various graphs for either a linear scan (as illustrated in FIG. 3A) or an area scan (as illustrated in FIG. 3B).

Specifically, lines 370, 380 and 390 in FIG. 3A illustrate the measured intensity in microvolts as a function of position in microns, over a 20 micron movement of the following wafers (not shown): (1) a first wafer that has not been patterned generates line 380 that is used to characterize rapid thermal anneals, (2) a second wafer that was pre-amorphized with a high energy silicon implant (e.g. a uniform dose of $5 \times 10^{14}$ silicon atoms per square centimeter at an energy of 100 Kev to cause uniform damage, and annealed at 1000° C. for 10 seconds to remove sub-surface defects) generates line 370, and (3) a third wafer having a uniform epitaxial region (e.g. grown with a thickness of 4 microns and a doping concentration of $1 \times 10^{15}$ boron atoms per cubic centimeter) generates line 390.

As seen from FIG. 3A, the intensity measurement varies as a function of the expected defect level. The empirical data in FIG. 3A is explained below in reference to equation (12a). Specifically, the carrier concentration (indicated by an intensity measurement) drops when the lifetime drops due to a defect in a wafer 104 that does not have a junction. The analysis for a wafer 105/106 having a junction is similar, although requiring a more complicated analytical solution. Instead of such an analytical solution, a numerical model is prepared, in one implementation using Atlas software in computer 103C as described below.

Specifically, the defect level is expected to be highest on the first wafer (see line 380 in FIG. 3A), because the first wafer is the lowest quality wafer among the just-described three wafers. Line 380 has the largest variation (as compared to lines 370 and 390), with defects at each of valleys 380A–380P (where $A \leq I \leq P$, P being the number of valleys, in this example P=8).

The second wafer with an annealed silicon implant is expected (due to the anneal) to have less defects, and as illustrated by line 370 has less variation than line 380 and fewer valleys 310A–310P (where P=5 in this example). The lowest defect level is expected in the third wafer since an epitaxial wafer includes a pure silicon crystal layer at the surface, so that the surface has no residual polishing damage. As illustrated by line 390, small sized (e.g. with a dimension <100 Å) defects near (within a depth of 1–2 $\mu$m from surface 153 in FIG. 1C) have electrical activity (wherein such defects act as sites for charge carriers of opposite polarity to recombine, thus reducing the lifetime) that causes a small variation (as illustrated in FIG. 3A) in the intensity measurements.

In one implementation, a ratio (also referred to as "peak-valley" ratio) is determined by dividing the signal value at a peak (i.e. a local maximum, e.g. peak 372 having a signal value of Sh1) by the signal value at a valley (i.e. a local minimum, e.g. valley 370A having a signal value of Sl1), to obtain a ratio e.g. Sh1/Sl1 for line 370 (and similarly ratio Sh2/Sl2 for line 380 and ratio Sh3/Sl3 for line 390). Thereafter, the ratios for wafers undergoing the same fabrication process, if smaller than or equal to a predetermined ratio identify acceptable wafers. For example, if ratio (Sh1/Sl1) of wafer 105/106 is greater than the predetermined ratio (Shm/Slm) as illustrated in FIG. 3A, wafer 1015/106 is identified as unacceptable (e.g. by placing in a bin of rejected wafers).

In one implementation, computer 103C displays on monitor 103M a message indicating that measurements identify a wafer 104/105/106 as unacceptable, while in another implementation computer 103C drives a signal to a robot (not shown) to move wafer 104/105/106 into a bin of rejected wafers (if rejected). The acceptable wafers are processed further in the normal manner (see act 262 in FIG. 2A).

A predetermined ratio (Shm/Slm) is set empirically by comparing the above-described ratios of one or more reference wafers (wherein the reference wafers are known to be good or bad based on electrical tests for conformance to the specification for such wafers), hereby to identify a maximum limit on the ratio for acceptable wafers. The empirical method used can be any method such as one of the methods described in "STATISTICAL QUALITY CONTROL HANDBOOK" available from AT&T Technologies, Commercial Sales Clerk, Select Code 700–444, P.O. Box 19901, Indianapolis, Ind. 46219, phone 1-800-432-6600, second edition, 1958.

Specifically, the variations in such a peak-valley ratio are correlated with the performance of a reference wafer during electrical tests that identify reference wafers (that are good). In one example, four different wafers have 1%, 5%, 10% and 20% variation from the peak-valley ratio Sh3/Sl3 (e.g. ratio 1.2) of an epitaxial wafer, and have the respective variations in performance speed of 8%, 10%, 20% and 25% during electrical testing of integrated circuit dies formed from the respective wafers.

Assuming that 10% and greater variation in speed is unacceptable, the predetermined ratio is set for this example at 5% variation. Therefore, all wafers having variation of peak-valley ratio lower than 5% are identified as acceptable wafers (as illustrated by act 262 in FIG. 2A). Note that if the peak-valley ratios of a number of wafers that have been successively processed are close to the predetermined ratio (e.g. all greater than 4.5% in the just-described example), one or more parameters used in processing the wafers may be adjusted (e.g. as described herein in reference to act 263 of FIG. 2A) even though none of the wafers are discarded.

In another implementation, instead of computing a ratio and comparing the ratio to a predetermined limit, difference (also called "measured difference") Sh1–Sl1 between local maximum 372 and local minimum 371, is compared directly with a predetermined limit Shm–Slm on such a difference, and the number of times the measured difference (over a unit distance) exceeds the predetermined limit is used as an indication of the number of defects in the wafer. The number of defects in wafers that have been annealed are detected (e.g. as valleys 380A–380P in FIG. 3A), and compared with a predetermined limit (e.g. 0 defects)on the number of defects, to accept or reject a wafer. In one implementation, computer 103C displays a message indicating the number of defects on monitor 103M.

In still another implementation, each measured intensity for a wafer 104/105/106 is compared with a predetermined range (e.g. the range Shm–Slm in FIG. 3A), and if any intensity falls outside the range, the wafer is rejected. Therefore in one example, if two wafers represented by lines 380 and 390 are formed by the same process, the wafer represented by line 380 is rejected and the wafer represented by line 390 is accepted.

Moreover, defects in an annealed wafer 106 cause changes in the shape of a plot of the measured intensity vs. power of the generation beam (see FIG. 3A described below). Therefore, in one embodiment, after identifying the locations of defects (e.g. the x-coordinate of each valley 380A–380N in FIG. 3A), a number of intensity measurements are performed at each location, and used to obtain a material property or process condition at the location.

Such material properties are of interest in the processing of wafers because of the sensitivity of reflectance measurements as described herein to the removal or creation of defects by processes such as annealing. Specifically, when the above-described act 240 (FIG. 2A) is performed on a wafer 104 before processing in wafer processing unit 101 (FIG. 1A), defective wafers are screened out at the beginning, i.e. prior to any processing as described herein (e.g. formation of doped regions), thereby eliminating two types of defects: (1) defects in a wafer caused by polishing and (2) defects in epitaxial material. Moreover, when act 240 is performed on a wafer 105/106, any defects caused by a fabrication process (e.g. ion implantation, annealing, etching or patterning) is identified (as described herein).

In addition, act 240 is used in one implementation to screen out starting wafers formed of bare silicon. When defects in such bare silicon are identified at the beginning, the method results in correction of the wafer fabrication process to ensure a sufficiently low defect level and eliminate the cost and use of a starting wafer 106 formed of epitaxial material. Starting wafers formed of pure silicon (also called "prime wafers") are processed by profiler 103 in a manner identical to starting wafer 104 as described herein.

Anneals are typically done by heating the wafer rapidly with lamps (not shown) in annealer 102 (FIG. 1A). The illumination by the lamps in annealer 102 may not be uniform, and the amount of heat that enters a patterned wafer 105 at any point may be a function of the thickness of dielectric layers (such as silicon dioxide or silicon nitride to be formed on surface 153), and the integrated circuit pattern therein. Specifically, the different layers (not shown) in wafer 105 reflect different amounts of power, thereby causing variations in the amount of heating of wafer 105.

Thus annealing of implanted wafer 105 may not be uniform, and the characteristics of a junction (formed at an interface between doped region 130 and semiconductor material 156 in FIG. 1C at a depth xj from surface 153 ) in annealed wafer 106 may vary from point-to-point. Lines 370, 380 and 390 (FIG. 3A) indicate to a person skilled in semiconductor physics the variations in junction properties on a micron and sub-micron scale. Therefore, such lines are used by a human operator of profiler 103 to check if the just-formed transistors are uniform all across wafer 105/106, and to conform to specifications (e.g. by adjusting the anneal, implant or circuitry design) the transistors in a to-be-formed wafer.

Instead of a human operator, such checking is automated by computer 103C in another embodiment. For example, instead of forming a display (as shown in FIGS. 3A and 3B), computer 103C (1) automatically uses the measurements of each wafer to compute the mean and standard deviation values, over a large number of wafers (typically several hundred or more), and (2) automatically uses these values of mean and standard deviation to identify when an implant or anneal process is out of specification, using statistical process control methods that generate control parameters (as described in pages 5–30 of the above-referenced book from AT&T Technologies, and these pages are incorporated by reference herein) to be provided to unit 101 or annealer 102.

As noted above, although a linear scan is illustrated in FIG. 3A, an area scan is performed in another embodiment as illustrated in FIG. 3B. Specifically, profiler 103 (FIG. 1A) performs a number of reflectance measurements in a corresponding number of regions (e.g. by repeating acts 244 and 243 in FIG. 2A) in a closely spaced grid (e.g. a grid that divides a wafer 105/106 into a number of regions, each region having an area 10 microns by 10 microns). The reflectance measurements are plotted to form on monitor 103M (FIG. 1A) a graph of the measured intensity vs. x–y position (e.g. in the form of various types of hatched regions as shown in FIG. 3B or preferably as a three dimensional image). Thereafter the graph of the area scan is used by an engineer skilled in semiconductor physics to evaluate wafer 105/106, in a manner similar to the the use of a scanning electron microscope.

Instead of plotting a graph to be manually checked, the reflectance measurements are checked automatically in another implementation, using statistical process control methods as described above. also, each reflectance measurement obtained by act 243 (FIG. 2A) provides an indication of a material property (e.g. the mobility of charge carriers) in wafer 105/106 (FIG. 1A). Specifically, profiler 103 is programmed to obtain a number of measurements (in at least one region 301) that are used (as described below in reference to FIGS. 5A–5H) to calibrate a measurement with respect to the material property (e.g. obtain a sealing factor to convert a reflectance measurement into doping concentration or a slope from a number of measurements into mobility).

In one implementation, profiler 103 performs a group of measurements (e.g. at least two measurements for two different powers of generation beam 151) in each region of wafer 105/106. Therefore in the just-described embodiment, profiler 103 functions as a scanning mobility microscope that displays on monitor 103M the mobility of various regions on wafer 104/105/106, and can be used in a manner similar to the use of a scanning electron microscope. In one example, four hundred measurements are taken in an area of 100 $\mu$m×100 $\mu$m and displayed in a three dimensional graph wherein the x and y axes define, in the two dimensions, a region on patterned wafer 105, and the hatch pattern (that is displayed on monitor 103M in a third dimension) indicates the measured reflectance.

In another embodiment, the location at which the charge carriers are created is not changed between two or more measurements. Instead, in performing act 241 (FIG. 2A), profiler 103 (FIG. 1A) creates charge carriers in the same location, and changes a parameter used to create the charge carriers. The parameter can be, for example, the average carrier concentration nav in region 120. Concentration nav is changed e.g. by changing the intensity of generation beam 151 (e.g. by changing the power or the diameter), as described below in reference to FIG. 5A.

Also, instead of or in addition to act 241, profiler 103 changes a parameter used in the measurement as illustrated by act 244 in FIG. 2A, e.g. changes the diameter of probe beam 152 or changes the location at which the reflectance is measured by offsetting the position of beam 152 relative to beam 151, as described above in reference to FIG. 1F.

Figure 4A:
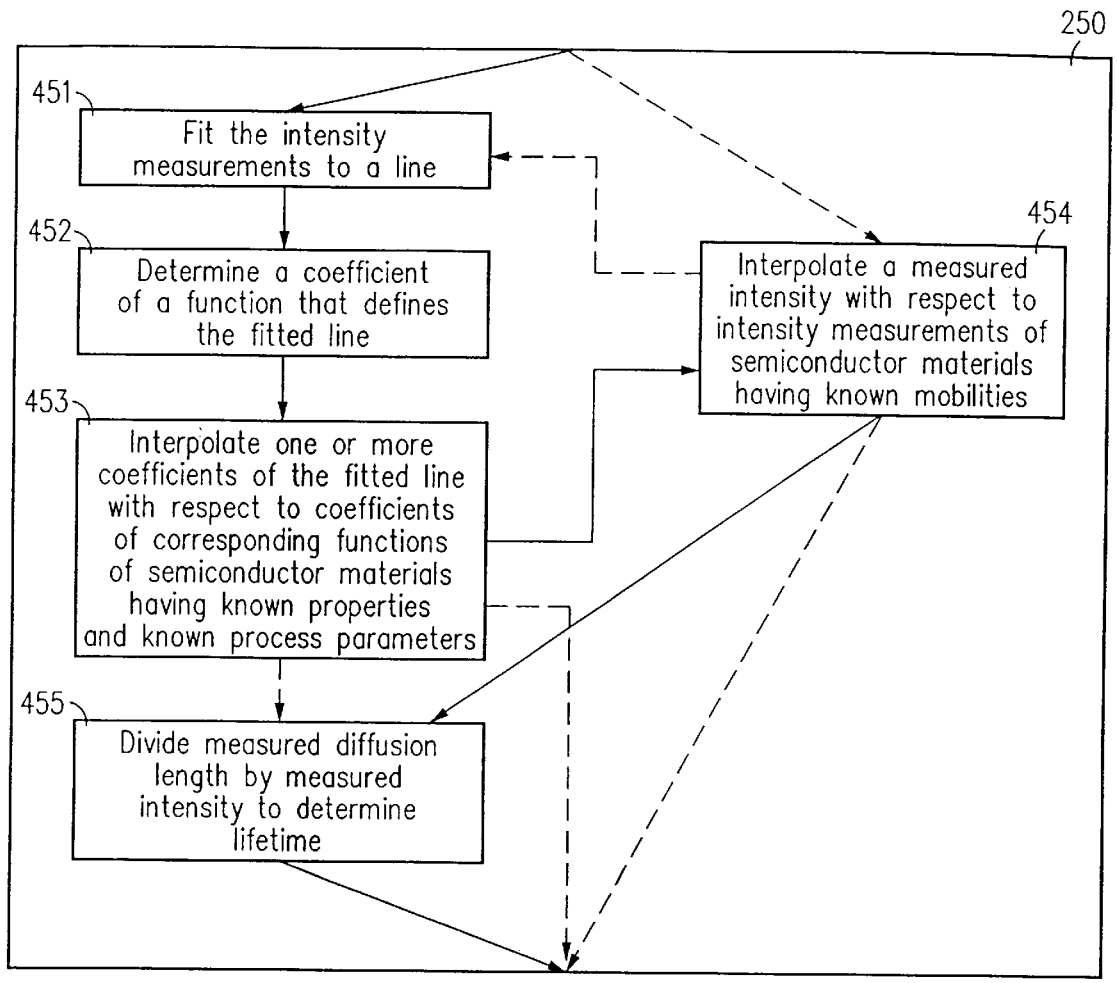
FIG. 4A illustrates, in a flow chart, acts performed on intensity measurements (by the profiler of FIG. 1A) to determine a material property or a process condition during fabrication of the wafer.
Figure 4B:
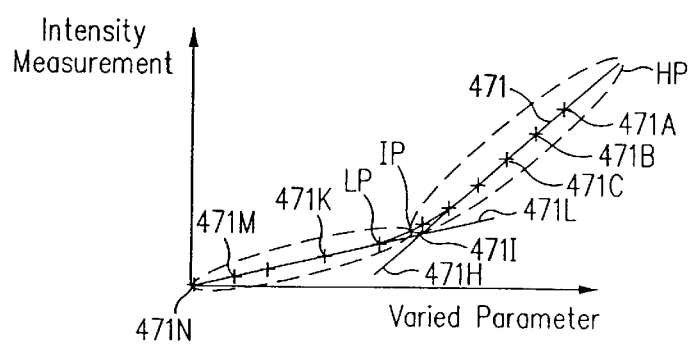
FIG. 4B illustrates, in a graph, intensity measurements as a function of a parameter (e.g. generation beam's power) that is varied to obtain the measurement, and fitting of the intensity measurements to two straight lines 471L and 471H to obtain coefficients (e.g. slope and intercept) used in measuring semiconductor material properties and process conditions.

In one embodiment, two or more of the reflectance measurements made in act 243 (FIG. 2A) are used to measure a material property of wafer 104/105/106 by one or more acts 451–455 (FIG. 4). Specifically, in act 451, profiler 103 fits the reflectance measurements to a line, such as curved line 471 (FIG. 4B). Curved line 471 is a plot (along the y axis) of the intensity of probe beam 152 (FIG. 1C) after reflection by region 120, as a function of the parameter being varied (along the x axis), e.g. power of generation beam 151 incident on region 120. Profiler 103 (FIG. 1A) uses points 471A–471N obtained by each of the intensity measurements to fit a curved line 471 (FIG. 4B) for a wafer (e.g. by connecting points 471A–471N with line segments).

Next, in act 252 (FIG. 4A), profiler 103 determines one or more attributes that describe curved line 471, e.g., determines the first order coefficient (also called "slope") and the zeroth order coefficient (also called "intercept") of one or more straight lines that approximate various portions (e.g. two portions described below) of curved line 471, and/or determines an inflection point (e.g. a point at which a second or higher order derivative becomes zero). In the example illustrated in FIG. 4B, curved line 471 has a point (hereinafter "inflection point") at which the slope changes in such a manner as to allow a majority (greater than 50%) of the intensity measurements greater than the measurement at inflection point IP to be approximated by a straight line 471H. Similarly, a majority of the intensity measurements below the measurement at inflection point IP are approximated by another straight line 471L.

So curved line 471 has a high-power portion HP that corresponds to a condition called "high level injection" wherein the concentration of excess carriers created by generation beam 151 (FIG. 1C) is greater than the concentration of background charge carrier normally present in doped region 130 due to activated dopants. Line 471 also has a the low power portion LP that represents a condition called "low level injection" wherein for powers of generation beam 151 lower than powers in portion HP, the rate of generation of excess carriers in doped region 130 is smaller than the concentration of background charge carriers due to the activated dopants. Low power portion LP and high power portion HP are each separated from the other by the just-described inflection point IP.

Lines 471H and 471L are obtained by computer 103C (FIG. 1A) without knowledge of inflection point IP by using two or more of the intensity measurements at the extreme ends of the range of measurements. For example, two points 471A and 471B that represent the highest intensity measurement and the next highest intensity measurement can be used to determine line 471H, while two other measurements 471N and 471M that represent the lowest intensity measurement and the next lowest intensity measurement are used (by computer 103C) to determine line 471L. Instead of using two points, in another embodiment three adjacent points at the high end of the range, e.g. points 471A–471C, are used to obtain a best fit line 471H, while three adjacent points 471K–471N at the low end of the range are used to obtain the best fit line 471L. In one implementation, inflection point 471I is found from the just-described lines 471L and 471H, as the point on curve line 471 that is the closest to an intersection point of lines 471L and 471H.

Figure 5A:
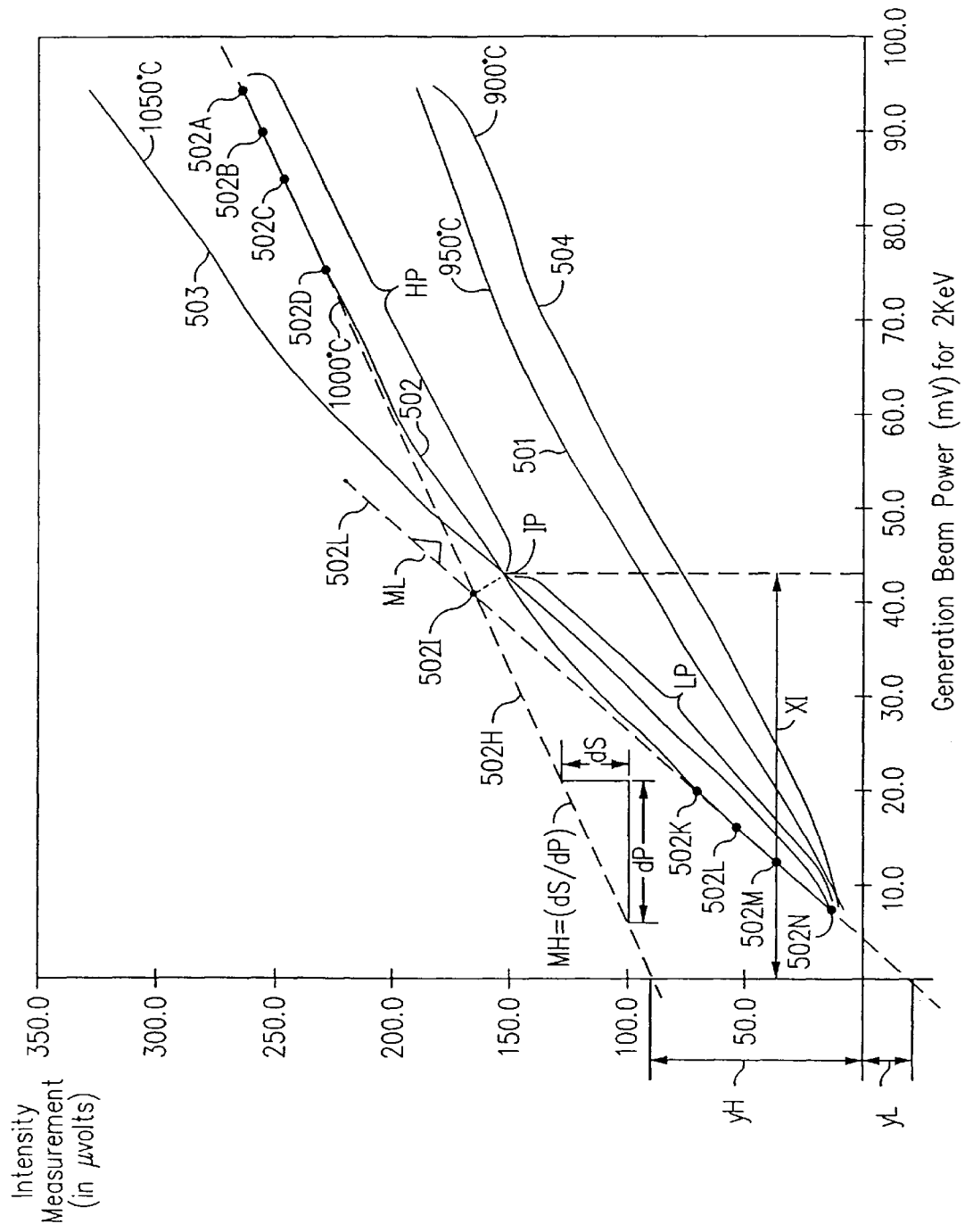
FIG. 5A illustrates, in a graph, intensity measurements plotted on the y axis as a function of the power of generation beam 151 (FIG. 1C) at the source plotted along the x axis for wafers annealed at four different temperatures.
Figure 7A:
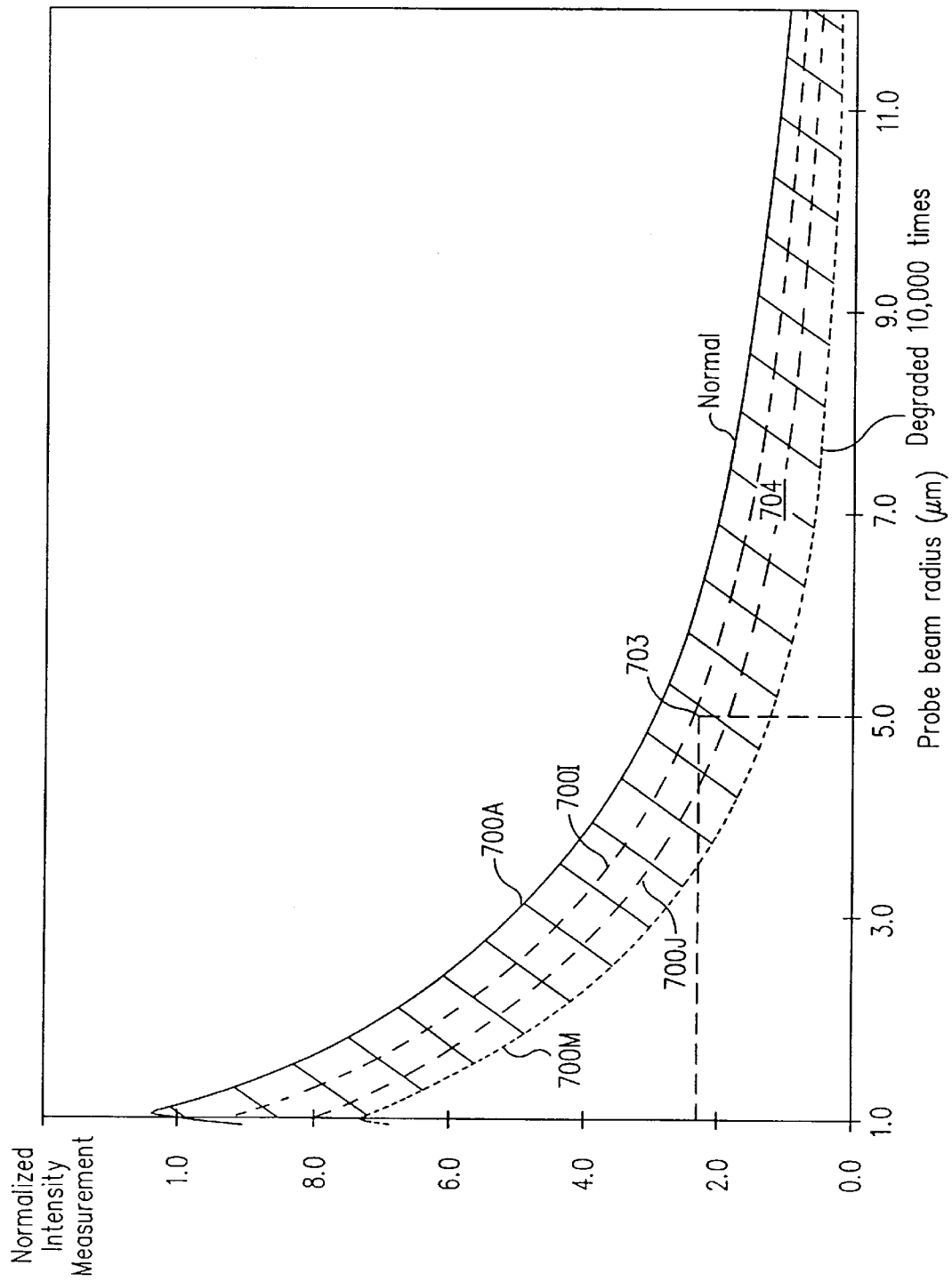
FIG. 7A illustrates in a graph, a normalized intensity measurement plotted along the y axis as a function of the radius of the probe beam (in $\mu$m) plotted along the x axis for material with normal lifetime, and degraded lifetime.
Figure 7B:
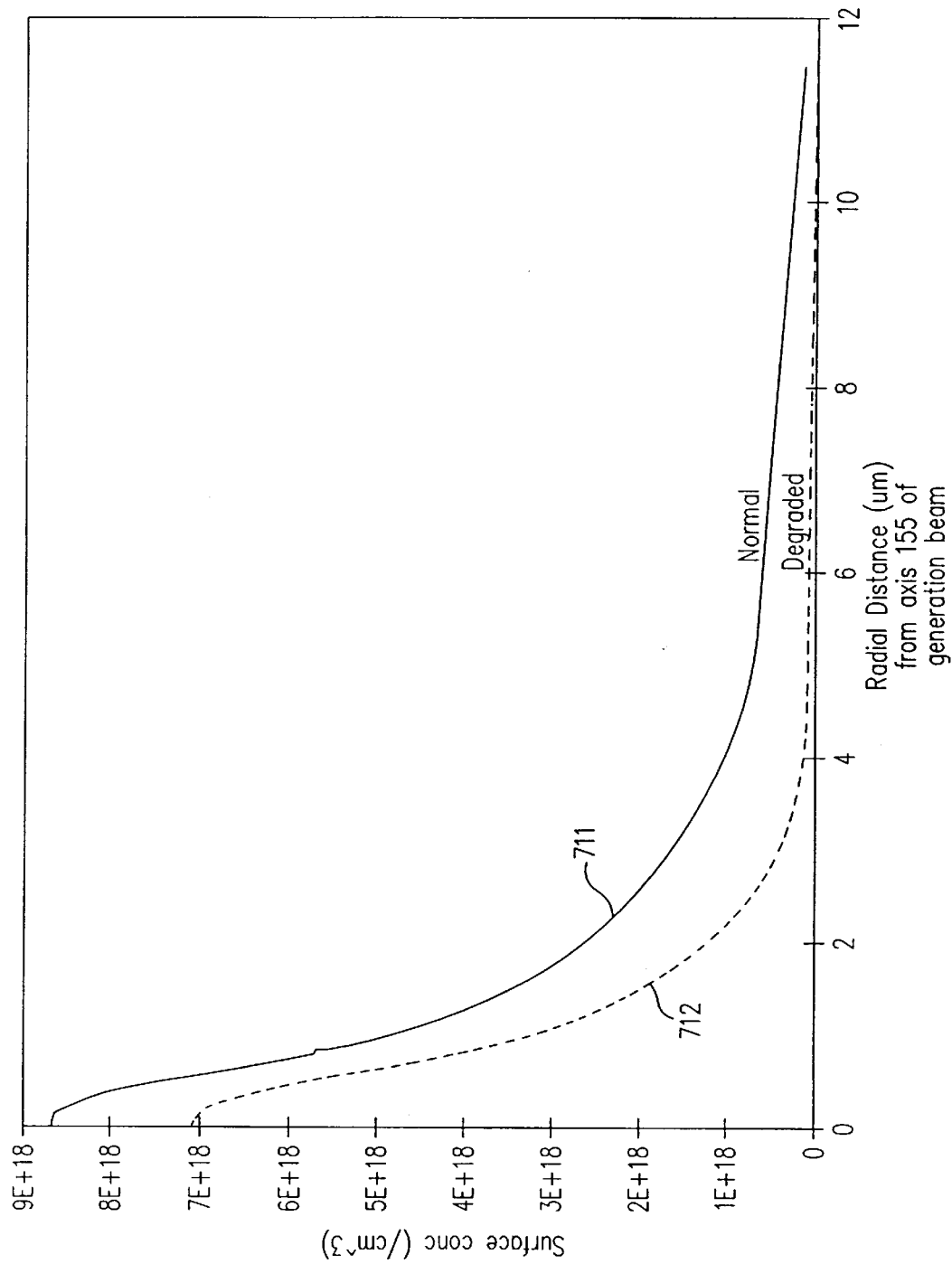
FIG. 7B illustrates, in a graph, the concentration per unit volume (at wafer surface 153 in FIG. 1C, and called "surface concentration") of the excess carriers plotted along the y axis as a function of the distance from axis 155 (FIG. 1C) of generation beam 151 plotted along the x axis for two materials: one with normal lifetime and the other with degraded lifetime (degraded by a factor of 10,000).

As noted above, in FIG. 4B the parameter varied in act 244 or act 247 (FIG. 2A) is plotted along the x axis. Therefore, depending on the implementation, the intensity measurement (see y axis) is plotted against one of the following: the power of generation beam 151 (as illustrated in FIG. 5A), the parameter of probe beam 152 (as illustrated in FIG. 7A), and the offset distance between beams 151 and 152 (as illustrated in FIG. 7B).

Although a pair of straight lines 471L and 471H are used to approximate curved line 471 in one implementation, other implementations use other numbers of straight lines (e.g. a single straight line for the entire curved line 471, or three or more straight lines). In alternative implementations, instead of using straight lines, computer 103C uses quadratic or higher order functions that approximate curved line 471, e.g. to obtain three or more such coefficients.

In one implementation, programmed computer 103C generates a number of curved lines 501–504 (FIG. 5A) from intensity measurements on four different wafers. For example, profiler 103 obtains a number of measurements 502A–502N with beams 151 and 152 coincident in the same region 120 (FIG. 1C) by changing the power of the generation beam 151. Thereafter, computer 103C generates lines 502H and 502L in the manner described above in reference to FIG. 4B, and thereafter determines the respective slopes $m_H$ and $m_L$, and the respective y intercepts YH and YL by performing acts 246A and 246B (FIG. 4A). In the just-described example, wafers represented by lines 501, 502, and 503 have known material properties, while the properties of a wafer represented by line 502 are unknown.

In one implementation, the properties and process conditions of wafers represented by lines 501, 502 and 503 are plotted as functions of one or more of the above-described coefficients, e.g. high power intercept YH and low power slope $m_L$, as illustrated by FIGS. 5B, 5C, 5D and 5E. Thereafter, the corresponding coefficients of line 502 are used to look up the respective properties and/or processing conditions.

Specifically, in the example illustrated in FIG. 5A, curved lines 501–504 have the following fit coefficients shown in Table 1.

TABLE 1

| Line | $m_L$ | $m_H$ | YL | YH | Anneal Temperature in Degrees Centigrade |
|---|---|---|---|---|---|
| 501 | 2.70 | 1.88 | −13.9 | 20.6 | 950 |
| 502 | 4.05 | 1.89 | −12.5 | 89.1 | 1000 |
| 503 | 4.13 | 2.92 | −25.7 | 51.8 | 1050 |
| 504 | 1.94 | 2.52 | −6.8 | −49.5 | 900 |

Figure 5C:
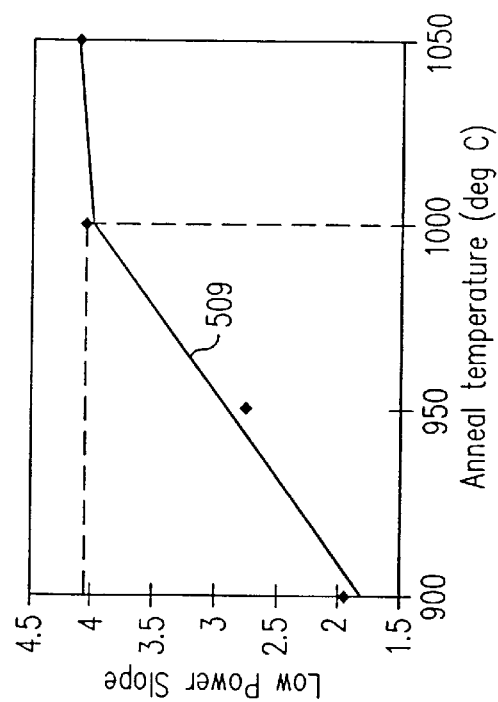
FIGS. 5B and 5C illustrate, in graphs, the variation of fit coefficients (specifically the high power intercept and the low power slope obtained from FIG. 5A) as a function of the temperature at which the wafer was annealed plotted along the x axis.
Figure 5B:
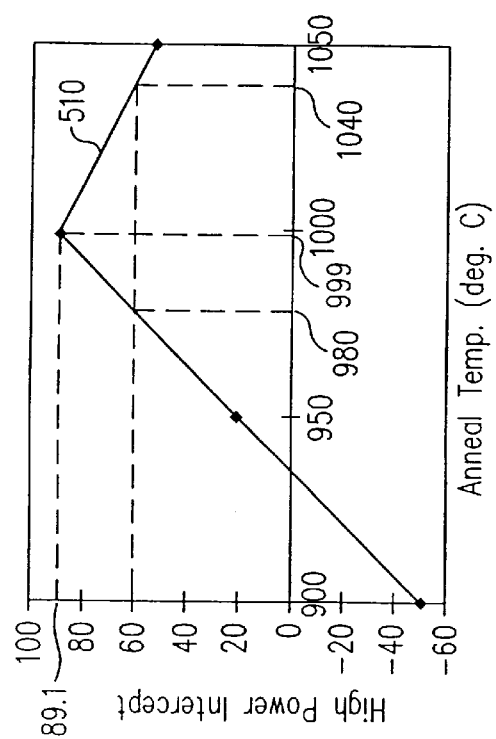

Therefore, computer 103C uses the high power intercept YH of value 89.1 as illustrated in FIG. 5B to obtain the anneal temperature as 999° C. from line 510 that is obtained from the known anneal temperatures of each of wafers represented by lines 501, 503 and 504. Similarly, computer 103C uses the low power slope $m_L$ of value 4.05 in FIG. 5C to obtain an anneal temperature of 1000° C. from line 309 again obtained from the known anneal temperatures. Although each of FIGS. 5B and 5C provide the same information for the wafer represented by line 302, i.e. an anneal temperature of around 999.5° C. (average of the two measurements obtained from FIGS. 5B and 5C), FIG. 5C is useful when FIG. 5B provides ambiguous information, e.g. indicates two anneal temperatures of 980° C. and 1040° C. when high power intercept is 60. The low power slope can be used to pick one of the two values 980° C. and 1040° C., e.g. pick 980° C. when the low power slope is less than 4.0.

In the above-described example of the wafer represented by curve line 302, programmed computer 103C compares the measured value of 999.5° C. with the specification of 975° C. (as illustrated by act 260 in FIG. 2A), and identifies the wafer as being rejected (e.g. by moving the wafer into a bin of rejected wafers), and thereafter adjusts a process parameter e.g. drives a signal on line 108 (FIG. 1A) to reduce the temperature by 25° C.

Instead of, or in addition to determining a process condition (e.g. anneal temperature as described above in reference to FIGS. 5B and 5C), the above-described attributes derived from the intensity measurements can be used to determine one or more properties of the semiconductor material in illuminated region 120. Specifically, profiler 103 uses the low power slope $m_L$ to determine junction depth Xj (FIG. 1C) by looking up a graph (FIG. 5D) of such slopes plotted against junction depth of wafers having known properties. In the above-described example, the low power slope mL has a value of 4.05, and line 511 (FIG. 5D) yields a junction depth of 580 angstroms.

Thereafter, profiler 103 compares the value of 580 angstroms with a predetermined range of acceptable junction depths e.g. the range of 400 to 600 angstroms. As the value of 580 falls within the range, wafer 105/106 is identified as acceptable, and is processed further in the normal manner (as illustrated by act 262 in FIG. 2A). If the measured junction depth falls outside the predetermined range, wafer 105/106 is rejected (as illustrated by act 260 in FIG. 2A), and one or more process conditions are adjusted e.g. by adjusting the addition of dopants (as illustrated in act 263).

Note that the adjustment of a process condition can also be performed even when a wafer is accepted (as illustrated by act 262), e.g. if the measured property (such as the junction depth) falls closed to the limits of the range, e.g. within 5 percent of the limit (in the above-described example within the range of 400–408, or within the range of 475–500). As noted above, to adjust the process condition, profiler 103 provides a signal to either or both of unit 101 and annealer 202 to return the value of the measured property back to the middle of the predetermined range (e.g. to 500 angstroms).

Measuring junction depths as described above in reference to FIG. 5D provides an unexpected result, considering that at least one prior art reference, namely U.S. Pat. No. 4,854,710 granted to Opsal teaches that depth information cannot be obtained in the absence of a plasma wave (specifically, Opsal states in column 4, lines 33–35, "[h]owever, in applications where sample variations as a function of depth need to be studied, it is necessary to generate and study plasma waves").

Similarly, profiler 103 uses another attribute, specifically the high power intercept YH to look up the concentration of active dopants at surface 153 (FIG. 1C). Specifically, profiler 103 uses the high power intercept YH of value 89.1 to obtain a surface concentration of $7 \times 10^{19}$ atoms/cm from line 512 (FIG. 5E) formed by plotting the high power intercepts of a number of wafers having known surface concentrations.

Instead of, or in addition to the use of a coefficient (e.g. one of the above-described slopes or intercepts to measure the concentration of dopants at the surface (as discussed above in reference to FIG. 5E), profiler 103 can use another attribute of curved line 502, specifically an inflection point IP of line 502 at which the second or higher order differential close to zero. Specifically, in one implementation, profiler 103 uses the x coordinate XI of the inflection point IP to determine the power of generation beam 151 and uses another graph (FIG. 5F) to look up the concentration of active dopants in material 156 (FIG. 1C).

Curved line 514 (FIG. 5F) is used directly with the generation beam's power at the inflection point IP as determined from FIG. 5A to look up the doping concentration. For example, when the value of the x coordinate of the inflection point IP is 43, curve line 154 yields a value of $7 \times 10^{19}$ atoms/cm$^3$ value for the doping. Line 514 (FIG. 5F) is obtained by programming the Atlas software into computer 103C to form a simulator as described herein, and providing to the simulator information on the material structure (description of the doped layers) and generation beam 151 (description of diameter, power and wavelength), for various doping concentrations and various powers.

Sheet resistance Rs of region 130 (FIG. 1C) can also be determined from the high order slope $m_H$ of line 502 (FIG. 5A) from a plot of the slope versus the sheet resistance as illustrated in FIG. 5G. Specifically, profiler 103 normalizes the measured slope to the slope of a wafer having a step junction, a 0.2 micrometer deep doped region 130, doped with 20 KeV implant into N-type epi wafer at a dose of $1 \times 10^{15}$ atoms/cm$^3$, with a probe beam 152 having a diameter 2 micrometers and power 41.5 mW, and generation beam 151 having a diameter 2 $\mu$m, and power varied from 0 to 90 mW.

Therefore, in one implementation, line 381 (FIG. 5G) is obtained by modeling the sheet resistance Rs using a finite element simulator, such as computer 103C (FIG. 1A) programmed with the software "Atlas" available from Silvaco of Sunnyvale, Calif. Such a simulator is set up (in a manner apparent to the skilled engineer in view of the disclosure) to model the carrier concentration at surface 153 (FIG. 1C) of semiconductor material 156 in response to illumination by generation beam 151, thereby to determine according to the model, a reflectance that is normalized with respect to the reflectance obtained from a wafer having a step junction 0.2 micrometer deep, and doped with 20 KeV implants into n-type epi on an n-type wafer.

The normalized reflectance is plotted as a function of the sheet resistance Rs to yield line 516, and the measured values are scaled (by normalization) to yield line 515 (FIG. 5G) coincident with line 516. Sheet resistance Rs varies inversely with each of doping concentration (FIG. 5F), and with junction depth Xj (FIG. 5D). Therefore, the junction depth Xj is held constant, by implanting with a constant energy while varying the dosage and therefore the doping concentration to create a variation in sheet resistance Rs.

Figure 6B:
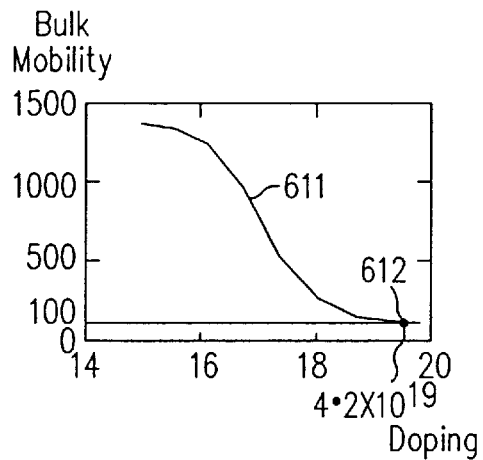
FIGS. 6B and 6C illustrate relationships known in the prior art for the bulk mobility and the bulk lifetime for use in one embodiment of profiler 103.

The slope $m_H$ of the high power portion HP (FIG. 4B) is proportional to inverse of the mobility, which is in turn proportional to doping concentration (as illustrated by the FIG. 6B). Therefore, the normalized high power slope $m_H$ (described above) is sensitive to the sheet resistance Rs, as demonstrated both by experiment and the simulator (and shown in FIG. 5G).

Profiler 103 extracts sheet resistance Rs as follows. Specifically, profiler 103 measures, for a wafer having a known sheet resistance Rs, a high power slope $m_H$ as described above (FIG. 5G) in the high power portion HP, e.g. such a reference wafer has sheet resistance of 500 ohms per square, thereby calibrating the slope value of 0.6. Thereafter, profiler 103 uses the calibrated value to plot the high power slopes against the sheet resistance, and obtain line 515.

Next, profiler 103 measures the reflected powers and determines a slope for a wafer with the same implant energy as the wafer having known properties used to calibrate lines 515 and 516. For example, the wafer with the unknown sheet resistance may have a slope of 0.8, and therefore profiler 103 determines the sheet resistance (from FIG. 5G) to be 1000 ohms/square.

For a step junction (a junction having one constant level of doping for depth values from the surface to the junction depth and a second constant level of doping for depth greater than the junction depth), the sheet resistance is given by $$R_s = \frac{\rho}{Xj} = \frac{1}{q\mu n Xj}$$

where $\rho$ is the resistivity, Xj is the junction depth, $\mu$ is the mobility, and n is the active carrier concentration. Thus, the sheet resistance Rs combines mobility, active doping concentration, and junction depth so that one of these can be determined from the others. For example, profiler 103 determines mobility using the above-described equation, after determining sheet resistance (from FIG. 5G), doping (from FIG. 5P) and junction depth (from FIG. 5D) as described above.

The high power slope $m_H$ of a plot of intensity measurements as a function of the power of generation beam 151 (e.g. lines 501–504 in FIG. 5A) is used to obtain mobility by simply dividing slope (for high injection) with a corresponding slope of a reference wafer and multiplying by the known mobility as shown by the formula:

$$\mu_{unk} = \frac{m_{ref}}{m_{unk}} \mu_{ref}$$

Specifically, for high-level injection, the current is radial as described below in reference to FIG. 9B. Therefore, the carrier concentration is given by equation (5) that is also described below. Combining equations (5), (21) and (22) described below gives the high power slope $$m_H = \frac{q^3(1-R_0)\alpha}{2\pi(m_0^2-1)\varepsilon_0\varepsilon_s m^* \omega^2 kTE_{ph}}\left(\frac{1}{\mu}\right)$$

where $m_H$ is the slope of the high power portion of the line obtained by plotting along the y axis the reflection signal normalized to the absolute reflection as a function of the generation beam 151's power plotted along the x axis, q is the electron charge, $R_0$ is the absolute reflection, $\alpha$ is the absorption coefficient, equal to the inverse of the absorption length $m_0$ is the index of refraction of the silicon, $\varepsilon_s$ and $\varepsilon_0$ are the dielectric constants of free space and the silicon, $m_e$ is the carrier effective mass, $\omega$ is the radial frequency of the probe beam, k is Boltzmann's constant, T is the temperature, and $E_{ph}$ is the energy of one photon at the generation beam wavelength, and $\mu$ is the mobility.

A curve such as line 517 (FIG. 5H) is found from the above equation. In more complex situations, line 517 can be found by numerical modeling. Line 517 also can be found empirically by measuring $m_H$ and correlating to mobilities measured, for example, by constructing transistors on the same material and measuring the mobility based on the performance characteristics of the transistor. Thereafter, profiler 103 uses the high power slope $m_H$ of a wafer under fabrication to look up mobility using line 517.

Graphs, such as lines 509–513 in FIGS. 5B–5F, that are used to determine a material property or a process condition are generated in one of the two following ways (in two different embodiments). In the first embodiment, a set of wafers (also called "reference wafers") is selected or prepared to have a range of material properties (by varying process conditions, such as implant energy, dose or anneal temperature), and thereafter profiler 103 is used to obtain intensity measurements and generate fit coefficients or other attributes for each of the reference wafers (as described above). Thereafter, the fit coefficients or attributes are used to plot lines 509–513 and 515. In a second embodiment, a number of wafers (also called "reference wafers") are subjected to intensity measurements in profiler 103 (as described above), followed by use of a conventional measurement technique, such as spreading resistance profiling to determine the actual doping profile therein.

In one example, lines 501–504 in FIG. 5A represent wafers created by ion implantation at an energy of 2 KeV and dosage of 1×10$^{15}$ using boron, followed by annealing at each of the following temperatures: 950° C. for line 501, 1000° C. for line 502, 1050° C. for line 503 and 900° C. for line 504. Thereafter, intensity measurements are obtained as described above, and plotted to form the graphs in FIG. 5A. Next, spreading resistance profiles (abbreviated as "SRP") are prepared, as illustrated in FIG. 6A, wherein the reference numerals obtained by adding 100 to the reference numerals in FIG. 5A indicate lines corresponding to the same wafers (e.g. line 501 in FIG. 5A corresponds to line 601 in FIG. 6A).

SRP lines 601–604 illustrated in FIG. 6A, are prepared by breaking the wafers to expose the ion-implanted layer followed by beveled edging and probing to measure the profile of the concentration of active dopants as a function of depth. Therefore, at the end of the preparation of SRP, the graphs (FIG. 6A) provide a plot of the active dopant concentration (atoms/cm$^3$) along the y axis as a function of depth (in microns) along the x axis. From lines 601–604, programmed computer 103C determines the surface concentrations 601Y–604Y, that are thereafter used to generate line 512 illustrated in FIG. 5E. Moreover, programmed computer 103C determines the depths at the dopant concentration value of $1\times10^{19}$, specifically x coordinates of points 601J–604J, and uses these values to generate a plot of low power slope versus junction depth illustrated as line 511 in FIG. 5D. Straight lines generated by the above-described methods fit (in an act called "curve-fitting") the measurements well, e.g. $R^2$ values of greater than 0.95 in FIGS. 5D and 5E.

Therefore, after one or more of the above-described graphs (see FIGS. 5B–5G) are prepared, the material properties of a wafer under fabrication are determined by the above-described method 200 (FIG. 2A) without the need to break and lap the wafer, because profiler 103 simply uses the above-described graphs to generate measurements of material properties. Therefore, profiler 103 eliminates the cost associated with test wafers otherwise required by the prior art methods (for breaking and lapping).

Although in the above description, computer 103C has been described as performing various computations for preparation of lines (e.g. line 512 in FIG. 5E) used to measure material properties, such graphs can be prepared by another computer, or alternatively can be prepared manually by performing the above-described acts.

Moreover, although in one embodiment the above-described lines (e.g. FIGS. 5A–5G) are prepared, in another embodiment such graphs are not prepared and instead the reflectance measurements are simply used to perform the various acts of method 200 by use of equations related to such graphs. For example, instead of drawing a line 512 (FIG. 5E), the slope and intercept of such a line are determined, and thereafter an equation containing the slope and intercept is used with the high power intercept to obtain the surface concentration.

Also, instead of line 512 being a straight line, a curved line can be used, and alternatively, a second or higher order differential equation can be fitted to the intensity measurements to obtain the property measurement (in the manner described herein, as would be apparent to a person skilled in the art of computer programming).

Figure 5E:
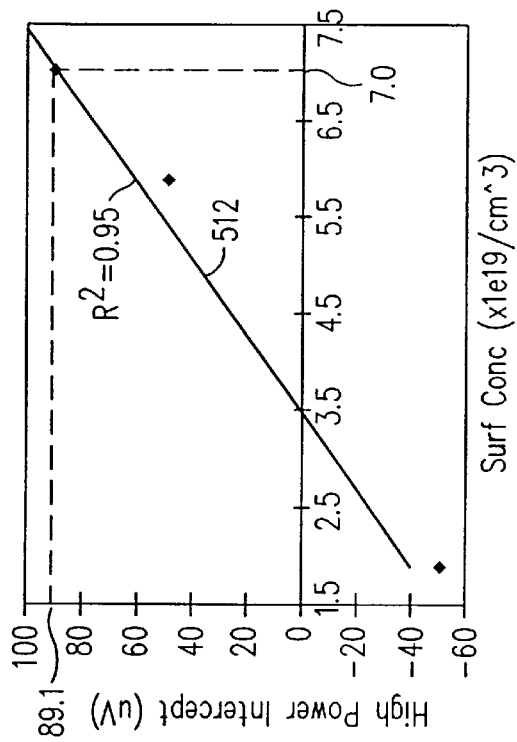
FIGS. 5D and 5E illustrate, in graphs, the just-described coefficients plotted along the y axis as a function of junction depth and surface concentration respectively.
Figure 5D:
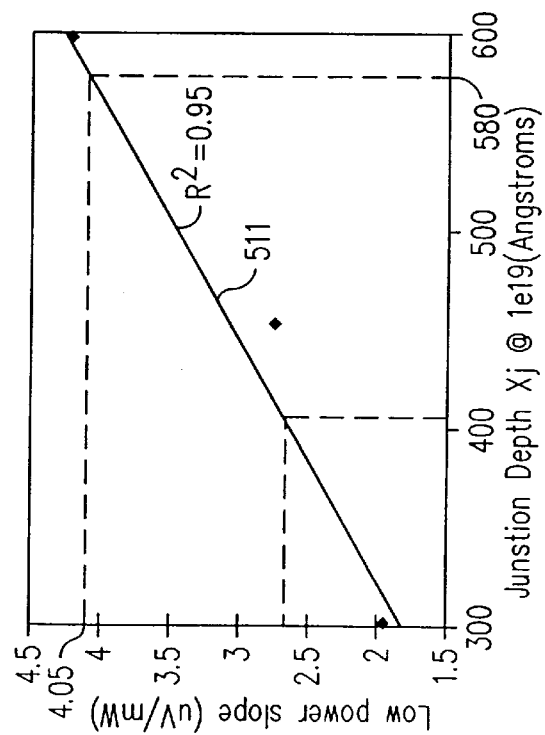
Figure 5H:
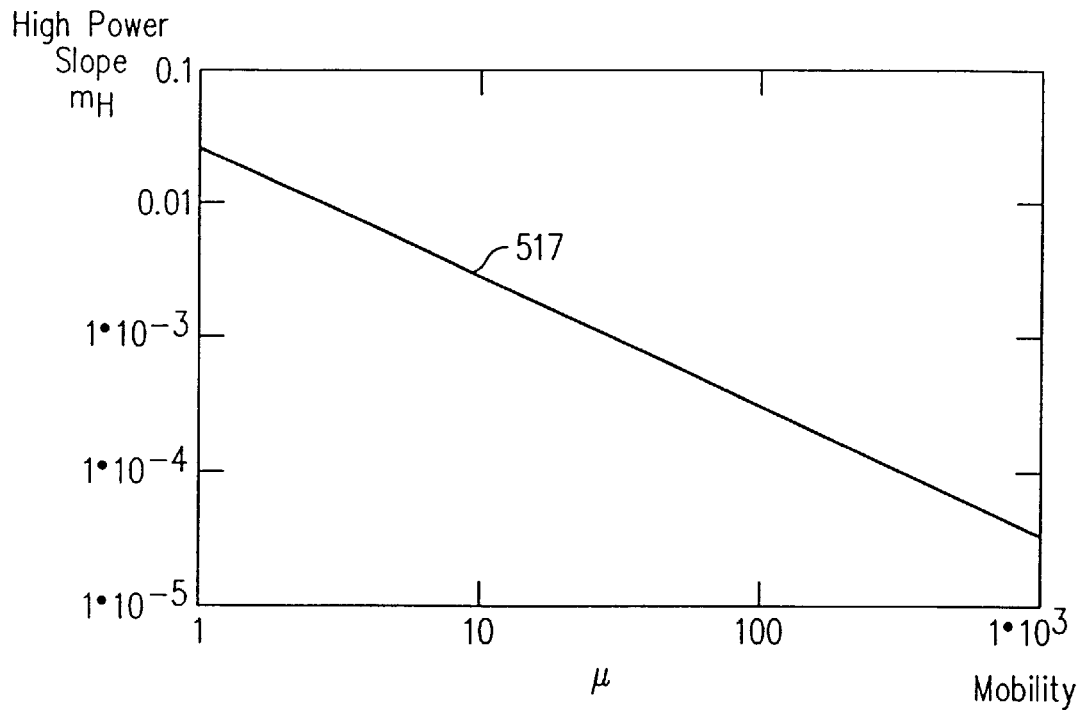

Furthermore, well known relationships, such as the relation of mobility to dopant concentration (as illustrated by line 611 in FIG. 6B) can be used in addition to (or instead of) the above-described graphs (in FIGS. 5B–5G). Specifically, in one embodiment, profiler 103 uses a line 611 (FIG. 6B) in the range of $10^{16}$ to $10^{19}/cm^3$, a range that is in common use in integrated circuit processing, to obtain mobility of the value 100 centimeters per second from a dopant concentration of $4.2\times10$ atoms/cm that is obtained as described above in reference to FIG. 5E. Note that although the surface concentration obtained from FIG. 5E is higher than the dopant concentration in the bulk, the mobility obtained from line 611 approximates the mobility in the bulk, because the mobility drops only slightly between $10^{19}$ and $10^{20}$ atoms/cm$^3$ dopings, as described below in reference to FIG. 9C.

Figure 6C:
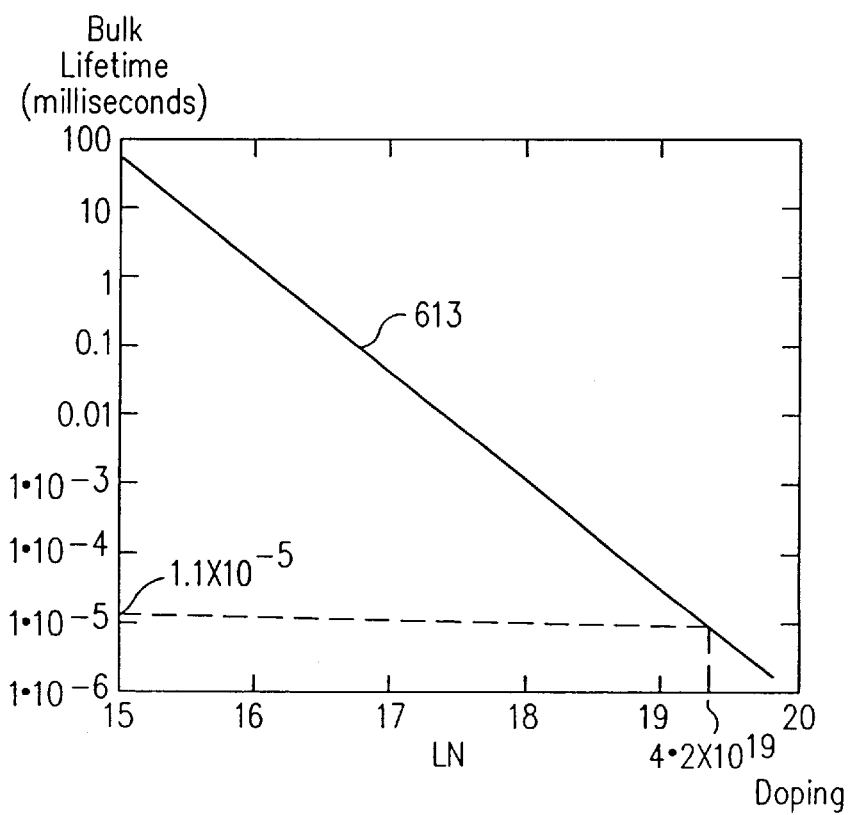

Another well known relationship, illustrated by line 613 (FIG. 6C) can be used to estimate the bulk lifetime from a knowledge of the dopant concentration as follows. Specifically, profiler 103 uses the dopant concentration e.g. of value $4.2\times10^{19}$ to lookup, from line 613, a bulk lifetime of value $11\times10^{-5}$ milliseconds. The surface dopant concentration provides an estimate of the lifetime in the bulk material 156 (FIG. 1C).

Instead of using the known relationships (e.g. lines 611 and 613 in the respective FIGS. 6B and 6C), relationships specific to the wafers being fabricated can also be prepared as described above in reference to FIG. 5H from the appropriate measurements of the mobility and lifetime using conventional methods, and these relationships are thereafter used in profiler 103 to measure the mobility and lifetime of a wafer under fabrication as described herein.

The above-described known relationships (such as the relationship between mobility and dopant concentration described above in reference to FIG. 6B) provides an accurate estimate only in the absence of effects (such as surface roughness and dopant segregation) that reduce mobility. Specifically, surface roughness causes scattering that degrades the value of surface mobility to a level below bulk mobility, so that the surface mobility that determines line 502 (FIG. 5A) may not be the same as the bulk mobility corresponding to the carrier concentration that determines inflection point IP (FIG. 5A).

Therefore, one embodiment uses two attributes together to obtain a property e.g. (1) uses inflection point IP (as described above in reference to FIG. 5F) to obtain dopant concentration, and (2) uses line 502 (specifically the high power intercept YH) to obtain surface concentration (as described in reference to FIG. 5E) to determine a change in the doping concentration (independent of surface roughness). Specifically, the inflection point indicates a condition when the concentration of excess carriers equals the doping concentration. For example, if the surface mobility is half the bulk value, then a doping concentration extracted from a mobility of 100, using point 612 indicates a value of $4\times10^{19}$, while a doping concentration extracted from the inflection point using FIG. 5F, indicates a value of $1\times10^{18}$.

Instead of changing the power of generation beam 151 between reflectance measurements to generate lines 501–504 (FIG. 5A), another parameter can be changed as illustrated by act 244 described above in reference to FIG. 2A. Specifically, in one implementation, the diameter of either probe beam 152 or generation beam 151 is changed between reflectance measurements, and therefore yields measurements that are sensitive to the rate $dn_{ei}/dx$ of carrier concentration 158 as shown in FIG. 1B. The change in rate $n_{ei}$ is used to measure degradation of carrier lifetime as illustrated in FIGS. 7A and 7B.

Figure 1H:
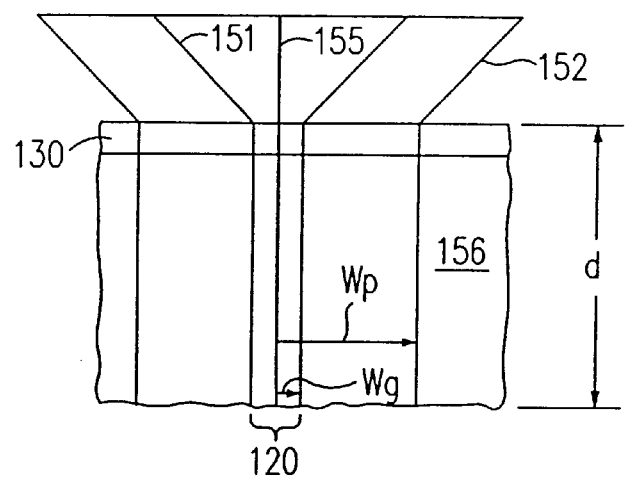
FIG. 1H illustrates, in a cross-sectional view, beams 151 and 152 of FIG. 1C wherein the diameter of probe beam 152 has been increased (e.g. by an order of magnitude) as compared to the diameter illustrated in FIG. 1C.

Specifically, lines 701 and 702 (FIG. 7A) illustrate limits of a range of acceptable lifetimes of a wafer under fabrication, and represent along the y axis the normalized intensity measurement, plotted against the radius of probe beam 152 (FIG. 1H). The intensity measurement illustrated in FIG. 7A is normalized to the intensity measurement obtained by use of a probe beam 152 of the diameter 1 micrometer for no degradation in the lifetime, on a wafer 105/106 having a step junction 0.2 micrometer deep, doped with a p-type dopant at a dosage of $5\times10^{18}$.

Therefore, profiler 103 simply plots point 703 in the graph of FIG. 7A from a measurement obtained for a wafer under fabrication, and checks to see if point 703 falls within a region 704 defined to be the acceptable region between limits 701 and 702. If so, profiler 103 decides that wafer 105/106 that generated measurement 703 has an acceptable lifetime. Note that the above-described measurement represented by point 703 is a single measurement, and therefore the single measurement is adequate to decide the acceptance or rejection of a wafer as described herein.

Moreover, in one implementation, a number of additional lines, e.g. lines 700I and 700J are included, and profiler 103 estimates the lifetime at point 703 by interpolation, e.g. to be 500 times degraded (because point 703 falls between line 700I for 100 times degradation and line 700J for 1000 times degradation). A plot of the normalized intensity measurement versus the probe beam diameter provides an accurate test for checking the lifetime of a wafer 105/106, because the intensity measurement is linearly proportional to the concentration of carriers generated by generation beam 151 at surface 153, as illustrated by lines 711 and 712 (FIG. 7B) corresponding to the above-described lines 701 and 702.

Note that in FIG. 7B, the x axis indicates radial distance from axis 155 (FIG. 1H) of generation beam 151. The relationship between intensity measurement and the surface concentration is described below in reference to equations 21 and 22. Note that in view of equations 21 and 22, instead of a reflectance measurement being used to measure a property of the semiconductor material, a change in the index of refraction can also be used in a similar manner.

In one implementation, beam 152 (FIG. 1C) is a laser beam having a wavelength greater than 1 $\mu$m (the wavelength at which photons have approximately the same energy as the bandgap energy of silicon). Note that the wavelength of beam 152 depends on the bandgap energy and therefore on the specific material in wafer 105/106, and is different for germanium.

In one example, probe beam 152 is generated by a laser 801 (FIG. 8A), such as a 1480 nm fiber coupled laser diode, model CQF756/D having a maximum output power of 70 milliwatts, available from Philips Corporation, Eindhoven, The Netherlands. Laser 801 is mounted separate from other components in profiler 103, and is coupled to a collimator 803 by a fiber 802 that carries beam 152. Collimator 803 can be, for example, part number WT-CY3-163-10B-0.5 available from Wave Optics, Mountain View, Calif.

In this implementation, generation beam 151 is created by an above bandgap laser 805, such as 830 nm laser diode model SDL-5432-H1 having a maximum output power of 200 milliwatts, available from Spectra Diode Labs, San Jose, Calif. Profiler 103 includes a lens 806, which is part number 06GLC002/810 available from Milles Griot Corporation, Irvine, Calif. Lens 806 collimates the generation beam 151, and is mounted on a positioner (not shown) for providing motion to beam 151 with respect to beam 152.

The relation between wavelengths of beams 151 and 152 produced by lasers 801 and 805 is a critical aspect in one embodiment and leads to unexpected results, for example when beam 151 contains photons having energy above silicon's bandgap energy and beam 152 contains photons having energy approximately the same as or less than the bandgap energy. In this example, for a silicon wafer the 830 nm and 1480 nm wavelength beams provide one or more benefits described herein (e.g. generate a negligible percentage of measurement-related carriers).

Profiler 103 also includes an isolator 807, such as part number OIM-12-812 available from Karl-Lambrecht Corp., of Chicago, Ill. Isolator 807 prevents back reflections from entering laser 805. Profiler 103 also includes a photo-diode 821a that is used to measure the intensity of beam 151 after reflection by wafer 106. Moreover, an anamorphic prism (not shown) is inserted in beam 151 to circularize beam 151 that is generated in a polarized manner by laser 805.

Profiler 103 also includes lenses 808 and 809 that function as 2× beam reducer, with focal lengths of 37.5 mm and 75 mm respectively. Lens 808 mounts on a stage (not shown) to allow adjustment of the position along the X-axis with respect to laser 805, and therefore can be used to de-collimate beam 151, thereby varying the spot size with respect to beam 152. Profiler 103 also includes partially transmissive mirror 810, such as a dichroic mirror that combines beams 151 and 152, thereby to create a combined beam 811. Diodes 821B and 821C are "reference diodes" that are used for absolute calibration of the transmitted and reflected power of a probe beam 152.

Profiler 103 also includes a photo cell 821b (such as a photo diode) that detects leakage through mirror 810, thereby measuring the forward power of beam 151. Beam 811 passes through 50:50 beam splitter 813, and 90:10 beam splitter 814 to objective lens 815. Objective lens 815 can be, for example, 100×, 0.9NA lens part number 81814 available from Nikon Corporation of Yokohama, Japan. Lens 815 focuses the combined beam 811 onto the surface of wafer 106.

Profiler 103 also includes photo cell (also called "photo diode") 821C that is used to measure the forward power in beam 811. Profiler 103 also includes stage 829 that is used to move wafer 106 relative to beam 812 in the X, Y and Z directions. Specifically, stage 829 can be moved in the vertical direction along the Z axis to adjust focus, and in a horizontal plane to adjust the position of region 120 of FIG 1B relative to beam 812 (also required by step 244 in FIG. 2A).

Beam 812, after reflection by region 120 passes back through objective lens 815 to 90:10 beam splitter 814. Splitter 814 deflects 10% or the return beam to second lens 819 that acts as a microscope eyepiece. Lens 819 has a magnification of, for example, 10×, such as part number 81845 from Nikon of Yokohama, Japan.

After passing through lens 819, the deflected portion of beam 812 is incident on a camera 820, such as model 85400 available from FJW Industries of Palatine, Ill. Lens 819 and camera 820 together form a microscope to allow the measurement of focus, beam size and beam overlay using a vision system, such as model ASP-6CR-11-S available from Cognex Corporation, Boston, Mass.

Ninety percent of the reflected portion of beam 812R passes to beam splitter 813 that diverts the reflected portion through filter 817, such as Schott glass RG830, available from Spindler & Hoyer Corporation of Goettingen, Germany to photo cell 818, such as J16-8SP-RO5M-HS from EG&G Judson of Montgomeryville, Pa, USA.

Filter 817 removes photons of generation beam 151 from combined beam 812R, thereby allowing detector 818 to see only the photons of probe beam 152. Filter 817 is a critical component in one embodiment and provides the unexpected result of eliminating feedthrough of the modulated signal (generated by beam 151) to detector 818 that would otherwise be present when using a prior art system of the type disclosed by Smith as discussed above. In this particular implementation, germanium is used in photo detector 818 to provide sensitivity to photons of wavelength 1480 nanometers that are generated by laser 801.

Profiler 103 includes signal processing circuit 830 and drive circuit 840 that are used respectively to process the reflected portion 812R and to generate the generation beam 151. Specifically, laser driver 842 (such as model 8000 from Newport Corporation of Irvine, Calif.) drives laser 805 to generate beam 151 in response to signal on modulation input terminal 842M. Laser driver 842 includes thermoelectric cooler power supply(not shown) to maintain the stability of laser diodes 805 and 801. Drive circuit 840 also includes reference oscillator 843, such as a bench variable frequency oscillator, that is used to drive a signal on modulation input terminal 842M. Reference oscillator 843 provides 100% modulation of beam 151. Reference oscillator 843 has a frequency that is set manually to a value in the range of 1 Hz to 20,000 Hz to avoid the creation of a wave of carriers in region 130 (FIG. 1C).

Combined beam 812 after reflection by region 120 is incident on photo cell 818 included in signal processing circuit 830. Photo cell 818 converts the power of the instant beam into a current that is supplied to current-to-voltage converter 833 also included in signal processing circuit 830. Converter 833 can be, for example, a single stage op-amp transimpedance amplifier using an OP-27A integrated circuit available from Burr-Brown of Tuscon, Ariz.

Converter 833 converts the current from photo cell 818 into a voltage that is provided to a single gain stage 834 also included in circuit 830. Gain stage 834 provides an additional signal gain over the gain provided by converter 833, because converter 833 is limited to a few kilohms. The gain in converter 833 is limited because converter 833 is dc coupled, and the power of reflected portion 812R is a few milliwatts, so that excess transimpedance gain will cause converter 833 to saturate.

Converter 833 is ac coupled to amplifier 834. In one embodiment, a constant component of the reflectance (as opposed to the reflectance component at the modulation frequency) is measured from the signal at a node 838 that is located between converter 833 and amplifier 834. Profiler 103 uses the constant component to normalize the intensity measurement, and compares the normalized measurement between wafers (e.g. between a wafer under fabrication and a reference wafer). The voltage signal provided by amplifier 834 is used by a lock-in amplifier 835, such as model 830 available from Stanford Research Systems, Sunnyvale, Calif. Lock-in amplifier 835 is coupled to reference oscillator 843 that provides a signal modulated at the same frequency as the signal on modulation terminal 842m of laser driver 842. Lock-in amplifier 835 provides a signal indicating the intensity of reflected portion 812R modulated at the frequency provided by oscillator 843 to processor 836, such as a personal computer running software to capture and display the signal in an appropriate manner.

In one implementation, personal computer 836 has a line 837 that is coupled to lines 107 and 108 (described above in reference to FIG. 1A) thereby to control the acts performed by ion implanter 101 and rapid thermal annealer 102 based on measurement of one or more material properties as described herein.

Mobility is a material property that affects current transport in semiconductors 156, and is defined through the following equation:

$$J = q\mu n E - \frac{kT}{q}\mu \frac{\partial n}{\partial x} \quad (1)$$

where J is the current density, n is the carrier concentration, E is the electric field, k is Boltzmann's constant, q is the electron charge, T is the temperature, and $\mu$ is the mobility. Appearing in both terms of equation (1), mobility $\mu$ is the fundamental material constant that defines the current flow (See Sze, "Physics of Semiconductor Devices", pages 50–51, incorporated by reference herein).

Mobility $\mu$ directly relates to fundamental device performance, including speed and power dissipation. For example, in a field effect transistor (the fundamental building block of modern integrated circuits) the transconductance $g_m$ (change of current with respect to applied gate voltage) is linearly proportional to the mobility through the factor $$g_m \propto \frac{Z}{L}\mu C_0 \quad (2)$$

where Z and L are the channel width and length respectively, and $C_0$ is the gate capacitance. The mobility near (e.g. within a depth less than the mean free path of the carriers) surface 153 (FIG. 1C) depends on a number of parameters affected by the process, such as surface roughness, doping and defect density (See Grove, "Physics and Technology of Semiconductor Devices", page 326, incorporated by reference herein).

Lifetime is a measure of how long a carrier exists before it recombines, and is determined from a measurement of the radial decay of the concentration of excess carriers as described herein (e.g. is reference to FIGS. 7A and 7B). Contamination causes the lifetime to drop rapidly, as does an increase in defect density. Thus, lifetime is a sensitive indicator of material quality and process contamination. Near the surface 153 (FIG. 1C), lifetime may be dominated by trapping centers at the interface between a silicon dioxide layer and the silicon. The lifetime near surface 153 becomes an indicator of the quality of this interface.

Active dopants modify the conduction properties of a semiconductor material 156 (FIG. 1C), thereby making devices such as transistors. Active dopants are also used to isolate devices, form contacts, and adjust operating voltage levels. Profiler 103 indicates how much of an implanted dose becomes electrically active and therefore the efficacy of such structures. In many cases, process problems relate to uniformity of the anneal and activation, so that measuring only an implanted dose in an unannealed wafer 105 is of less value than measuring in an annealed wafer 106 a profile of active dopants (e.g. lines 601–604 described above in reference to FIG. 6A).

The photons of beam 151 (FIG. 1C) generate free electron-hole pairs. Because the index of refraction of semiconductor material 156 is large compared to free space (silicon, for example, has a relative index of refraction of 3.42), the incident rays refract sharply to the normal 155, and the beam shape approximates a cylinder 157 for a depth of a few microns (e.g. 5 microns beneath the surface).

When the diffusion length L (the distance excess carriers travel before they recombine, given by $L^2=(kT/q)\mu\tau$, where $\tau$ is the lifetime and k is Boltzmann's constant, T the temperature, and q the electron charge) is long compared to the radius $w_0$ of illuminated region 120—as is commonly the case in some processes—the carrier concentration within this cylinder is independent of radius $w_0$, and varies as the inverse of the mobility, $\mu$. Furthermore, reflectance relates directly to the carrier concentration C, so that a reflected power measurement provides a direct measure of mobility $\mu$.

Outside the illuminated cylinder, carrier concentration C drops rapidly, the drop being approximately exponential function of the ratio r/L, where r is the radius from the cylinder and L is the diffusion length. Because of the cylindrical geometry, the drop off is a Bessel function, which is the cylindrical symmetry equivalent of an exponential function. Thus, knowledge of the mobility $\mu$ from an intensity measurement (see act 243 in FIG. 2A) within illuminated region 120 coupled with another intensity measurement of the carrier concentration as a function of distance from illuminated region 120 allows determination of lifetime $\tau$ as described above (in reference to FIGS. 7A and 7B).

Furthermore, in silicon of the type used to make semiconductor devices (such as integrated circuits), the concentration of active dopants directly relates to the mobility.

Thus, a measurement of the mobility allows determination of the active dopant concentrations 60Y–604Y (FIG. 6A). Finally, adding a layer of material with a concentration of dopants different from the bulk, as by ion implantation and annealing as described above, affects the reflectance as a function of the power of beam 151 (FIG. 1C), and the function can be used to determine the active dopant profile in the added layer.

Carrier concentrations in a bulk material (i.e. a material that is uniformly doped) can be calculated assuming that the diffusion length L is very long compared to the cylinder radius, i.e. ($D\tau >> w_0^2$) so that there is no recombination in the cylinder. In this formula D is the diffusion coefficient $D=(kT/q)\mu$, where $\mu$ is the mobility. Thus, the diffusion coefficient and the mobility are directly related. Furthermore, it is assumed that the absorption length $\alpha^{-1}$ of the beam 151 (FIG. 1C) used to generate carriers is long compared to the cylinder diameter $2w_0$, so that the generation is approximately constant in depth d.

Under these assumptions, all carriers generated in cylinder 157 exit out the side, and there is negligible current along the normal 155 that is the axis of the cylinder 157. This case usually applies, since the radius $w_0$ typically 0.5–3 $\mu$m, the diffusion length L may be 20 $\mu$m or longer, and the absorption length $\alpha^{-1}$ is 5–20 $\mu$m (the former for a wavelength $\lambda$ of 670 nanometers, the latter for a $\lambda$ wavelength of 810 nm).

The rate G of carrier generation per unit volume in a cylinder 157 of radius $w_0$ (also called "spot size") in a region between depth z and z+dz is $$G(r) = \pi r^2 (1-R)\Phi(e^{-\alpha z} - e^{-\alpha(z+dz)}) \approx \pi r^2 (1-R)\Phi \alpha e^{-\alpha z} dz, \quad (3)$$

where r is the distance from normal 155, R is the surface reflectance, F is the incident photon flux of beam 151, $w_0$ is the radius of cylinder 157, and $\alpha$ is the absorption coefficient of material 156.

The flux F out of a cylinder of radius r is this number G of carriers generated per unit time per unit volume found in equation (3), divided by the area of the wall of cylinder 157, $$F(r) = \frac{G}{2\pi r d z} = \frac{\alpha r (1-R)\Phi e^{-\alpha z}}{2} = -D\frac{\partial n}{\partial r} = -\frac{kT}{q}\mu\frac{\partial n_e}{\partial r}. \quad (4)$$

The last two equalities in equation (4) are due to the fact that the flux F is limited to diffusion (in the absence of a wave), and a relationship between the diffusion coefficient D and mobility $\mu$ is applied from an equation (6) to be discussed below.

This solution in equation (4) ignores surface recombination of charge carriers. One embodiment of the invention is used on semiconductor wafers undergoing integrated circuit processing, and these wafers usually have surface passivation, that suppresses surface recombination.

The carrier concentration in a cylinder is independent of the cylinder's radius under the conditions described herein as shown below. Integrating both sides of equation (4) with respect to r from zero to the cylinder radius gives $$n_e(w_0) = \int_0^{w_0} \frac{\partial n}{\partial r} dr \quad (5)$$

$$= \frac{q(1-R)\alpha e^{-\alpha z}}{4\pi k T \mu}(\pi w_0^2 \Phi)$$

$$= \left[\frac{q(1-R)\alpha e^{-\alpha z}}{4\pi k T E_p}\right]\left(\frac{1}{\mu}\right) P_1$$

where $P_1$ is the power of generation beam 151, $E_p$ is the energy of a single photon, and the mobility and diffusivity relate as $$D = \frac{kT}{q}\mu \quad (6)$$

where k, T and q have been described above in reference to diffusion length L. Equation (5) shows that when the spot size (also called "beam diameter") $w_0$ is small, excess carrier concentration $n_e$ in any cylinder is independent of radius, and is solely a function of known physical parameters (a constant shown in square brackets in equation (5)), and the inverse of mobility $\mu$.

Therefore, a measurement of intensity of probe beam 152 after reflection by the charge carriers anywhere in illuminated region 120 (FIG. 1C) on surface 153 of semiconductor material 156 provides a direct measure of mobility $\mu$ (scaled by the just-described constant) when power Pl of the generation beam 151 is 1 watt.

In one embodiment, the reflected intensity of beam 152 as a function of power of beam 151 is measured. As shown below, the reflected intensity varies linearly with carrier concentration $n_e$. Therefore, a plot of reflected intensity v/s generation beam power for a wafer without a doped layer at the surface, as shown by line 901 in FIG. 9A, approximates a straight line. The slope of line 801 is the product of known physical parameters and the inverse of the mobility.

Therefore, equation (5) illustrates the physical basis of the measurement of carrier concentration $n_e$ by profiler 103 within the illuminated region. The exact solution for the carrier concentration $n_e$ is found using the diffusion equation in cylindrical coordinates, $$\frac{\partial n_e}{\partial t} = G - \frac{n_e}{\tau_0} + D\left(\frac{\partial^2 n_e}{\partial r^2} + \frac{1}{r}\frac{\partial n_e}{\partial r}\right) \quad (7)$$

where $n_e$ is the concentration of excess carriers and G is the generation rate per unit volume, with $$G = \alpha\Phi \quad (8)$$

where, as above, $\Phi$ is the incident photon flux per unit area and $\alpha$ is the absorption coefficient.

For periodically varying incident radiation, all quantities vary in time as exp(j$\omega$t), and (7) reduces to $$\left(\frac{\partial^2 n_e}{\partial r^2} + \frac{1}{r}\frac{\partial n_e}{\partial r}\right) - n_e\left(\frac{1}{D\tau_0} + j\frac{\omega}{D}\right) + G = 0 \quad (9)$$

To avoid creation of a wave of charge carriers as described herein, the real part of the second term in equation (9) needs to be significantly larger than the imaginary part, a condition that requires the frequency $\omega = 2\pi f = 1/10\tau_0$. For a lifetime of 10 $\mu$sec, the modulation frequency f should be less than 1600 Hz. The imaginary part of equation (9) when significantly larger than the real part leads to a wave-like solution at high frequencies and is avoided under the conditions described herein. The present invention operates at sufficiently low frequencies, to allow the imaginary term to be dropped. This assumption reduces equation (9) to $$\rho^2 n''(\rho) + \rho n'(\rho) - \rho^2 n(\rho) = 0 \quad (10)$$

where $r^2 = r^2/D t_0 = r^2/L^2$ and $n = n_e - G\, t_0$.

The solution to equation (10) is written in terms of the hyperbolic Bessel functions of order zero, $$n\left(\frac{r}{L}\right) = A I_0\left(\frac{r}{L}\right) + B K_0\left(\frac{r}{L}\right) \quad (11)$$

where $K_0$ tends to zero at infinity and becomes infinite at zero. Conversely, $I_0$ diverges as r approaches infinity but tends to zero for small arguments. Consequently, within the cylinder 157 formed by beam 151 (FIG. 1C), A is finite and B is zero. Outside the cylinder, B is finite and A is zero. The coefficients A and B are found by recognizing that the carrier concentration C and its derivative are continuous at the cylinder wall, $r=w_0$.

Applying the above conditions gives the exact solutions as follows, where "n" is the carrier concentration that is in excess of the concentration with zero illumination:

$$n(r \leq w_0) = G\tau \left[1 + \frac{K_1\left(\frac{w_0}{L}\right) I_0\left(\frac{r}{L}\right)}{K_0\left(\frac{w_0}{L}\right) I_1\left(\frac{w_0}{L}\right) - I_0\left(\frac{w_0}{L}\right) K_1\left(\frac{w_0}{L}\right)}\right] \quad (12a)$$

and $$n(r \geq w_0) = G\tau I_1\left(\frac{w_0}{L}\right) \frac{K_0\left(\frac{r}{L}\right)}{K_0\left(\frac{w_0}{L}\right) I_1\left(\frac{w_0}{L}\right) - I_0\left(\frac{w_0}{L}\right) K_1\left(\frac{w_0}{L}\right)} \quad (12b)$$

Figure 9A:
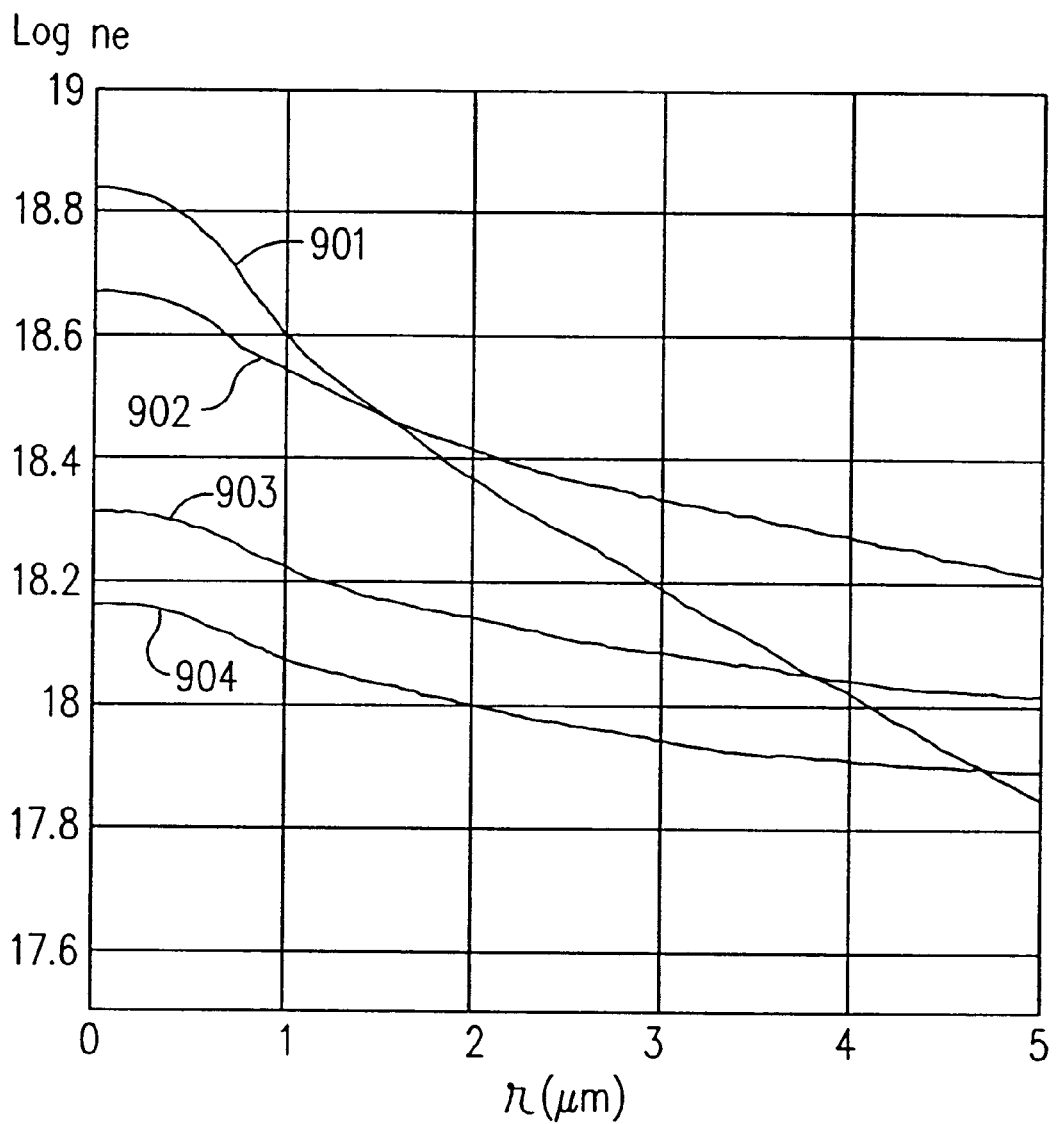
FIG. 9A illustrates, in a graph, a variation of the logarithm of the surface concentration plotted along the y axis as function of the radial distance (from the central axis 155 of generation beam 151 shown in FIG. 1C) plotted along the x axis, obtained by numerical modeling.
Figure 9B:
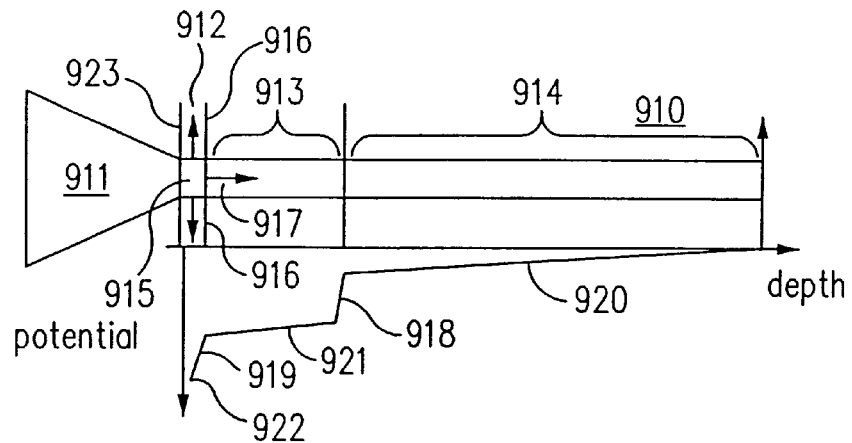
FIG. 9B illustrates, in a cross-sectional diagram, a beam incident on a semiconductor material having a layer of dopants in a concentration greater than the concentration of dopants in the bulk material, and superimposed thereon a graph of the potential distribution resulting from illumination by the beam.

FIG. 9A shows lines 901–904 that illustrate the solution inside equation (12a) and outside equation (12b) illuminated region 120. Equation (12a) yields the same result as equation (5) for $w_0 \ll L$. Specifically, FIG. 9A illustrates, in a graph, curved lines 901–904 that indicate the logarithm (along the y axis) of carrier concentration (for corresponding doping concentrations) as a function of the radial distance (along the x axis) from the central axis 155 (FIG. 1C), with no ion implants in the respective wafers. The doping concentrations for curved lines 901–904 are respectively $10^{19}$, $10^{18}$, $10^{17}$, and $10^{16}$ atoms/cm$^3$, and the measurements were taken about r=0, where beams 151 and 152 (FIG. 1C) overlay. As beam 151 is cylindrically symmetric, the linear coordinates (different from angular coordinates θ) are depth D and radius r.

In FIG. 9A, the carrier concentration (vertical axis) is shown as a function of radius near surface 153 (depth=0) resulting from illumination by an generation beam 151 (FIG. 1C) of uniform spatial intensity (e.g. assume a constant beam intensity for a radius between zero (the beam axis) and the beam radius $w_0$ (FIG. 1C), and zero intensity beyond the beam radius $w_0$). The beam radius $w_0$ in one example is 0.5 μm the power is 20 milliwatts, and the wavelength is 810 nanometers (for silicon).

As shown herein, the carrier concentration $n_e$ in region 120 (FIG. 1C) is constant, independent of beam radius $w_0$, and inversely proportional to the mobility of the charge carriers. The mobility is inversely proportional to the doping concentration, so the carrier concentration increases with doping. Also, the reflectance measurement increases linearly with the carrier concentration, and so the reflectance measurement provides a measure of 1/mobility.

The rate at which the concentration $n_e$ drops outside illuminated region 120 (FIG. 1C) is a function of the lifetime T and the diffusion length $L=(D\tau)^{1/2}$. Since D is known from the reflectance measurement within illuminated region 120, a set of reflectance measurements radially outward from the cylinder edge determines the lifetime τ.

Figure 9C:
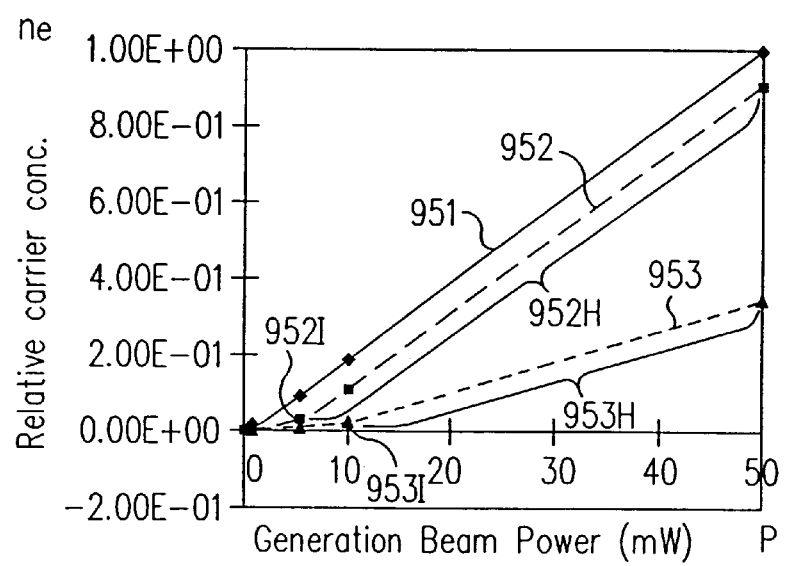
FIG. 9C illustrates, in graphs, carrier concentration ne plotted along y axis as a function (obtained by numerical modeling) of the power P of the generation beam plotted along x axis for different doping concentrations.

Carrier concentration $n_e$ can also be determined in material with a shallow doped layer 911 (FIG. 9B) formed by introduction of dopant atoms through surface 153. FIG. 9C illustrates a semiconductor structure in wafer 105/106 under illumination, the potential drop across the structure, and the currents out of the region of the shallow doped layer under illumination. Regions 912–914 are, respectively, a shallow doped layer, a low doped epitaxial layer, and a high doped substrate. All are assumed to be doped p-type, although n-type doping, or various combinations of n-and p-type doping give similar results. Junction 916 exists between shallow doped layer 912 and epitaxial layer 913.

The semiconductor surface 923 is illuminated with laser beam 911, creating a cylindrical region of illumination in the substrate, and illuminating region 915 of shallow doped layer 912. The illumination causes a potential drop across the structure, with the surface at the most negative point. Most of the potential drop is taken up at the interface between the epitaxial layer 913 and substrate 914, drop 918, and the interface between the shallow doped layer 912 and epitaxial layer 913, drop 919. Lesser drops occur in the substrate 914, epi layer 913, and shallow doped layer 912, which are drops 920, 921 and 922 respectively.

Two currents flow out of the shallow doped layer 913. One is a vertical current 917, flowing perpendicular to the surface. The second is a radial current 916, flowing parallel to the surface. These currents are assumed to be due to diffusion. There are four components: the vertical hole current, the vertical electron current, the radial hole current, and the radial electron current. These are, respectively:

$$J_{Vp} = -q D_p \frac{dp}{dz} \quad (13a)$$

$$J_{Vn} = q D_n \frac{dn}{dz} \quad (13b)$$

$$J_{Rp} = -q D_p \frac{dp}{dr} \quad (13c)$$

$$J_{Rn} = q D_n \frac{dn}{dr} \quad (13d)$$

where q is the electron charge, $D_p$ and $D_n$ are the hole and electron diffusion coefficients respectively, p is the hole concentration, n is the electron concentration, z is the variable in the depth direction, and r is the variable in the radial direction. $D_p$ and $D_n$ are related to the electron and hole mobilities as $D_{n(p)}=(kT/q)\mu_{n(p)}$, where k is Boltzmann's constant, T is the temperature, and $\mu_{n(p)}$ is the electron (hole) mobility.

A qualitative analysis (described below) of the structure shown in FIG. 9C explains how the surface carrier concentration, and, hence, the reflection signal, is a function of the power of generation beam 911. The qualitative analysis further explains how the curve may have inflection points and regions with differing slopes, as shown by line 471 in FIG. 4B (described above), and how material properties related to a profile of dopants in the shallow doped region 912 are extracted from curve 471.

Currents 916 and 917 are driven by the gradient of the carrier concentration, as shown in equations 13a–d above.

The gradient in the vertical direction scales as the carrier concentration divided by the junction depth. The gradient in the radial direction scales as the carrier concentration divided by the diffusion length in layer 912. Typically, the junction depth is 0.02–0.1 μm and the diffusion length is several microns, so at low level injection the vertical current dominates.

The carrier concentration at the surface is found by integrating current 917, given by equations 13a and 13b, from the surface 923 to the junction 916, with the boundary condition that the carrier concentration must be zero at junction 916 since, according to potential drop 919, junction 916 is reverse biased. This integral increases with junction depth. Therefore, the signal at low level injection is sensitive to junction depth. Experimental results, such as line 511 in FIG. 5D (described above), confirm this dependence.

Under high level injection, the effect of the background doping concentration disappears, and the potential drop 919 across the junction between regions 912 and 913 disappears. The gradient of the carrier concentration in the vertical direction is now due to the optical absorption of photons, a distance characterized by the absorption length. The gradient of the carrier concentration in the radial direction is still due to the diffusion length in layer 912.

For 830 nm radiation, the absorption length is about 20 μm. The radial gradient is on a scale of 2–4 μm (see, for example, the decay of the radial electron concentration lines 701 and 702 in FIG. 7A). Now, the radial current 916 is larger than the vertical current 917. The surface carrier concentration is sensitive to the near-surface mobility, and sensitivity to the junction depth disappears.

According to the above description, line 471 (FIG. 4B) when fit in the region below inflection point IP (FIG. 4B), corresponds to low level injection, as illustrated by straight line 471L, and to the region above inflection point 471I, by straight line 471H. The slope and intercept of line 471L are each used to characterize the junction depth and the slope and intercept of line 471H are each used to characterize the mobility near the surface. As the inflection point IP occurs at the transition from low to high level injection (as described above in reference to FIG. 4B), at this point the excess carriers have a concentration that approximately equals the doping concentration. Thus, shifts in the inflection point IP correspond to shifts in the doping concentration.

Because of the complexity of the equations governing a doped layer in the real world (as compared to the just-described model illustrated by regions 912–914 in FIG. 9A), the concentration of excess carriers $n_e$ is obtained by using numerical modeling by computer 103C, rather than analytical equations. Such solutions, as well as actual measurements (see for example, FIG. 5B) have various attributes such as inflection points that are used to determine the various material properties (such as surface concentration, mobility and junction depth) as described above.

Lines 951–953 (FIG. 9B) illustrate surface carrier concentration C in illuminated region 120 as a function of power of generation beam 151, as obtained from numerical modeling. Specifically, lines 951–953 are for doping concentrations of $10^{16}$, $10^{17}$, and 10 atoms/cm$^3$, for a 0.2 μm thick implanted layer, on an epitaxial layer doped p-type at a level of $10^{16}$ atoms/cm$^3$, with beam 151 having radius 0.5 μm and wavelength 810 nm for structure 910.

For line 951, regions 912 and 913 have the same doping concentration, and the carrier concentration (at surface 923) as a function of power of generation beam 151 is a straight line, with the slope determined by the mobility. Inflection points 912I and 913I move to higher levels of power of generation beam 151 with increasing doping concentration, and the slopes $m_H$ at high level injection (slopes of regions 912H and 913H) drop as the doping increases, reducing the mobility. The slopes of line 951 and region 952H are approximately equal because the mobility drops only slightly (e.g. less than 5%) between $10^{16}$ and $10^{17}$/cm$^3$ doping.

As with bulk material 912 discussed above, the mobility and lifetime of layer 911 may also be found. To account for the complexity introduced by the multi-layered structure 910, a numerical model is created by computer 103C, and then fit with data such as carrier concentration C vs. laser power p and vs. radius r from the optical axis 155 (FIG. 1C) to determine material properties e.g. the mobility and lifetime. For example, the numerical model may indicate that an intensity measurement of a certain value (also called "expected value") is expected from a certain doped layer. If the mobility near the surface is degraded, the measured value is altered from the expected value, thus identifying a problem.

A reflected signal that is measured in step 243 (FIG. 2A) arises from the change in the surface reflection coefficient (also called "reflectance") due to concentration of excess carriers caused by beam 151 (FIG. 1C). The excess carriers (not shown) oscillate in the electric field of beam 151 illuminating the surface 153 (FIG. 1C). The oscillating carriers re-radiate light from beam 152. This re-radiated light adds to the reflection of beam 152 that occurs normally even in the absence of the excess carriers.

A solution for the reflected signal can be found analytically as described below using the Drude theory of conduction (see Handbook of Optics, Volume II, pages 35.3–35.7; Jackson "Classical Electrodynamics", sec. 7.7 and 7.8). The propagation constant in gaussian units for a poor conductor (4ps/we<<1) is $$k = m\left(\frac{\omega}{c}\right) = \left[\sqrt{\mu_m \varepsilon}\left(1 + i2\pi\frac{\sigma}{\varepsilon\omega}\right)\right]\left(\frac{\omega}{c}\right) \quad (14)$$

where s is the conductivity, ω is the radial frequency of the light, c is the speed of light, m is the index of refraction, $\mu_m$ is the magnetic permeability, and ε is the dielectric permittivity The first term is the complex index of refraction. In the present case, the magnetic permeability $\mu_m=1$, and $\varepsilon=m_O^2$, where $m_O$ is the index of refraction in the absence of illumination (3.42 for silicon).

From the Drude theory, the conductivity in the infrared is $$\sigma = -\frac{n_e(r)q^2}{im_e^*\omega} - \frac{n_h(r)q^2}{im_h^*\omega} = -\frac{q^2}{i\omega}\left(\frac{n_e(r)}{m_e^*} + \frac{n_h(r)}{m_h^*}\right) \quad (15)$$

where q is the electron charge, $m_e^*$ and $m_h^*$ are the electron and hole effective masses, and $n_e$ and $n_h$ are the electron and hole concentrations.

For silicon, the hole effective mass is independent of orientation. The electron effective mass, however, is orientation dependent, varying from 0.19 to 0.98 times the electron mass. For light illuminating a (100) crystal surface—this cut being the most common in integrated circuit processing—the effective mass has four-fold symmetry. Consequently, a reflected signal due to illumination with a polarization vector that rotates at a frequency f has a 4f frequency component due to the electrons, provides a means for measuring the electron concentration.

The imaginary conductivity means that the propagation constant in equation (14) is real. This is because optical frequency is so high that the electric field moves the carriers a very small distance and they do not collide with the lattice. The result is that they do not give up energy, so there is no absorption.

Combining equations (14) and (15), and multiplying the conductivity by $1/4\pi\epsilon_O$ to convert to MKS units, the index of refraction is $$m = m_0 + \Delta m = \sqrt{\varepsilon} - \frac{q^2}{2\varepsilon_0 m_0 m^* \omega^2}\left(\frac{n_e(r)}{m_e^*} + \frac{n_h(r)}{m_h^*}\right) \quad (16)$$

For normal incidence on conductive media from air (index of refraction=1), the reflection coefficient is given by $$R = \frac{(1-\eta)^2 + k^2}{(1+\eta)^2 + k^2} \quad (17)$$

This equation is an approximation, because probe beam 152 is focused on the surface 153 (FIG. 1C), so that the incident rays are not normal. However, the approximation is suitable to estimate the performance of profiler 103, and simplifies the analysis.

The variables in equation (17) relate to the index of refraction m by $$m = \eta + i\kappa \quad (18)$$

and the imaginary (absorption) term is related to the absorption coefficient of the medium by $$k = \frac{\alpha\lambda}{4\pi} \quad (19)$$

The form of the change in reflectance $\Delta R$ due to a change in index $\Delta m$ is found as follows. Ignoring the component of reflectivity due to absorption, which is typically very small, the reflectivity is $$R = \frac{(m-1)^2}{(m+1)^2} \approx \frac{(m_0-1)^2}{(m_0+1)^2}\left(1 + \frac{4\Delta m}{m_0^2 - 1}\right) = R_0\left(1 + \frac{4\Delta m}{m_0^2 - 1}\right) \quad (20)$$

where the approximation is found by substituting an index of refraction of the form $m = m_0 + \Delta m$, and retaining terms to order $\Delta m$. From equation 20, $$\Delta R(r_r) = \frac{4\Delta m(r_r)}{m_0^2 - 1} R_0 \quad (21)$$

The form of the change in index is found from the Drude theory (equation 20 above), $$\Delta m(r_r) = \frac{q_n^2(r_r)}{2\varepsilon_0 \varepsilon_s m^* \omega^2} \quad (22)$$

where $q = 1.602 \times 10^{-19}$ coulomb is the electron charge, $\epsilon_0 = 8.86 \times 10^{-12}$ F/m is the dielectric constant of free space, $\epsilon_s = 11.7$ is the relative dielectric constant of silicon, m* is the carrier effective mass, and w is the radial frequency of the infrared beam, $\omega = 2\pi c/l$, where $c = 3 \times 10^8$ m/sec is the speed of light and l is the wavelength. In equation (22), $n(r_r)$ is the radial carrier distribution, given by equation (12a) within the region 120 illuminated by generation beam 151, and equation (12b) outside the illuminated region 121, or as found using numerical models.

Therefore, in one embodiment, computer 103C (FIG. 1A is programmed to use equations (21) and (22) to determine the carrier distribution $n(r_r)$. Note that computer 103C multiplies $n(r_r)$ by $10^6$ to convert from /cm$^3$ to /m$^3$ if the constants given above are used, and the effective mass is in kilograms.

In equation (22) the electron and hole concentrations are assumed to be equal, since a photon generates an electron-hole pair, and net charge neutrality generally exists. For convenience, the electron and hole effective masses are considered equal, although this will not always be true.

Therefore, carrier concentration C is measured by profiler 103 (FIG. 1A) overlaying two beams (as shown in FIG. 1C): (1) generation beam 151 that generates excess carriers, and (2) probe beam 152 used to measure the reflectance attributable to the excess carriers. Wavelength l of the generation beam 151 is, in one embodiment, shorter than the wavelength of the probe beam 152, since the photon energy varies inversely with the wavelength, according to the relation $$E_{ph} = h\frac{c}{\lambda} \quad (23)$$

where h is Plank's constant and c is the speed of light.

Figure 8A:
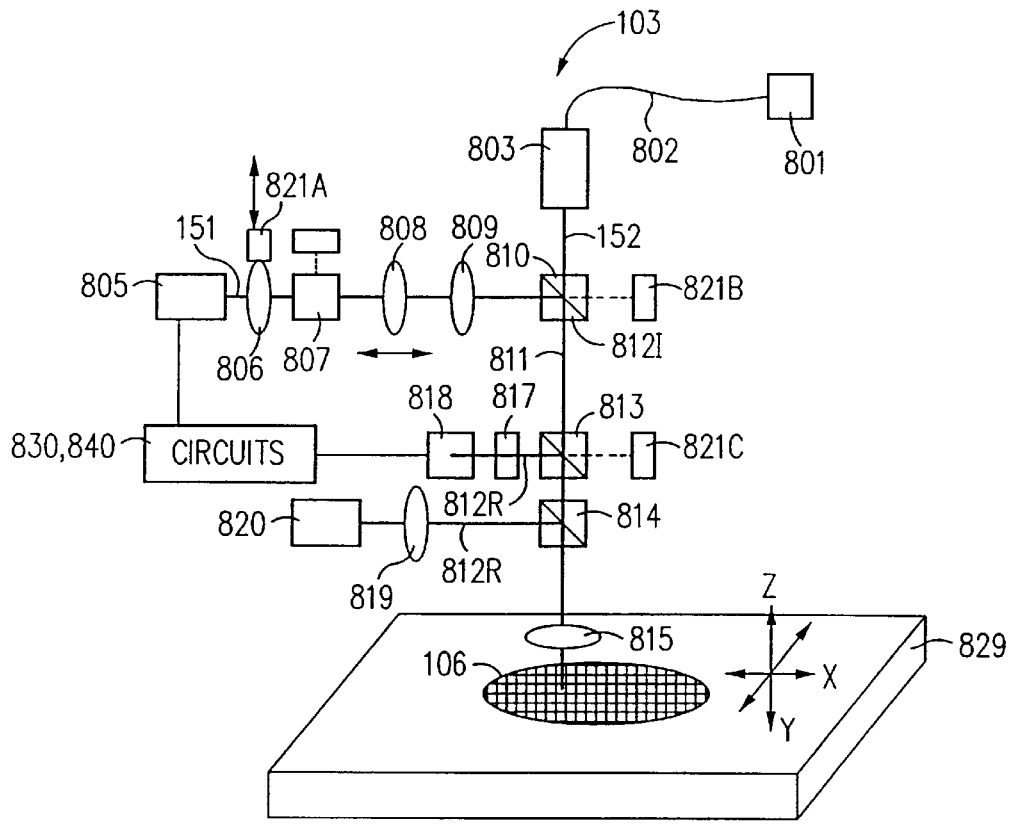
FIGS. 8A and 8B illustrate, in block diagrams, various components used in one implementation of the active dopant profiler of FIG. 1A.
Figure 8B:
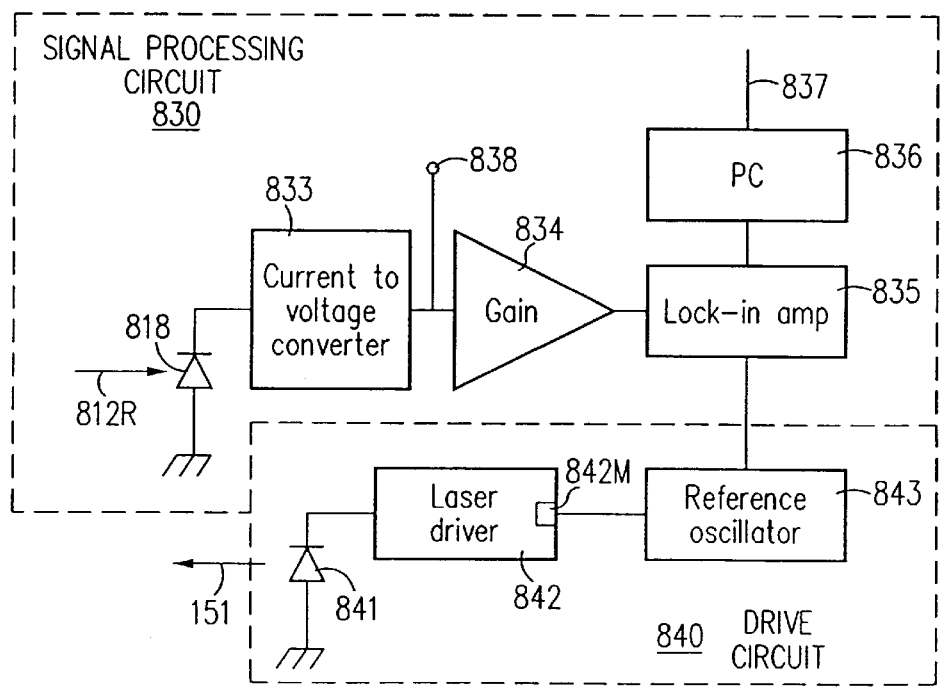

Furthermore, the minimum spot size $w_0$ varies with the wavelength as $$w_0 = \frac{0.61\lambda}{NA} \quad (24)$$

where NA is the numerical aperture of the focusing lens 415 (FIG. 8A).

Figure 1I:
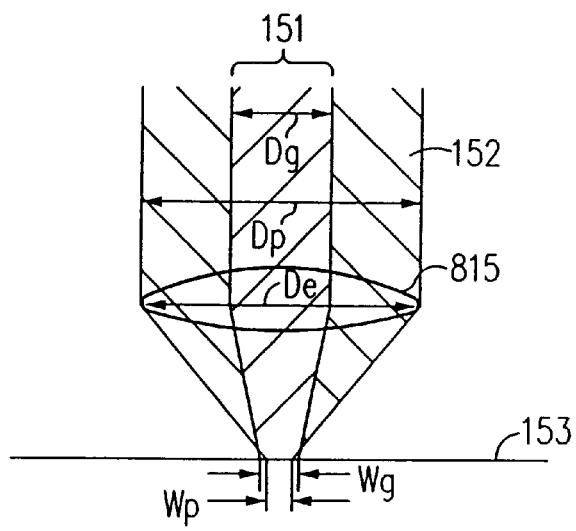
FIG. 1I illustrates, in a cross-sectional view, use of a common lens 815 to form probe beam 152 that has a smaller diameter at wafer surface 153 than generation beam 151, wherein the relation is reverse prior to passage through lens 815.

As these relations indicate, probe beam 152 has a larger minimum spot size than generation beam 151 when both beams 151 and 152 use identical lenses and have identical diameters. However, as discussed above, relative beam diameters can be chosen to make beams 151 and 152 of equal diameter at surface 153 (FIG. 1I). In one embodiment, equation (24) is used by computer 103C to measure the lifetime of the semiconductor material 156 (FIG. 1C), since the carrier concentration C decays away from the region illuminated by generation beam 151 as a function of $\sqrt{D\tau}$, where $\tau$ is the lifetime.

In a first approach, profiler 103 overlays the axes of both beams 151 and 152 and starts with probe beam 152 larger than generation beam 151. Then, profiler 103 gradually expands the size of generation beam 151 until beam 151 is as large as probe beam 152. During the process, profiler 103 measures the reflectance at each of a number of sizes of the generation beam 151, and plots these measurements to obtain a curved line, followed by determining various attributes (e.g. coefficients) for the curved line. Therefore, profiler 103 compares the coefficient values for a region (e.g. through a graph) with coefficient values of regions having known material properties, thereby to interpolate one or more material properties of the region.

In a second approach, profiler 103 overlays the two beams 151 and 152 with both at their minimum size. Then profiler 103 scans the generation beam 151 back and forth along a line, with the scan amplitude approximately equal to the diameter of probe beam 152. During the scanning, profiler 103 measures the reflected intensity, and provides an AC (alternating current) signal. Such an AC signal is detected with improved signal-to-noise ratio as compared to a direct current (DC) signal.

FIG. 1G shows the geometry of scanning one beam with respect to the other to determine a profile of the concentration of excess carriers as a function of distance along surface 153. The radii of the probe and generation beams 152 and 151 are Wp and Wg respectively. The axis of generation beam 151 is displaced from the axis of probe beam 152 by a distance Dx along the x axis, wherein the x and y axes define the surface plane of a wafer 105/106.

The power of a reflected portion of probe beam 152 is found by integrating the reflection coefficient over the area of the probe beam 152. A point within the probe beam 152 defined in cylindrical coordinates as (r,φ) is a distance $$r_r = r\sqrt{\left(\cos(\phi) - \frac{\Delta x}{r}\right)^2 + \sin(\phi)^2} \qquad (25)$$

$$= r\sqrt{1 - 2\frac{\Delta x}{r}\cos(\phi) + \left(\frac{\Delta x}{r}\right)^2}$$

from the origin of generation beam 151. The reflected power is then given by $$P_{ref} = \int_0^{2\pi} \int_0^{w_{IR}} I_i(r)\Delta R(r_r) r\,dr\,d\phi \qquad (26)$$

where $I_i(r)$ is the incident intensity of probe beam 152. For a uniform beam, $I_i(r) = P_{IR}/(\pi w_{ir}^2)$, and $$P_{ref} = \frac{P_{IR}}{\pi w_{IR}^2} \int_0^{2\pi} \int_0^{w_{IR}} \Delta R(r_r) r\,dr\,d\phi \qquad (27)$$

A method of measuring material properties using equation (27) is described above in reference to FIG. 7B. For example, FIG. 7B shows the excess carrier concentration (y axis) as a function of radial position displaced from the axis 155 of generation beam 151. As probe beam 152 is displaced according to the above procedure, probe beam 152 illuminates a region having a smaller number of carriers, and the reflection signal drops. The magnitude of this drop, and of the peak signal, is a function of the lifetime. A greater signal is obtained from a wafer without degraded lifetime (line 711) as opposed to a wafer with degraded lifetime (line 712).

Signal-to-noise ratio (SNR) can also be determined for the measurement method (e.g. method 200) described herein. The reflected signal is given by using equation (20) for the real part of the index, equation (23) for the imaginary part, and equation (21) for the fraction of power reflected, $$\Delta P = (R - R_0)P_{lw} \qquad (28)$$

where $$R_0 = \frac{(1 - m_0)^2}{(1 + m_0)^2} \qquad (29)$$

and $P_{lw}$ is the laser power of probe beam 152 at the wafer surface 153 (FIG. 1C).

The noise of the system is dominated by the shot noise in the detector photocell 818. The RMS shot noise power in the photocell 818 is $$P_{noise} = \sqrt{\frac{2qR_0 P_{lw} L(BW)}{A}} \qquad (30)$$

where BW is the bandwidth, A is the conversion efficiency of the photocell, and L is the loss in transmission through the optical system. For a reflectance $R_O=0.35$, laser power $P_{lw}=100$ mW, a loss L=0.2, a lock-in amplifier noise bandwidth of 0.3 Hz, and a conversion efficiency of A=0.6 amps/watt, the noise power is $P_{noise}=34$ picowatts. For a typical reflectance signal $\Delta R/R=10^{-6}$, where $\Delta R$ is the change in reflectance due to the concentration of excess carriers at the surface, the signal power is 20 nanowatts, and the signal-to-noise ratio (SNR) is 588. This is well above the SNR of 100 required to obtain a ±1% accuracy.

Although the generation beam 151 is modulated, the probe beam 152 is operated continuously at constant power (without modulation). The just-described act of beams 151 and 152 allows separation in measurement of two reflectances: a reflectance caused by the excess carriers from the background reflectance, since the former changes at the modulation frequency and can be detected in a synchronous manner.

The above calculations did not include the heating of surface 153 due to absorption of energy from generation beam 151. Such heating has the effect of reducing mobility. The temperature of region 120 (FIG. 1C) can be calculated using the radial diffusion equation. For silicon, limiting the incident power of generation beam 151 to a power on the order of 100 milliwatts limits the heating to a few (e.g. less than 10) degrees Centigrade, and therefore the above calculations still hold.

Alternatively, by increasing the power of generation beam 151, profiler 103 measures mobility as a function of temperature, thereby measuring mobility at the temperature that an integrated circuit in wafer 105/106 is expected to operate.

As described above, beam 151 that is used to generate carriers has photons of energy (also called "photon energy") greater than the bandgap energy of the semiconductor material, and beam 152 that is used to measure reflection has a photon energy lower than the bandgap energy. Therefore, the bandgap energy defines a "boundary line" between the photon energies of two beams 151 and 152 used in one embodiment. The use of two beams, one on each side of such a boundary line is a critical aspect in this embodiment. At 300 degrees Kelvin, the boundary line is 1.12 eV (wavelength of 1.11 μm) for silicon, 1.42 eV (0.87 μm) for GaAs, 0.66 eV (1.88 μm) for Ge, and 1.35 eV (0.92 μm) for InP.

In an alternative method, an act 1800 (FIG. 11) uses a polarized beam (not shown) of light that is focused (act 1801) onto surface 163 (FIG. 10A) of a semiconductor material 166 that has charge carriers generated (act 1802) by focusing an generation beam 151 (FIG. 1C) modulated as described above. The polarized beam is reflected (act 1803 in FIG. 11), and undergoes a polarization rotation upon reflection. The polarization rotation is caused by different reflection coefficients for the polarization components parallel and perpendicular to surface 163. The rotation is a function of the index of refraction. Therefore profiler 103 interferes (act 1804) the reflected portion with an unreflected portion of the incident beam, and measures (act 1805) a difference in magnitudes between the sum and difference components at the modulation frequency.

Thereafter, profiler 103 relates (act 1806) the measured difference to a property of the semiconductor material. Act 1806 is similar to act 250 described above in reference to FIG. 2A. However, in act 1800, instead of acts 244 and 241, profiler 103 performs the respective acts 1807 and 1808 and uses the measured differences to determine the material property in act 1806 as described herein.

The index of refraction is changed as a result of a change in the carrier concentration, as described by equation 22. A beam of polarized light reflected from surface 163 undergoes rotation of polarization that is a function of the index of refraction at surface 163. A measurement of this rotation is used to measure the change of index of refraction and, using equation 22, the concentration of excess carriers at surface 163.

Specifically, the polarization rotation measurement is used to measure material properties in a manner identical to the use of reflectance measurements as described earlier, in reference to FIGS. 5A–5H. Therefore, act 1800 (FIG. 11) is performed by profiler 103 (FIG. 1A) instead of act 240. That is, profiler 103 performs one or more of acts 210, 211, 213, 220 and 230 prior to act 1800, and performs acts 250 and 260 subsequent to act 1800, while using the polarization rotation measurement instead of the intensity measurement.

Moreover, profiler 103 measures various material properties of the semiconductor material (such as the dopant concentration, mobility, junction depth, lifetime, and defects that cause leakage of current during the act of an FET) in the manner described above except that profiler 103 uses the polarization rotation measurement instead of the intensity measurement. For example, in an act similar to the above-described act 243 (FIG. 2A), a number of polarization rotation measurements are obtained in a single location by changing the power of generation beam 151, and the measurements are plotted against the corresponding powers in a graph similar to FIG. 5A. Thereafter the slope of a line connecting the measurements is obtained and inverse of the slope indicates mobility as described above.

Specifically, a scaling factor is determined based on measurement of a reference sample, (similar to intensity measurement conversion to mobility as described above), to convert from units of signal to units of doping. The rotation measurements can also be performed in an offset position (FIG. 1F), or with generation and probe beams of differing size (FIG. 1G) to yield lifetime. Moreover, coincident beams 151 and 152 (FIG. 1C) can be scanned across a wafer in a manner similar to that described above in reference to FIGS. 3A and 3B, to identify changes in the material properties of the wafer.

At non-normal incidence of a light ray in the probe beam (not shown), there are two different reflection coefficients: One for the component of the electric field in the plane of the surface (called the "s component") and one for the component in a plane perpendicular to the plane of the surface (called the "p component"). The reflection coefficients for the s and p components are both functions of angle and the index of refraction of the semiconductor material 166 (FIG. 10), but have different forms. Consequently, the ratio of the s and p components is different before and after reflection. The reflected light emerging from a lens 168 has a different polarization from the incident light.

This polarization rotation is measured by interfering the reflected light with a reference beam coherent with the incident beam. Such a measurement may provide an increase in sensitivity of about two orders of magnitude over the use of a non-polarized beam (in act 240 of FIG. 2A), as described below in reference to equation (48).

Figure 10A:
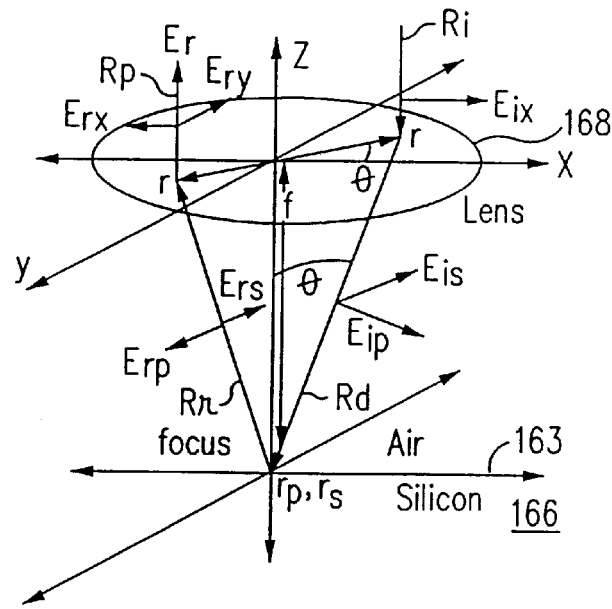
FIG. 10A illustrates, in a schematic diagram, the rotation of a plane of polarization of a probe beam after reflection by the semiconductor material.
Figure 10B:
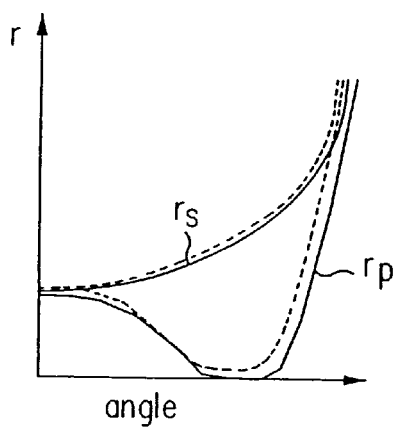
FIG. 10B illustrates, in a graph, the reflectance measurement plotted along the y axis as a function of angle of incidence of the probe beam plotted along the x axis, wherein solid and dotted lines show relative effect of a small increase in the index of refraction (dotted line higher index than solid) due to an increase in the surface carrier concentration of the two polarization components rs and rp.
Figure 10C:
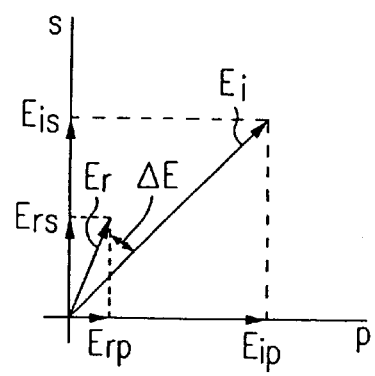
FIG. 10C illustrates, in a vector diagram, an angle through which the polarization plane is rotated after reflection as illustrated in FIG. 10A.
Figure 11:
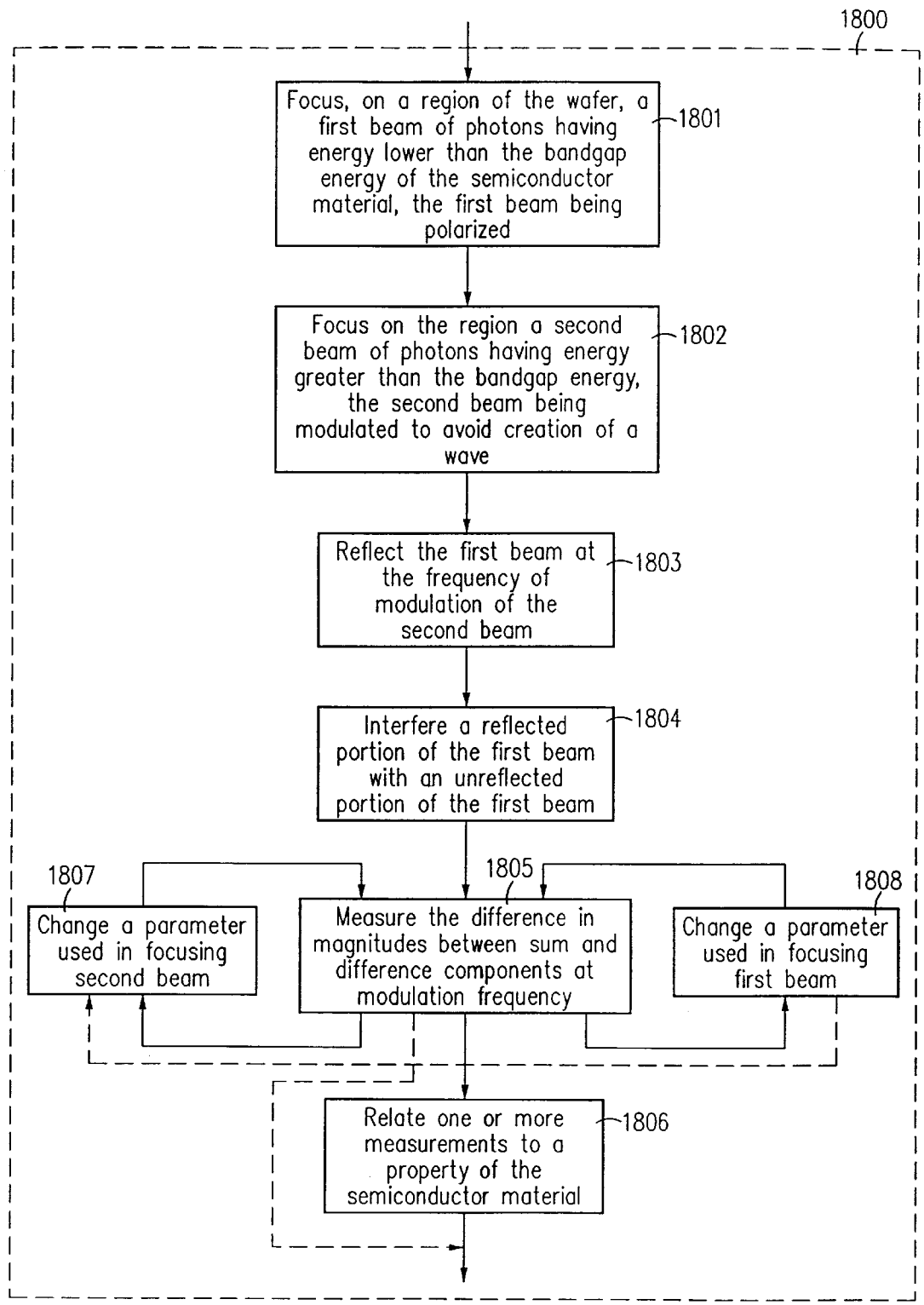
FIG. 11 illustrates, in a flowchart, various acts performed by the active dopant profiler of FIG. 1A using a polarized probe beam as illustrated in FIG. 10A.

A plane wave with polarization along the x axis illuminates a lens 168 (FIG. 10A). The incident planewave has an electric field amplitude $E_{ix}$. The plane wave illuminating lens 168 is made up of a set of rays of light. To derive the polarization rotation, the following analysis traces one of these rays as it reflects from interface 163.

Specifically, a ray Ri of the polarized beam intercepts lens 168 at a radius r and angle φ with respect to the x axis. Lens 168 diffracts ray Ri so that diffracted ray Rd propagates toward the focus f, located at the origin, a distance f from lens 168 along the z axis. Diffracted ray Rd has electric field components $E_{is}$ parallel to the x–y plane (a plane parallel to the wafer surface), and $E_{ip}$ in a plane perpendicular to the x–y plane. The angle of the diffracted ray Rd with respect to the z axis is q.

After reflection, ray Rr has electric field components $E_{rs}=r_sE_{is}$ and $E_{rp}=r_pE_{ip}$, where $r_s$ and $r_p$ are the amplitude reflection components. These components are illustrated as a function of angle in the graph in FIG. 10B. Since $r_s$ and $r_p$ are equal only at q=0 (for a ray along the z axis), the ratios $E_{ix}/E_{iy}$ and $E_{rx}/E_{ry}$ are not equal, and the polarization of reflected ray RR is rotated with respect to incident ray RI (the polarization is the direction of the electric field vector, which is the vector sum of the s- and p-components, as shown in the graph in FIG. 10C.

Reflected ray rr (FIG. 10A) strikes lens 168 at a radius r. The lens refracts the reflected ray parallel to the z axis. Refracted ray $r_r$ emerges parallel to the incident ray, but with a changed polarization.

The reflection coefficients $r_s$ and $r_p$ are functions of the angle of incidence and the index of refraction. A change in the index of refraction causes a shift in both reflection coefficients, as shown qualitatively by the dotted lines in the graph in FIG. 10B. Consequently, any change in the index of refraction causes a change in the polarization of the exiting ray RP. An interferometer measures the polarization rotation resulting from any change in the index of refraction of the silicon.

Figure 12:
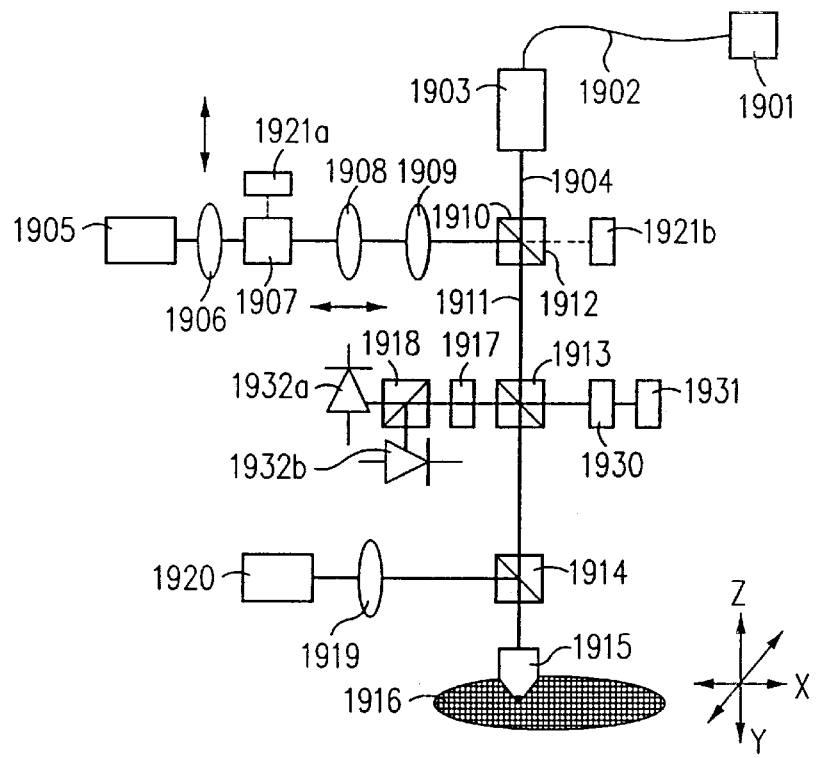
FIG. 12 illustrates, in a block diagram, another implementation of the active dopant profiler of FIG. 1A.

A profiler 1900 (FIG. 12) that uses polarization as described above includes elements 1918, 1930, 1931, and 1932a and b that together form an interferometer. Profiler 1900 operates in a manner similar or identical to the above-described act of profiler 103 except for the following differences.

50:50 beam splitter 1913 diverts 50% of the reflected beam to the left, in the direction of the detectors. Splitter 1913 also diverts 50% of the beam incident from lasers 1901 and 1905 to the right to create the reference beam. Phase plate 1930 is a retarder that is rotated to align the polarization of the reference beam. Mirror 1931 reflects the reference beam back toward the detector. The net retardation of the reference beam is double the retardation from a single pass through phase plate 1930. Both the reference beam and the reflected beam pass through narrow band filter 1917 to remove the generation beam radiation from laser 1905, allowing only radiation at the probe beam wavelength from laser 1901 to reach the detector.

Polarizing beam splitter 1918 interferes the two beams. Splitter 1918 is aligned with polarization axes at approximately 45° to polarization axes of the reflected and reference beams, so that components representing the sum and difference of the reflected and reference beam electric fields are sent to detectors 1932a and 1932b. The currents from detectors 1932a and 1932b, which are germanium photodiodes, are converted to voltages using transimpedance amplifiers. The voltages from the two amplifiers are subtracted from one another to provide a signal that is fed to the lock-in amplifier and detected with reference to the modulation of the pump laser 1905.

Assume an incident electric field polarized along the x-axis with amplitude $$E_0 = \sqrt{\frac{P_1}{\pi w^2}} \qquad (34)$$

where $P_1$ is the probe laser power incident at the objective lens and w is the beam radius. Through ray tracing, the reflected beam vector emerging from lens 168 (FIG. 10A) is $$E_r = E_0 \left( \frac{E_{rx}}{E_0}, \frac{E_{ry}}{E_0} \right) \qquad (35)$$
$$= E_0 (r_p \cos^2(\phi)\cos(\theta) - r_s \sin^2(\phi), \sin(\phi)\cos(\phi))(r_p \cos(\theta) + r_s)$$

where $r_s$ and $r_p$ are the amplitude reflection coefficients for the s- and p-polarizations, and transmission loss in the lens has been ignored. The amplitude reflection coefficients are given by the relations $$r_s = -\frac{\sin(\theta - \theta_1)}{\sin(\theta + \theta_1)}$$

and $$r_s = \frac{\tan(\theta - \theta_1)}{\tan(\theta + \theta_1)}$$

where $q_1$ is related to the angle of incidence with respect to the surface normal q by $$\frac{\sin(\theta)}{\sin(\theta_1)} = \frac{1}{n_s}$$

where ns is the index of refraction of the silicon and the incident medium is assumed to be air, with an index of refraction of one.

The carrier concentration dependence of the polarization rotation comes in through the amplitude reflection coefficients $r_s$ and $r_p$, which are both functions of the complex index of refraction, $$\bar{n} = n_s + ik \qquad (36)$$

In semiconductors, the real part is given by $$n = n_{so} + \Delta n = n_{so} - \frac{q^2 N}{2\varepsilon_o n_{so} m^* \omega^2} = n_{so} - \frac{2\pi^2 q^2 N \lambda^2}{\varepsilon_o n_{so} m^* c^2} \qquad (37)$$

where $n_{so}$ is the index of refraction in the absence of carrier concentration N, q is the electron charge, $e_0$ is the dielectric constant of free space, m* is the effective mass of the carriers, c is the speed of light, 1 the wavelength, and w is the frequency of the probe light. Equation (37) is found using the Drude theory, described in Jackson.

The imaginary part k relates to the absorption coefficient a and the wavelength $\lambda$ as $$k = \frac{\alpha(\lambda)\lambda}{4\pi} \qquad (38)$$

In silicon, a has two main components, one due to band-to-band absorption and a second due to free carriers, $$\alpha(\lambda) = \alpha_{bb}(\lambda) = \alpha_b(\lambda) \qquad (39)$$

$\alpha_{bb}$ may be looked up in common references. A fit, valid over the wavelength range of 0.4 to 1.5 $\mu$m, is $$\log_{10}(\alpha(\lambda)) = 9.519 - 19.826\lambda + 23.262\lambda^2 - 10.857\lambda^3 \qquad (40)$$

An approximate form of the free carrier absorption term in silicon is $$\alpha_f = \frac{4N}{10^{17}} \left( \frac{\lambda}{9} \right)^2 \qquad (41)$$

where the wavelength $\lambda$ is in units of microns and the free carrier concentration N is in units of 1/cm$^3$.

From equations (37) and (41), it is seen that both the real and imaginary parts of the index of refraction are functions of the carrier concentration. Note that the dependence becomes stronger at longer wavelengths, and therefore use of a longer wavelength probe beam is preferred.

The size of the probe beam spot cannot be made arbitrarily large, however, since too large a spot may not fit into patterns in integrated circuits. The diameter of the spot for a gaussian beam is $$2w_0 = \frac{1.22\lambda}{NA} \qquad (42)$$

where the wavelength 1 is in units of microns and NA is the numerical aperture of the lens. For a wavelength of 0.8 $\mu$m and NA of 0.9, the spot size is about 1 $\mu$m.

The polarization rotation is measured by interfering the reflected beam with the reference beam. The reference and reflected beams propagate along the same axis to the polarizing beam splitter 1918, which sends sum and difference components to the two detectors 1932a and 1932b. The field for the sum component is $$E_+ = \left( E_{rx} + \frac{E_{ref}}{\sqrt{2}} \right) \qquad (43)$$

and for the difference component is $$E_- = \left( E_{ry} - \frac{E_{ref}}{\sqrt{2}} \right) \qquad (44)$$

The current in each detector is proportional to the incident power, which is the squared magnitude of the electric field. At each illuminated point on the surface of the photocell receiving the sum component there is a power density $$P_+ = \frac{|E_{ref}|^2}{2} + \frac{E_{ref}}{\sqrt{2}}(E_{rx} + E_{rx}^*) + |E_{rx}|^2 \quad (45)$$

and on the photocell receiving the difference component there is a power density $$P_- = \frac{|E_{ref}|^2}{2} - \frac{E_{ref}}{\sqrt{2}}(E_{ry} + E_{ry}^*) + |E_{ry}|^2. \quad (46)$$

The net signal current is found by integrating these power densities over each photocell, multiplying by the conversion efficiency A (usually in amps/watt), and subtracting from one another. The result is $$I_{netsig} = A\frac{E_{ref}}{\sqrt{2}} \int_0^{2\pi} \int_0^w (E_{rx} + E_{rx}^* + E_{ry} + E_{ry}^*) r\, dr\, d\phi \quad (47)$$

where the terms in $E_{rx}^2$ and $E_{ry}^2$ are neglected as small. The signal current is the difference between the net signal current and the signal current when the generation beam power is zero, given by $$I_{sig} = A\frac{E_{ref}}{\sqrt{2}} \left[ \int_0^{2\pi} \int_0^w [(E_{rx} + E_{rx}^* + E_{ry} + E_{ry}^*)] r\, dr\, d\phi - \int_0^{2\pi} \int_0^w [(E_{rx0} + E_{rx0}^* + E_{ry0} + E_{ry0}^*)] r\, dr\, d\phi \right] \quad (48)$$

Shot noise is usually the largest contributor to noise, given by $$I_{shot} = A\sqrt{\frac{2qBW}{A}\left(\frac{P_1}{2}\right)} = \sqrt{qAP_1BW} \quad (49)$$

The factor of two arises because the reference beam is split between the two photocells. The signal-to-noise ratio (SNR) is the ratio $I_{sig}/I_{shot}$.

Figure 13:
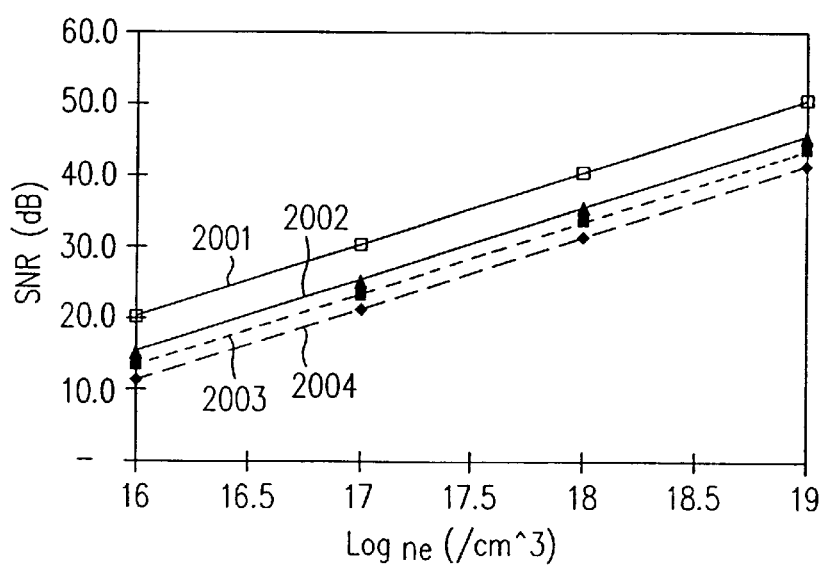
FIG. 13 illustrates, in a graph, the signal-to-noise ratio plotted along the y axis as a function of the concentration of carriers plotted along the x axis as straight lines for four different wavelengths of the probe beam.

FIG. 13 illustrates the SNR in dB (10 dB per decade) as a function of the $\log_{10}$ of the doping concentration. The NA is 0.9 and the probe laser power at the silicon and the reference beam powers are both 1 mW. The beam radius is 0.35 cm and the photodetector conversion efficiency is 0.4 A/W, for simplicity assumed independent of wavelength. The noise bandwidth is 0.3 Hz. The background doping concentration is $10^{15}$ for the $10^{16}$ doping point, and $10^{16}$ for the other points.

Graphs of SNR as a function of the log of dosage are shown in FIG. 13 for four wavelengths (0.53 µm for line 2004, 0.67 µm for line 2003, 0.83 µm for line 2002, and 1.48 µm for line 2001). The response to doping is linear, and the effect of wavelength is small. Note that the SNR is in the range of 10–20 dB for even the lowest doping, and is greater than 20 dB for doping concentration in excess of $10^{17}/cm^3$. The linear nature of line 2001 indicates that the polarized beam measurement can be used in each of the methods discussed above, e.g. in reference to FIGS. 5A–5H.

Numerous modifications and adaptations of the above-described embodiments will become apparent to a person skilled in the art of semiconductor physics. For example, although computer 103C is described as being programmed with one or more specific equations, computer 103C can be programmed with other equations described herein, or with one or more equations that approximate any of the relations between material properties as described herein, for use with measurements performed by profiler 103 while creating a diffusive modulation of charge carriers in a wafer under measurement. For example, an approximate equation used by profiler 103 to measure a material property can be obtained by curve-fitting to measurement data from reference wafers, or by curve-fitting to data obtained from a numerical model, or both depending on the specific implementation.

Therefore, numerous such modifications and adaptations of the above-described embodiments are encompassed by the attached claims.

What is claimed is:

1. An apparatus for evaluating a wafer, said apparatus comprising:

a first source of a first beam of photons having a first intensity modulated at a frequency sufficiently low to avoid creation of a wave of charge carriers in a region of said wafer when said first beam is incident on said region;

a second source of a second beam of photons, said photons in said second beam having energy sufficiently lower than said energy of said photons in said first beam to avoid creation of more than a negligible number of charge carriers in said region when said second beam is incident on said region; and a photosensitive element located in a path of a portion of said second beam, said portion being modulated at said frequency after reflection by said region, said photosensitive element generating a first signal indicative of a first concentration of said charge carriers created in said region by incidence of said first beam.

2. The apparatus of claim 1 further comprising:

a computer coupled to said photosensitive element and programmed to determine a value of a material property in said region by use of said first signal and a second signal generated by said photosensitive element in response to a change in a parameter related to generation of at least one of said first beam and said second beam.

3. The apparatus of claim 2 wherein:

said parameter is intensity of said first beam; and
   said computer is programmed to:
   compute a ratio of (a) difference between said first signal and said second signal and (b) difference between said first intensity and said second intensity; and
   compare said ratio with a corresponding ratio of a predetermined wafer having a known mobility to determine mobility in said region.

4. The apparatus of claim 2 wherein:

said computer determines a value of an attribute, the attribute being a change in said second signal for a unit change in said first signal; and
   said computer uses the formula $$\mu_{unk} = \frac{m_{ref}}{m_{unk}} \mu_{ref}$$

to compute mobility in said region, wherein $m_{unk}$ is said value of said attribute, $m_{ref}$ is another value of said attribute for a reference wafer, and $\mu_{ref}$ is the mobility of said reference wafer.

5. The apparatus of claim 2 wherein:

said second signal is generated at a distance from said region, said parameter being said distance; and said computer uses a predetermined range of lifetimes of wafers that are acceptable, and a corresponding range of intensity measurements at said distance of wafers having known lifetimes to determine whether said wafer has an acceptable lifetime.

6. The apparatus of claim 2 wherein:

said parameter is the diameter of one of said beams; and said computer uses a predetermined range of lifetimes of wafers that are acceptable, and a corresponding range of intensity measurements for said diameter of said probe beam to determine whether said wafer has an acceptable lifetime.

7. The apparatus of claim 2 wherein said computer is programmed to:

compute a plurality of coefficients of at least a group of said signals when plotted against corresponding values of said parameter; and compare at least one coefficient in said plurality with a corresponding coefficient of a predetermined wafer having a known value of a material property to determine a value of said material property in said region.

8. The apparatus of claim 7 wherein:

said parameter is intensity of said first beam; and said coefficient is a first order coefficient and the material property is junction depth.

9. The apparatus of claim 7 wherein:

said parameter is intensity of said first beam; and the coefficient is a first order coefficient and the material property is mobility.

10. The apparatus of claim 7 wherein:

said parameter is intensity of said first beam; and the coefficient is a zeroth order coefficient and the material property is surface concentration.

11. The apparatus of claim 7 wherein:

said parameter is intensity of said first beam; and the coefficient is a first order coefficient and the material property is sheet resistance.

12. The apparatus of claim 2 wherein said computer is programmed to:

compute a plurality of coefficients of a plot of said signals against corresponding values of said parameter, said parameter being intensity of said first beam; and compare at least one coefficient in said plurality with a corresponding coefficient of a predetermined wafer having been subjected to a process at a known value of a process condition to determine a value of said process condition for said wafer.

13. The apparatus of claim 2 wherein said computer is programmed to:

determine an intersection point of a first line that approximates a high power portion formed by a first group of said signals at a first extremity in a range of values of said signals and a second line that approximates a low power portion formed by a second group of said signals at a second extremity in said range; and compare a coordinate of said intersection point with a corresponding coordinate of an intersection point of a predetermined wafer having a known concentration of active dopants to determine the concentration of active dopants in said region.

14. The apparatus of claim 2 wherein:

said parameter is a diameter of one of said beams; and the material property is lifetime.

15. The apparatus of claim 2 wherein:

said parameter is a distance between said first beam and said second beam; and the material property is lifetime.

16. The apparatus of claim 1 further comprising:

a wafer processing unit; and a computer coupled to said wafer processing unit and to said photosensitive element, said computer being programmed to control operation of said wafer processing unit based on at least said first signal.

17. The apparatus of claim 16 further comprising a rapid thermal annealer, wherein:

said wafer processing unit includes an ion implanter; and said computer is coupled to said rapid thermal annealer, and is programmed to control operation of at least one of said ion implanter and said rapid thermal annealer based on at least said first signal.

18. The apparatus of claim 1 further comprising:

a rapid thermal annealer; and a computer coupled to said rapid thermal annealer and programmed to control operation of said rapid thermal annealer based on at least said first signal.

19. The apparatus of claim 1 further comprising:

a computer programmed to display on a monitor a message indicating acceptance or rejection of a wafer under measurement, the computer being couled to said photosensitive element.

20. The apparatus of claim 1 further comprising:

means for processing said wafer; and a computer coupled to said means for processing and to said photosensitive element, said computer being programmed to control said means for processing in response to at least said first signal generated by said photosensitive element.

21. The apparatus of claim 1 further comprising:

a stage capable of moving said wafer with respect to said first source and said second source; wherein:

said photosensitive element generates a plurality of signals related to a corresponding plurality of regions on said wafer when said wafer is moved by said stage.

22. The apparatus of claim 21 further comprising:

a computer coupled to said photosensitive element and programmed to compute a ratio of a local maximum in said plurality of signals to a local minimum in said plurality of signals, compare the ratio with a predetermined limit, and display a message on a monitor indicating acceptance or rejection of said wafer.

23. The apparatus of claim 21 further comprising:

a computer coupled to said photosensitive element and programmed to check if any of said plurality of signals falls outside a predetermined range, and display a message on a monitor indicating acceptance or rejection of said wafer.

24. The apparatus of claim 21 further comprising:

a computer coupled to said photosensitive element and programmed to determine a value of a material property in said region by use of said first signal and a second signal generated by said photosensitive element for said region after a change in intensity of said first beam.

25. The apparatus of claim 21 wherein:

said stage moves said wafer in two dimensions; and said photosensitive element generates at least one signal in said plurality of signals at each region in said plurality of regions.

26. The apparatus of claim 21 further comprising:

a rapid thermal annealer; and said computer is programmed to control operation of said rapid thermal annealer in response to one of said plurality of signals.

27. The apparatus of claim 1 wherein:

said first source generates first photons having energy greater than bandgap energy of a semiconductor material in said region; and said second source generates second photons having energy lesser than said bandgap energy.

28. The apparatus of claim 27 wherein:

said first photons have a first wavelength smaller than 950 nm; and said second photons have a second wavelength larger than 950 nm.

29. The apparatus of claim 1 wherein:

said first beam has a first diameter at a surface of said wafer;

said second beam has a second diameter at said surface; and said first diameter is greater than or equal to said second diameter.

30. An apparatus for generating an electrical signal indicative of a property of a region in a wafer, said wafer including a semiconductor material at said region, said apparatus comprising:

an oscillator oscillating at a frequency lower than 1000 KHz during operation;

a first source of a first beam, said first source being coupled to said oscillator to generate said first beam at an intensity modulated at said frequency, said first beam containing a plurality of first photons having energy greater than the bandgap energy of said semiconductor material thereby to create a plurality of charge carriers when incident on said region, the number of said plurality of charge carriers being modulated at said frequency without the creation of a wave;

a second source of a second beam, said second beam containing a plurality of second photons having energy lower than said bandgap energy;

a partially transmissive mirror located in the path of each of said first beam and said second beam, said partially transmissive mirror being positioned to reflect one of said first beam and said second beam along a path coincident with the path of the other of said first beam and said second beam thereby to create a combined beam;

a beam splitter positioned in said coincident path;

a sensor capable of sensing said second photons, said sensor being coupled to said beam splitter to receive a group of second photons reflected by said region;

a lock-in amplifier coupled to said oscillator and to said sensor, said lock-in amplifier having an output line;

wherein said lock-in amplifier generates on said output line a signal indicative of an average number of said second photons modulated at said frequency and reflected by said region.

31. The apparatus of claim 30 wherein:

said sensor includes germanium.

32. The apparatus of claim 30 wherein said first beam has a power that is adjustable by said first source, and the apparatus further comprises:

a computer coupled to said output line and programmed to determine a value of a material property in said region in response to a plurality of values of said second signal generated by adjusting said power of said first beam to a corresponding plurality of levels.

33. The apparatus of claim 30 wherein:

said frequency of modulation by said first source is smaller than 10 Khz.

34. An apparatus for measuring a property of a wafer, said wafer including a semiconductor material, said apparatus comprising:

an oscillator capable oscillating at a frequency smaller than 1000 KHz;

a first source of a first beam, said first source being coupled to said oscillator to generate said first beam at an intensity modulated at said frequency, said first beam containing a plurality of first photons having energy greater than the bandgap energy of said semiconductor material thereby to create a plurality of charge carriers when incident on a region of the semiconductor material, the number of said plurality of charge carriers being modulated at said frequency;

a second source of a second beam, said second beam containing a plurality of second photons having energy lower than said bandgap energy, said second beam being polarized;

a partially transmissive mirror located in the path of each of said first beam and said second beam, said partially transmissive mirror being positioned to reflect one of said first beam and said second beam along a path coincident with the path of the other of said first beam and said second beam;

a polarizing beam splitter located in the path of reflection of said second beam from said wafer;

a first sensor coupled to said polarizing beam splitter to receive a first portion of electromagnetic radiation from said polarizing beam splitter; and a second sensor coupled to said polarizing beam splitter to receive a second portion of electromagnetic radiation from said polarizing beam splitter;

wherein said first portion and said second portion are respectively the sum and difference components of interference of:

a portion of said second beam prior to said reflection by said wafer; and another portion of said second beam subsequent to said reflection by said wafer.

35. The apparatus of claim 34 further comprising:

a lock-in amplifier coupled to said first sensor and to said second sensor;

wherein said lock-in amplifier generates a third signal indicative of the difference between a first signal from said first sensor and a second signal from said second sensor on receipt of said first signal and said second signal, said third signal being in phase with oscillations of said oscillator.

36. The apparatus of claim 34 wherein said power of said first beam generated by said first source is adjustable, and the apparatus further comprises:

a computer coupled to said lock-in amplifier and programmed to determine a value of a material property in said region in response to a plurality of values of said third signal generated by adjusting said power of said first beam to a corresponding plurality of levels.

37. A method for evaluating a wafer, said method comprising:

creating a plurality of charge carriers in a region of said wafer, the number of said charge carriers being modulated at a frequency that is sufficiently low to avoid creation of a wave of said charge carriers;

focusing on said region a first beam of first photons having energy lower than bandgap energy of a semiconductor material in said region; and measuring a first intensity of a portion of said first beam modulated at said frequency after reflection by said region.

38. The method of claim 37 further comprising:

changing a parameter used in said creating;

measuring a second intensity after said changing; and using each of said first intensity and said second intensity to determine a value of a material property in said region.

39. The method of claim 37 wherein:

said parameter is a distance between said first beam and said region; and said material property is lifetime.

40. The method of claim 37 wherein:

said parameter is diameter of one of said beams; and said material property is lifetime.

41. The method of claim 37 wherein:

said creating includes focusing on said region a second beam of second photons having a second intensity modulated at said frequency; and said parameter is an average of said second intensity over a cycle at said frequency.

42. The method of claim 41 further comprising:

determining an attribute of a function, said function at least approximately relating said first intensity and said average of said second intensity to the corresponding values of said parameter before and after said changing; and interpolating said attribute with respect to a plurality of attributes of corresponding functions of semiconductor materials having known values of a material property thereby to determine the value of said material property in said region.

43. The method of claim 42 wherein:

said attribute is a coefficient of a straight line that approximates at least a portion of said function; and said property is one of junction depth, surface concentration, sheet resistance and mobility.

44. The method of claim 43 wherein:

said coefficient is slope;

said portion approximates a group of said signals at a high end of a range of said plurality of signals; and said material property is mobility.

45. The method of claim 43 wherein:

said coefficient is slope;

said portion approximates a group of said signals at a low end of a range of said plurality of signals; and said material property is junction depth.

46. The method of claim 43 wherein:

said coefficient is intercept; and said material property is surface concentration.

47. The method of claim 42 wherein:

said attribute is a coordinate of an intersection point of a first line that approximates a high power portion formed by a first group of said signals at a first extremity in a range of values of said signals and a second line that approximates a low power portion formed by a second group of said signals at a second extremity in said range; and said property is doping concentration.

48. The method of claim 42 wherein said wafer is a patterned wafer and said method further comprising:

annealing said wafer prior to said measuring; and adjusting annealing of another patterned wafer depending on at least said second intensity.

49. The method of claim 42 further comprising:

repeating said creating and said focusing in a plurality of regions of said wafer; and measuring a plurality of intensities corresponding to said plurality of regions.

50. The method of claim 49 further comprising:

comparing each of said intensities with a predetermined limit to determine a number of defects, each defect being indicated by an intensity exceeding said predetermined limit.

51. The method of claim 49 further comprising:

computing a ratio of a local maximum in said plurality of intensities to a local minimum in said plurality of intensities; and comparing the ratio with a predetermined limit to determine acceptance or rejection of said wafer.

52. The method of claim 37 further comprising:

changing an average concentration of charge carriers in said region;

measuring a second intensity after said changing;

using each of said first intensity and said second intensity to determine a value of a material property in said region;

repeating said creating and said focusing in a plurality of regions of said wafer; and measuring a plurality of intensities corresponding to said plurality of regions.

53. A method for evaluating a wafer, said method comprising:

focusing on a region of said wafer a first beam of first photons having energy lower than the bandgap energy of a semiconductor material in said region, said first beam being polarized;

focusing on said region a second beam of second photons having energy greater than said bandgap energy, said second beam having an intensity modulated at a predetermined frequency, said second beam creating a plurality of charge carriers when incident on said region, said predetermined frequency being sufficiently small to avoid the creation of a wave of said charge carriers;

reflecting said first beam at said predetermined frequency by using said charge carriers;

interfering a reflected portion of said first beam with an unreflected portion of said first beam to obtain a sum component and a difference component;

measuring a difference between a first magnitude of said sum component and a second magnitude of said difference component.

54. The method of claim 53 further comprising, prior to said interfering:

passing said reflected portion and said unreflected portion through a filter, said filter blocking the passage of said second beam.

55. The method of claim 53 further comprising:

annealing said wafer prior to said focusing; and adjusting annealing of another wafer depending on said difference.

56. The method of claim 53 further comprising:

interpolating said difference with respect to a plurality of difference measurements of semiconductor materials having known values of a material property to determine a value of said material property in said region.

57. The method of claim 53 further comprising:

changing a parameter used in said focusing on said region; and measuring another difference after said changing.

58. The method of claim 53 further comprising:

determining a coefficient of a function, said function relating said difference and said another difference to the corresponding values of said parameter before and after said changing; and interpolating said coefficient with respect to a plurality of coefficients of corresponding functions of semiconductor materials having known values of a material property to determine a value of said material property in said region.

59. The method of claim 53 wherein:

said wafer has a plurality of doped regions.

60. A method for evaluating a wafer, said method comprising:

creating a plurality of charge carriers in a region of said wafer, the number of said charge carriers being modulated at a frequency that is sufficiently low to avoid creation of a wave of said charge carriers;

focusing on said region a probe beam of photons having energy lower than bandgap energy of a semiconductor material in said region;

measuring a first intensity of a portion of said probe beam modulated at said frequency after reflection by said region;

changing the concentration of said charge carriers at a surface of said wafer;

measuring, after said changing, a second intensity of a portion of said beam modulated at said frequency after reflection by said region;

determining a value of an attribute of a function that relates, at least approximately, said first intensity and said second intensity to the corresponding values of said concentration before and after said changing; and interpolating said attribute with respect to a plurality of attributes of corresponding functions of semiconductor materials having known values of a property thereby to determine the value of said property in said region.

61. The method of claim 60 wherein:

said property is mobility $\mu_{unk}$; and said interpolating includes using the formula $$\mu_{unk} = \frac{m_{ref}}{m_{unk}} \mu_{ref}$$

to compute mobility, wherein $m_{unk}$ is said value of said attribute, $m_{ref}$ is another value of said attribute for a reference wafer, and $\mu_{ref}$ is the mobility of said reference wafer.

62. The method of claim 60 wherein said creating includes focusing on said region a generation beam having an intensity modulated at said frequency, said method further comprising:

moving said probe beam relative to said generation beam;

measuring intensity after said moving;

repeating said moving and said measuring at least once;

determining a value of said distance at which said intensity is the largest; and using said value to maintain said probe beam in alignment with said generation beam.

63. The method of claim 60 wherein said wafer is formed of prime material.

* * * * *